(12) United States Patent
Mazur et al.

(10) Patent No.: US 6,913,130 B1
(45) Date of Patent: *Jul. 5, 2005

(54) METHOD AND APPARATUS FOR DOCUMENT PROCESSING

(75) Inventors: Richard A. Mazur, Naperville, IL (US); Douglas U. Mennie, Barrington, IL (US); Mark C. Munro, Park Ridge, IL (US); Lars R. Stromme, Holmestrand (NO); Bradford T. Graves, Arlington Heights, IL (US); William J. Jones, Kenilworth, IL (US)

(73) Assignee: Cummins-Allison Corp., Mt. Prospect, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/542,487

(22) Filed: Apr. 3, 2000

Related U.S. Application Data

(63) Continuation of application No. 08/864,423, filed on May 28, 1997, which is a continuation-in-part of application No. 08/800,053, filed on Feb. 14, 1997, now Pat. No. 5,992,601.
(60) Provisional application No. 60/034,954, filed on Jan. 16, 1997, provisional application No. 60/038,340, filed on Feb. 27, 1997, provisional application No. 60/018,563, filed on May 29, 1996, and provisional application No. 60/011,688, filed on Feb. 15, 1996, now abandoned.

(51) Int. Cl.$^7$ ................................................ G07D 7/20
(52) U.S. Cl. ........................................ 194/207; 194/206
(58) Field of Search ........................ 382/135; 209/534; 194/207, 215, 229, 230, 240, 317; 271/3.15

(56) References Cited

U.S. PATENT DOCUMENTS

| | | | |
|---|---|---|---|
| 3,246,295 A | 4/1966 | DeClaris et al. | 382/56 |
| 3,280,974 A | 10/1966 | Riddle et al. | 209/111.8 |
| 3,409,109 A | 11/1968 | Iizuka et al. | 194/4 |
| 3,480,785 A | 11/1969 | Aufderheide | 250/219 |
| 3,496,370 A | 2/1970 | Haville et al. | 250/219 |

(Continued)

FOREIGN PATENT DOCUMENTS

| | | |
|---|---|---|
| DE | 2 659 929 | 7/1977 |
| DE | 2 760 269 | 7/1977 |
| DE | 2659929 C3 | 11/1977 |
| DE | 2935668 C2 | 9/1979 |
| DE | 2 935 668 | 5/1980 |

(Continued)

OTHER PUBLICATIONS

Glory UW-200 Multipurpose Compact Currency Sorter, 4 pages, ©1999.
Glory UW-100 Compact Currency Fitness Sorter, 2 pages, ©1999.
Glory GFU-100 Desk-Top Currency Fitness Sorter/Counter, 1 pages, Nov. 11, 1994.

(Continued)

*Primary Examiner*—Donald P. Walsh
*Assistant Examiner*—Mark J. Beauchaine
(74) *Attorney, Agent, or Firm*—Jenkens & Gilchrist

(57) ABSTRACT

A currency evaluation device for receiving a stack of currency bills and rapidly evaluating all the bills in the stack. The device comprises an input receptacle for receiving a stack of bills to be evaluated and a plurality of output receptacles for receiving the bills after they have been evaluated. A transport mechanism transports the bills, one at a time, from the input receptacle to one of the output receptacles along a transport path. A discriminating unit including a detector positioned along the transport path between the input receptacle and the output receptacle evaluates the bills. The discriminating unit counts and determines the denomination of the bills. A means for flagging bills meeting or failing to meet a certain criteria causes the transport mechanism to halt in response to a determination that a bill meets or fails to meet the criteria.

78 Claims, 43 Drawing Sheets

U.S. PATENT DOCUMENTS

| | | | |
|---|---|---|---|
| 3,509,535 A | 4/1970 | Berube | 340/149 |
| 3,612,835 A | 10/1971 | Andrews et al. | 235/61.11 D |
| 3,679,314 A | 7/1972 | Mustert | 356/71 |
| 3,759,382 A * | 9/1973 | Walkley et al. | 209/111.7 |
| 3,778,628 A | 12/1973 | Novak et al. | 250/556 |
| 3,870,629 A | 3/1975 | Carter et al. | 209/111.8 |
| 3,906,449 A | 9/1975 | Marchak | 340/149 R |
| 3,952,183 A | 4/1976 | Abe | 235/92 SB |
| 3,976,198 A | 8/1976 | Carnes et al. | 209/111.7 T |
| 4,041,456 A | 8/1977 | Ott et al. | 340/146.3 R |
| 4,096,991 A | 6/1978 | Iquchi | 235/419 |
| 4,114,804 A | 9/1978 | Jones et al. | 235/476 |
| 4,147,430 A | 4/1979 | Gorgone et al. | 356/51 |
| 4,166,945 A | 9/1979 | Inoyama et al. | 235/379 |
| 4,179,685 A * | 12/1979 | O'Maley | 340/146.3 H |
| 4,243,216 A | 1/1981 | McInerny | 271/122 |
| 4,255,651 A | 3/1981 | Phillips | 235/92 |
| 4,275,874 A | 6/1981 | DiBlasio | 271/187 |
| 4,283,708 A | 8/1981 | Lee | 340/146.3 Z |
| 4,288,781 A | 9/1981 | Sellner et al. | 340/146.3 Q |
| 4,302,781 A | 11/1981 | Ikeda et al. | 358/486 |
| 4,311,914 A | 1/1982 | Huber | 250/556 |
| 4,334,619 A | 6/1982 | Horino et al. | 209/551 |
| 4,348,656 A | 9/1982 | Gorgone et al. | 340/146.3 R |
| 4,349,111 A | 9/1982 | Shah et al. | 209/534 |
| 4,355,300 A | 10/1982 | Weber | 340/146.3 C |
| 4,356,473 A | 10/1982 | Freudenthal | 340/146.3 H |
| 4,381,447 A | 4/1983 | Horvath et al. | 250/223 |
| 4,386,432 A | 5/1983 | Nakamura et al. | 382/7 |
| 4,416,449 A | 11/1983 | McInerny | 271/122 |
| 4,420,153 A | 12/1983 | Winkler et al. | 271/304 |
| 4,442,541 A | 4/1984 | Finkel et al. | 382/7 |
| 4,461,028 A | 7/1984 | Okubo | 382/15 |
| 4,464,786 A | 8/1984 | Nishito et al. | 382/7 |
| 4,464,787 A | 8/1984 | Fish et al. | 382/7 |
| 4,470,496 A | 9/1984 | Steiner | 194/4 |
| 4,487,306 A | 12/1984 | Nao et al. | 382/135 |
| 4,490,846 A | 12/1984 | Ishida et al. | 382/7 |
| 4,513,439 A | 4/1985 | Gorgone et al. | 382/7 |
| 4,532,641 A | 7/1985 | Nishimura | 377/14 |
| 4,539,702 A | 9/1985 | Oka | 382/7 |
| 4,542,829 A | 9/1985 | Emery et al. | 209/534 |
| 4,547,896 A | 10/1985 | Ohtombe et al. | 382/318 |
| 4,556,140 A | 12/1985 | Okada | 194/4 |
| 4,559,452 A | 12/1985 | Igaki et al. | 250/560 |
| 4,563,771 A | 1/1986 | Gorgone et al. | 382/7 |
| 4,587,412 A | 5/1986 | Apisdorf | 235/449 |
| 4,587,434 A | 5/1986 | Roes et al. | 250/556 |
| 4,588,292 A | 5/1986 | Collins | 356/71 |
| 4,592,090 A | 5/1986 | Curl et al. | 382/7 |
| 4,628,194 A | 12/1986 | Dobbins et al. | 235/379 |
| 4,645,936 A | 2/1987 | Gorgone | 250/556 |
| 4,653,647 A | 3/1987 | Hashimoto | 209/534 |
| 4,677,682 A | 6/1987 | Miyaqawa et al. | 382/7 |
| 4,681,229 A | 7/1987 | Uesaka et al. | 209/534 |
| 4,694,963 A | 9/1987 | Takesako | 209/534 |
| 4,697,071 A | 9/1987 | Hiraoka et al. | 235/379 |
| 4,700,368 A | 10/1987 | Munn et al. | 377/8 |
| 4,707,843 A | 11/1987 | McDonald | 377/8 |
| 4,733,308 A | 3/1988 | Nakamura et al. | 358/496 |
| 4,747,492 A | 5/1988 | Saito et al. | 209/534 |
| 4,761,002 A | 8/1988 | Reed et al. | 271/111 |
| 4,764,725 A | 8/1988 | Bryce | 324/234 |
| 4,787,518 A | 11/1988 | Yuge et al. | 209/534 |
| 4,823,393 A | 4/1989 | Kawakami | 382/7 |
| 4,827,531 A | 5/1989 | Milford | 382/7 |
| 4,850,468 A | 7/1989 | Kobayashi et al. | 194/207 |
| 4,881,268 A | 11/1989 | Uchida et al. | 382/7 |
| 4,973,851 A | 11/1990 | Lee | 250/556 |
| 4,996,604 A | 2/1991 | Oqawa et al. | 358/486 |
| 5,047,871 A | 9/1991 | Meyer et al. | 358/486 |
| 5,051,900 A | 9/1991 | Ito et al. | 364/408 |
| 5,068,519 A | 11/1991 | Bryce | 235/449 |
| 5,076,441 A | 12/1991 | Gerlier | 209/534 |
| 5,163,672 A | 11/1992 | Mennie | 271/187 |
| 5,167,411 A | 12/1992 | Isobe | 271/273 |
| 5,201,395 A | 4/1993 | Takizawa et al. | 194/205 |
| 5,207,788 A | 5/1993 | Geib | 271/122 |
| 5,230,653 A | 7/1993 | Shinozaki et al. | 453/4 |
| 5,236,072 A | 8/1993 | Cargill | 194/207 |
| 5,242,041 A | 9/1993 | Isobe | 194/207 |
| 5,259,490 A | 11/1993 | Gardellini | 194/203 |
| 5,295,196 A | 3/1994 | Raterman et al. | 382/7 |
| 5,301,786 A | 4/1994 | Yoshihara | 194/207 |
| 5,304,813 A | 4/1994 | De Man | 250/556 |
| 5,394,992 A * | 3/1995 | Winkler | 209/552 |
| 5,402,895 A * | 4/1995 | Mikkelsen et al. | 209/534 |
| 5,419,423 A | 5/1995 | Ishida et al. | 194/206 |
| 5,421,443 A | 6/1995 | Hatamachi et al. | 194/206 |
| 5,430,664 A | 7/1995 | Cargill et al. | 364/550 |
| 5,465,821 A | 11/1995 | Akioka | 194/207 |
| 5,467,405 A | 11/1995 | Raterman et al. | 382/135 |
| 5,467,406 A | 11/1995 | Graves et al. | 382/135 |
| D369,984 S | 5/1996 | Larsen | D10/97 |
| 5,577,589 A | 11/1996 | Garcia Tinoco | 194/204 |
| 5,633,949 A | 5/1997 | Graves et al. | 382/135 |
| 5,640,463 A | 6/1997 | Csulits | 382/135 |
| 5,652,802 A | 7/1997 | Graves et al. | 382/135 |
| 5,687,963 A | 11/1997 | Mennie | 271/119 |
| 5,692,067 A | 11/1997 | Raterman et al. | 382/135 |
| 5,704,491 A | 1/1998 | Graves | 209/534 |
| 5,724,438 A | 3/1998 | Graves | 382/135 |
| 5,751,840 A | 5/1998 | Raterman et al. | 382/135 |
| 5,761,089 A | 6/1998 | McInerny | 364/550 |
| 5,790,693 A | 8/1998 | Graves et al. | 382/135 |
| 5,790,697 A | 8/1998 | Jones et al. | 382/135 |
| 5,806,650 A | 9/1998 | Mennie et al. | 194/206 |
| 5,815,592 A | 9/1998 | Mennie et l. | 382/135 |
| 5,822,448 A | 10/1998 | Graves et al. | 382/135 |
| 5,832,104 A | 11/1998 | Graves et al | 382/135 |
| 5,867,589 A | 2/1999 | Graves et al. | 382/135 |
| 5,870,487 A | 2/1999 | Graves et al. | 382/135 |
| 5,875,259 A | 2/1999 | Mennie et al. | 382/135 |
| 5,905,810 A | 5/1999 | Jones et al. | 382/135 |
| 5,909,502 A | 6/1999 | Mazur | 382/135 |
| 5,909,503 A | 6/1999 | Graves et al. | 382/135 |
| 5,915,518 A | 6/1999 | Hopwood et al. | 194/207 |
| 5,938,044 A | 8/1999 | Weggesser | 209/534 |
| 5,940,623 A | 8/1999 | Watts et al. | 395/712 |
| 5,943,655 A | 8/1999 | Jacobson | 705/30 |
| 5,960,103 A | 9/1999 | Graves et al. | 382/135 |
| 5,966,456 A | 10/1999 | Jones et al. | 382/135 |
| 5,975,273 A | 11/1999 | Zwahlen et al. | 194/206 |
| 5,982,918 A | 11/1999 | Mennie et al. | 382/135 |
| 5,992,601 A | 11/1999 | Mennie et al. | 382/135 |
| 6,012,564 A | 1/2000 | Mukai | 194/206 |
| 6,012,565 A | 1/2000 | Mazur | 194/207 |
| 6,026,175 A | 2/2000 | Raterman et al. | 382/135 |
| 6,028,951 A | 2/2000 | Raterman et al. | 382/135 |
| 6,039,645 A | 3/2000 | Mazur | 453/10 |
| 6,068,194 A | 5/2000 | Mazur | 235/492 |
| 6,072,896 A | 6/2000 | Graves et al. | 382/135 |
| 6,073,744 A | 6/2000 | Raterman et al. | 194/207 |
| 6,074,334 A | 6/2000 | Mennie et al. | 493/438 |
| 6,220,419 B1 | 4/2001 | Mennie | 194/207 |
| 6,234,294 B1 | 5/2001 | Defeo et al. | 194/207 |
| 6,237,739 B1 | 5/2001 | Mazur et al. | 194/207 |
| 6,241,069 B1 | 6/2001 | Mazur et al. | 194/207 |
| 6,278,795 B1 | 8/2001 | Anderson et al. | 382/135 |
| 6,311,819 B1 | 11/2001 | Stromme et al. | 194/207 |
| 6,398,000 B1 | 6/2002 | Jenrick et al. | 194/200 |

| | | | |
|---|---|---|---|
| 6,459,806 B1 | 10/2002 | Raterman et al. ............ | 382/135 |
| 6,460,705 B1 | 10/2002 | Hallowell .................... | 209/534 |
| 6,493,461 B1 | 12/2002 | Mennie et al. ............... | 382/135 |
| 6,539,104 B1 | 3/2003 | Raterman et al. ............ | 382/135 |
| 6,560,355 B2 | 5/2003 | Graves et al. ............... | 382/135 |
| 2001/0019624 A1 | 9/2001 | Rateman et al. ............. | 382/135 |
| 2002/0001393 A1 | 1/2002 | Jones et al. .................. | 382/100 |
| 2002/0020603 A1 | 2/2002 | Jones et al. .................. | 194/346 |
| 2002/0056605 A1 | 5/2002 | Mazur et al. ................ | 194/207 |
| 2002/0085245 A1 | 7/2002 | Mennie et al. ............... | 358/498 |
| 2002/0085745 A1 | 7/2002 | Jones et al. .................. | 382/135 |
| 2002/0103757 A1 | 8/2002 | Jones et al. .................... | 705/45 |
| 2002/0104785 A1 | 8/2002 | Klein et al. .................. | 209/534 |
| 2002/0107801 A1 | 8/2002 | Jones et al. .................... | 705/45 |
| 2002/0118871 A1 | 8/2002 | Jones et al. .................. | 382/137 |
| 2002/0122580 A1 | 9/2002 | Jones et al. .................. | 382/137 |
| 2002/0126885 A1 | 9/2002 | Mennie et al. ............... | 382/135 |
| 2002/0126886 A1 | 9/2002 | Jones et al. .................. | 382/135 |
| 2002/0131630 A1 | 9/2002 | Jones et al. .................. | 382/135 |
| 2002/0136442 A1 | 9/2002 | Jones et al. .................. | 382/135 |
| 2002/0145035 A1 | 10/2002 | Jones .......................... | 235/379 |
| 2002/0154804 A1 | 10/2002 | Jones et al. .................. | 382/135 |
| 2002/0154805 A1 | 10/2002 | Jones et al. .................. | 382/135 |
| 2002/0154806 A1 | 10/2002 | Jones et al. .................. | 382/135 |
| 2002/0154807 A1 | 10/2002 | Jones et al. .................. | 382/135 |
| 2002/0154808 A1 | 10/2002 | Jones et al. .................. | 382/135 |
| 2003/0009420 A1 | 1/2003 | Jones .......................... | 705/39 |
| 2003/0015395 A1 | 1/2003 | Hallowell et al. ........... | 194/206 |
| 2003/0015396 A1 | 1/2003 | Mennie ....................... | 194/206 |
| 2003/0062242 A1 | 4/2003 | Hallowell et al. ........... | 194/302 |

FOREIGN PATENT DOCUMENTS

| | | |
|---|---|---|
| EP | 0077464 A2 | 9/1982 |
| EP | 0077464 | 4/1983 |
| EP | 0130824 A2 | 6/1984 |
| EP | 0130824 A2 | 6/1984 |
| EP | 0130825 A2 | 6/1984 |
| EP | 0130825 A2 | 6/1984 |
| EP | 0132329 A2 | 6/1984 |
| EP | 0132329 A2 | 6/1984 |
| EP | 0206675 B1 | 6/1986 |
| EP | 0206675 B1 | 6/1986 |
| EP | 0253935 A2 | 10/1986 |
| EP | 0253935 A2 | 10/1986 |
| EP | 0264125 A1 | 10/1987 |
| EP | 0264125 A1 | 10/1987 |
| EP | 0338123 A2 | 11/1988 |
| EP | 0342547 A2 | 5/1989 |
| EP | 0338123 | 10/1989 |
| EP | 0342647 | 11/1989 |
| EP | 0613107 A1 | 8/1994 |
| GB | 2061232 A | 5/1981 |
| GB | 2061232 A | 5/1981 |
| GB | 2088832 | 6/1982 |
| GB | 2019138 A | 11/1983 |
| GB | 2119138 A | 11/1983 |
| GB | 2204166 A | 11/1988 |
| JP | 54-60999 | 6/1979 |
| JP | 54-71673 | 6/1979 |
| JP | 54-71674 | 6/1979 |
| JP | 55-52538 | 12/1980 |
| JP | 56-16287 | 2/1981 |
| JP | 56-136689 | 10/1981 |
| JP | 58-139296 | 8/1983 |
| JP | 59-186079 | 10/1984 |
| JP | 59-231692 | 12/1984 |
| JP | 60-191379 | 9/1985 |
| JP | 60-215293 | 11/1985 |
| JP | 61-14557 | 4/1986 |
| JP | 61-82290 | 4/1986 |
| JP | 61-41439 | 9/1986 |
| JP | 62-220843 | 9/1987 |
| JP | 63-91794 | 4/1988 |
| JP | 63-271687 | 11/1988 |
| JP | 63-276688 | 11/1988 |
| JP | 2-22786 | 1/1990 |
| JP | 2-12492 | 2/1990 |
| JP | 5-11355 | 7/1993 |
| WO | WO 81/02111 | 4/1981 |
| WO | WO 91/11778 | 8/1991 |
| WO | WO 92/17394 | 10/1992 |
| WO | WO 93/23824 | 11/1993 |
| WO | WO 95/24691 | 9/1995 |
| WO | WO 96/10800 | 4/1996 |

OTHER PUBLICATIONS

Glory GFRT–1 Currency Scanner, 12/94.

Glory GFR–100 Currency Reader Counter Instruction Manual, 32 pages, Aug. 20, 1998.

Glory Brochure "Unstoppable" GFR–100 ReadMaster Currency Discriminator, 2 pages, 8/98.

Glory Brochure "Tank Tough Currency Discriminators" GFR–100 & GFB–700, 2 pages, Aug. 6, 1998.

Glory Brochure "Tank Tough Currency Discriminators" GFR–100 & GFR–S800, 2 pages, Dec. 7, 1999.

Mosler Inc, Brochure "The Mosler/Toshiba CF–420", 1989.

JetScan Currency Scanner/Counter, Model 4060, Operator's Manual by Cummins–Allison (8/91).

Sale of JetScan Currency Scanner/Counter, Model 4060 (8/91).

JetScan Currency Scanner/Counter, Model 4061, Operating Instructions by Cummin–Allison (Apr. 20, 1993).

Sale of JetScan Currency Scanner/Counter, Model 4061 (Apr. 20, 1993).

AFB Currency Recognition System (1982).

Description of Toshiba–Mosler CF–420 Device; estimated 1989.

Toshiba–Mosler Operator's Manual for CF–420 Cash Settlement System; pp. 10 to C–3; Copyr. 1989.

Chp. 7 of Mosler CF–420 Cash Management System, Operator's Manual©, 1989.

Currency Systems International, Medium Speed Currency Sorting Family, SPS 600 and CPS 900; 4 pages; date: copyr. 1994.

Currency System Intl'l, Mr. W. Kranister in Conversation With Richard Haycock; pp. 1–5; dated: estimated 1994.

Description of Currency Systems International's CPS 600 and CPS 900 devices; date: estimated 1994.

Currency Systems International/Currency Processing Systems, CPS 300; 4 pages; date copyr. 1992

Currency Systems International/Currency Processing Systems, CPS 300; 4 pages; date: uncertain.

Glory UF–ID brochure; 2 pages; date: estimated before Aug. 9, 1994.

Glory GFB–200/210/220/230, Desk–Top Bank Note Counter; 2 pages; date: estimated before Aug. 9, 1994.

Revised Drawings of portions of Mosler CF–420 Cash management system (FIGs. A–C) and description of the same (1989).

Brochure: "GFR–X Banknote Counter with Denomination Recognition", date: 12,94; pp. 3.

Glory Instruction Manual for Model GFR–100 Currency Reader Counter, dated Aug. 15, 1995; pp. 26.

Declaration of Per Torling, 6 page (Mar. 18, 1999).

First Translation of JP 61–14557.

Second Translations of 61–14557 (Glory).

Translation of JP 54–71673.
Translation of JP 54–71674.
Translation of JP 61–41439.
First Translation of JP 56–136689.
Second Translation of JP 56–136689 (Glory).
Billcon D–202/204 Service Manual (Cover marked 630229) (Japanese).
Translation of Billcon D–202/204 Service Manual—(C29).
Billcon D–202, D204 Operator's Manual (cover marked 611215) (Japanese).
First Translation of Billcon D–202, D204 Operator's Manual (C31).
Second Translation of Billcon D–202 Operator's Manual (C31) (Glory).
Banking Machine Digest No. 31 (last page of C35 translation has a date of Dec. 5, 1988) (Japanese).
First Translation of Banking Machine Digest No. 31 (C34).
Second Translation of Banking Machine Digest No. 31 (C34) (Glory).
Third Translation of Banking Machine Digest No. 31 (C34).
Cummins–Allison Corp. v. Glory U.S.A., Inc., N.D. Ill. 1998.
JP Banking Machine Digest, No. 31, 1989—Digest and Translation.
Operation Manual of the D–202, D–204 Mixed Paper Currency Counter of Billcon, Co., Ltd—Translation.
Service Manual of the D–202, D204 Mixed Paper Currency Counter of Billcon Co., Ltd.—Translation.
Translation of JP–71673.
Translation of JP 56–16287.
Bilicon: 38$^{th}$ Banking Uniform Show (1 page) and translation (2 pages) (1998).
Billcon: D212 –Odd Bill Detecting Bill Counter –Instruction Manual, 17 pages, Japanese and translation (p. 17 dated 1994).
Billcon: D212 Note Counter, 4 pages –Japanese and Translation (undated).
De La Rue Systems Currency Sorting Machines With Pattern Recognition: 3120 User Guide, 2 pages (1987).
De La Rue Systems Limited Use Of The Diagnostics Function 3110 Mk.II/312D Machines 10 pages (printed Jan. 30, 2003).
De La Rue Systems: 2700VB brochure, 1 page (Dec. 9, 1996).
De La Rue Systems: 3100 Series Operator Instruction Manual, (52 pages) printed Jan. 20, 2003.
De La Rue: 2700 Currency Counting Machine –User Guide, Revision 1, 53 pages (Aug. 26, 1999).
G&D: CHP 50 User's Guide, 61 pages (Mar. 1998).
Geldinstitute (1983) (2 pages) (printed Jan. 24, 2003).
Geldinstitute (1983) (translation of above) (2003) –3 pages.
Glory: GFB 700 Bank Note Counting Machine–Operating Instructions, 32 pages (Sep. 1998).
Glory: GSA–500 –Instruction Manual, 40 pages (prior to Jul. 1998).
Glory: GSA–500 –Operating Procedures, 9 pages (prior to Jul. 1998).
Japanese Reference X and Statement of Relevance (2002) – 11 pages.
JCM: BC–30 Bill Counter, 2 pages (date unknown, prior to Aug. 2002).
JCM: DBC–3 U.S. Dollar Bank Note Checker, 2 pages (date unknown, prior to Aug. 2002).
JP Banking Machine Digest, No. 31, 1989–Digest and Translation.
Mosler/Toshiba: Model CS–6600 Currency Handler brochure–"Let Mosler Help You Cut Costs Four Ways," 4 pages (®1993).
Mosler/Toshiba: Model CS–6600 Currency Handler brochure–"Let Mosler Help You Cut Costs Four Ways," 4 pages (©1993).
Musashi Co.: Operation Manual for Maintenance and Learning Modes for Tellac–5, 5DD, SD, DDA, A & SSD, 13 pages (prior Aug. 2002).
Operation Manual of the D–202, D–204 Mixed Paper Currency Counter of Billcon, Co., Ltd. –Translation (undated).
Service Manual of the D–202, D–204 Mixed Paper Currency Counter of Billcon Co., Ltd. –Translation (undated).
Toshiba: CF–400 Series Fitness Sorter, 6 pages (estimated 1989 or earlier).
Translation of DE 2659929 (undated).
Translation of DE 2760269 (undated).
Translation of DE 2935668 (undated).
Translation of EP 0077464 A2 (undated).
Translation of EP 0342647 A2 (undated).
Translation of JP 2–12492 (undated).
Translation of JP 54–60999 (undated).
Translation of JP 55–52538 (undated).
Translation of JP 56–16287 (undated).
Translation of JP 60–215293 (undated).
Translation of JP 62–220843 (undated).
Translation of JP 63–271687 (undated).
Translation of JP 63–276688 (undated).
Glory GFB–30 brochure (2 pages) (date unknown, prior to Nov. 20, 2002) (Japanese) [Nov. 19, 2002 Mouri Ex. 3].*
Billcon D–202/204 Service Manual–Second Translation (Glory) (cover marked 630229) (25 pages) [Nov. 15, 2002 Hoyo Ex. 2a].*

* cited by examiner

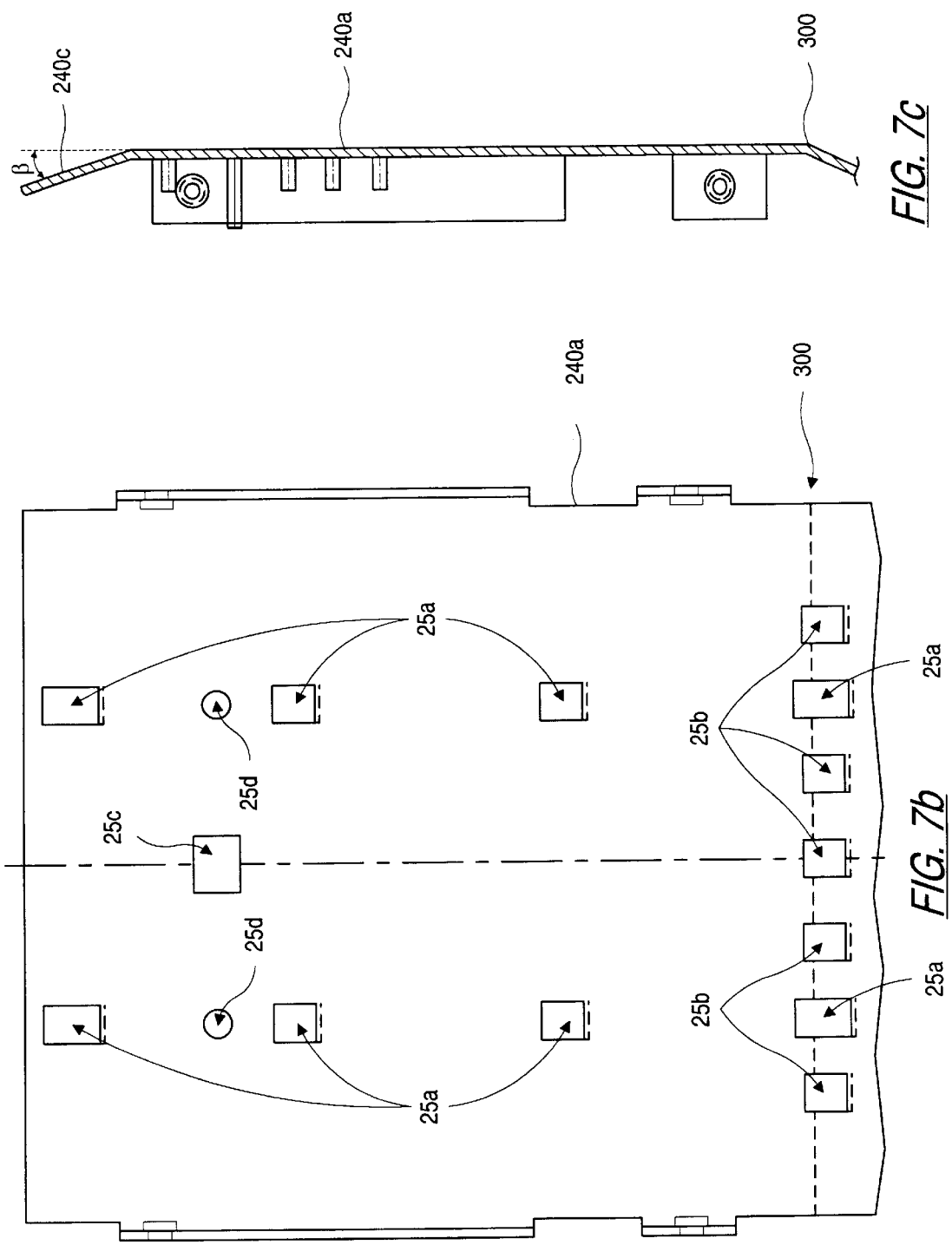

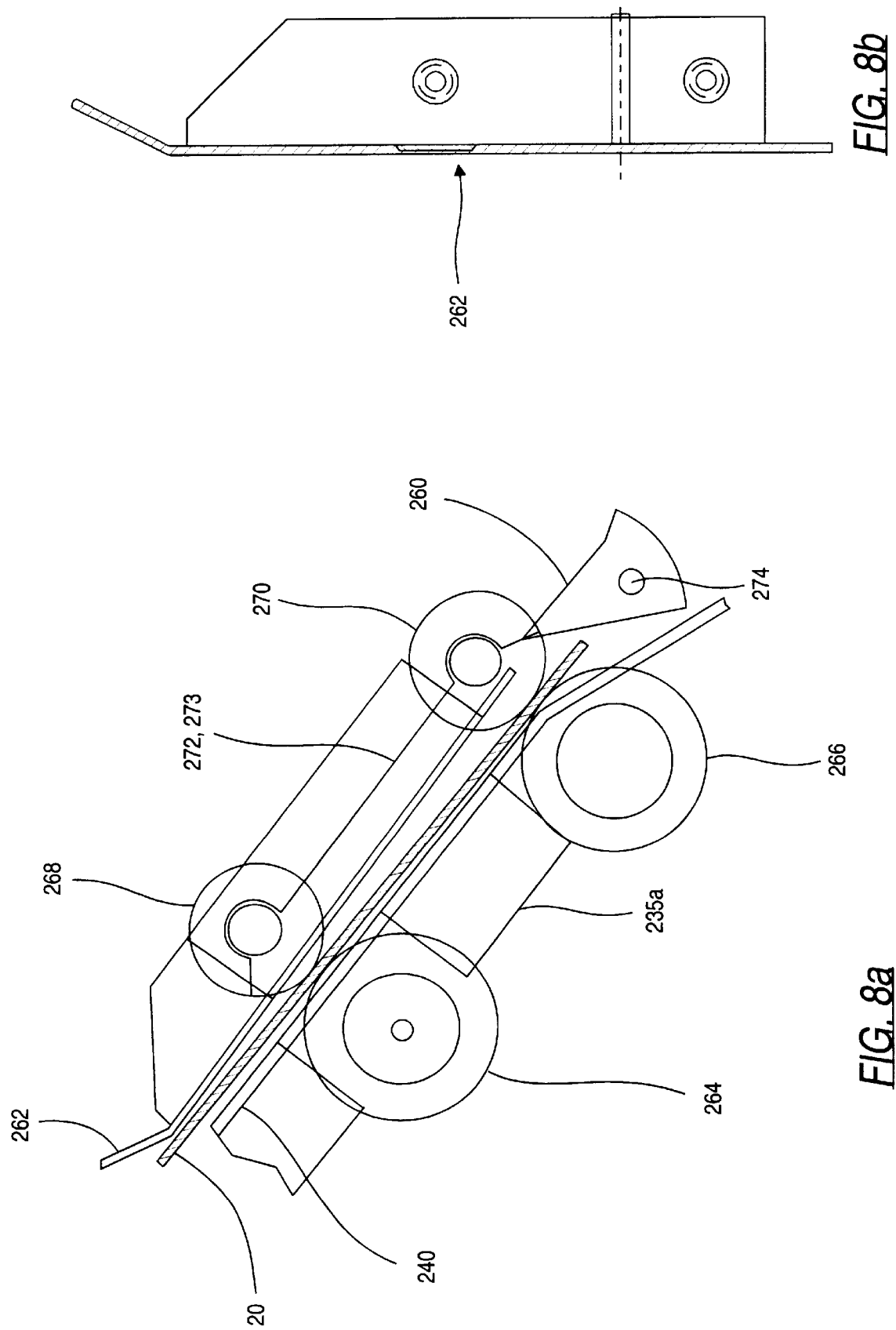

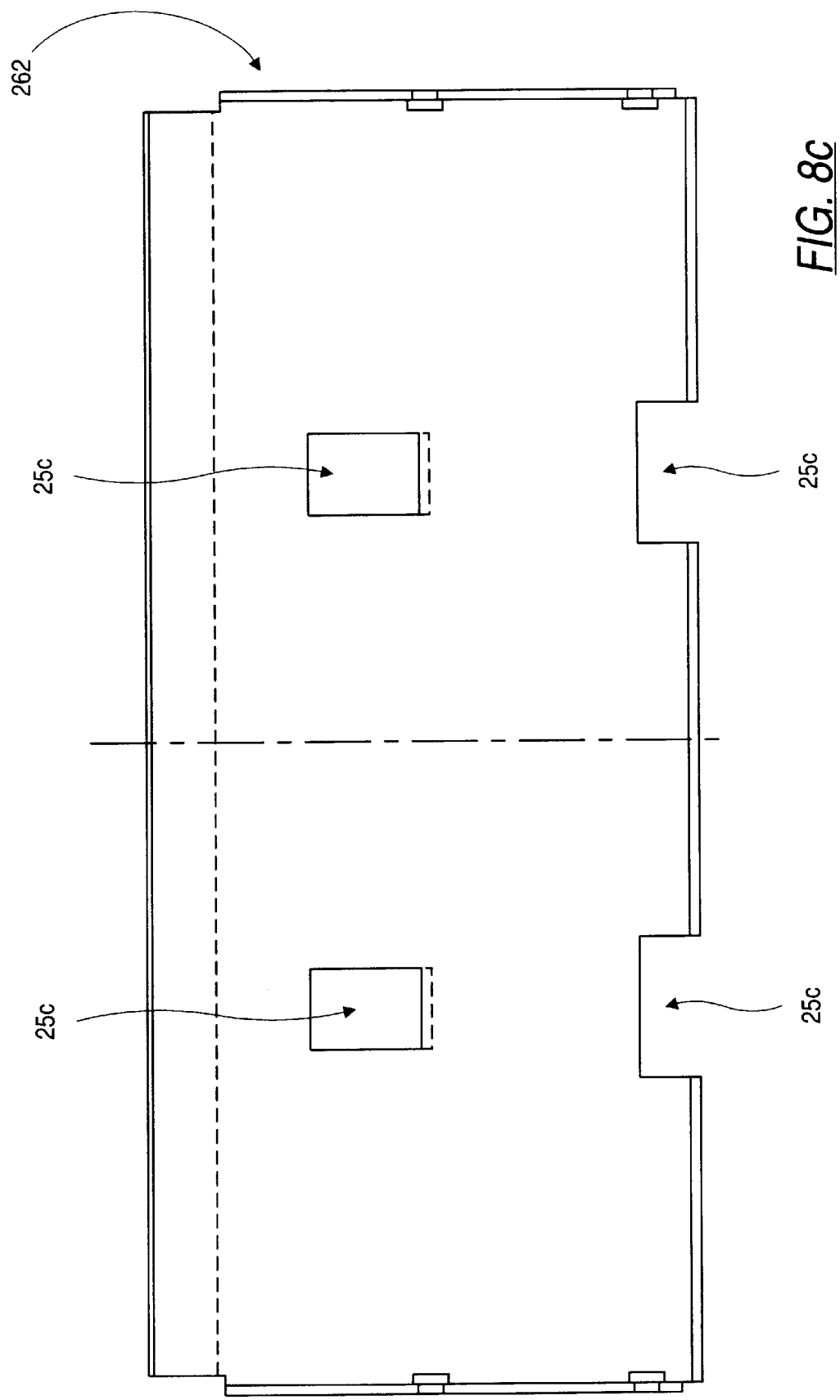

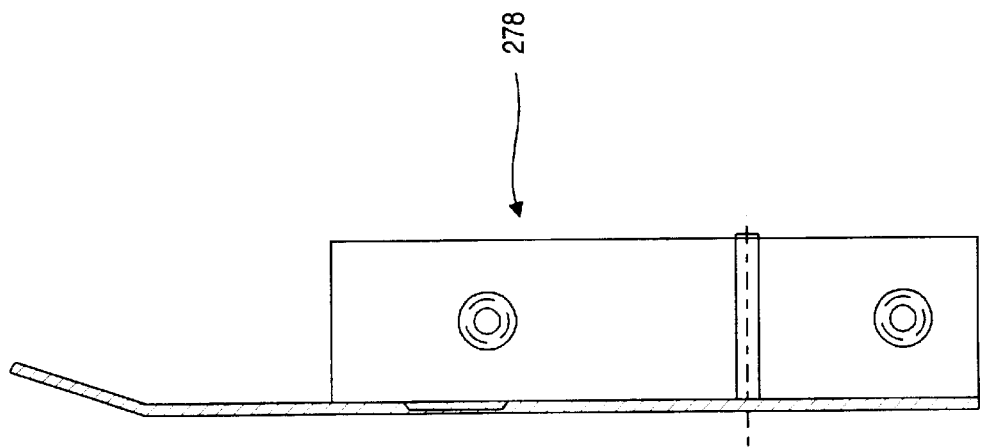
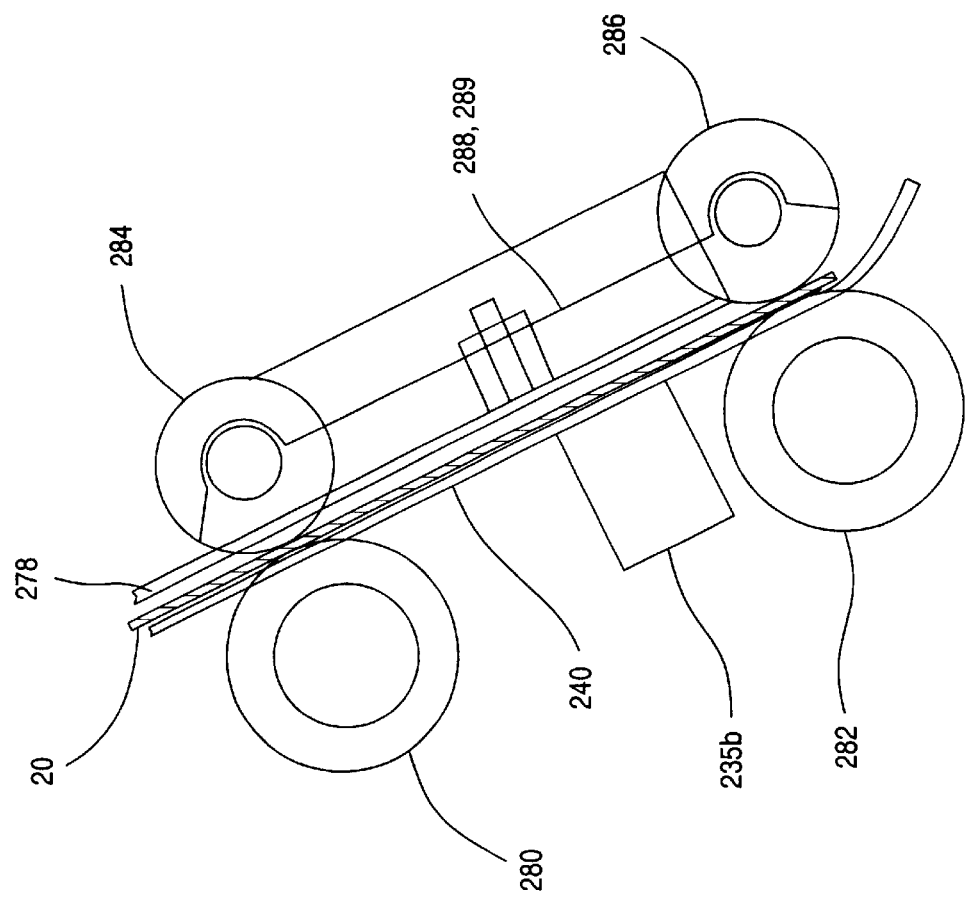

|  |  | BATCH | TOTALS |  | 810 |
|---|---|---|---|---|---|
| DENOM<br>$ 1<br>$ 5 |  | COUNT<br>57<br>100 |  | VALUE<br>$ 57<br>$ 500 |  |
| $ 10<br>$ 20<br>$ 50 |  | 3<br>50<br>200 |  | $ 30<br>$ 1000<br>$ 10000 |  |
| $ 100<br>TOTAL |  | 303 |  | $ 30300<br>$ 41887 | CLEAR |
|  |  |  |  |  | EXIT |

| DENOM<br>$ 1<br>$ 2 | UNIT<br>22<br>28 | LIMIT<br>100<br>100 |  |  |  |
|---|---|---|---|---|---|
| ~~$ 5~~ | ~~38~~ | ~~100~~ |  |  |  |
| $ 10<br>$ 20<br>$ 50<br>$ 100 | 26<br>36<br>32<br>30 | 50<br>50<br>50<br>50 |  | DOWN | UP |
|  |  |  |  | CLEAR | ALL |
| 5 | 10 | 20 | 25 | + | UNIT |
| 50 | 75 | 100 | OFF | - | EXIT |

| STRAP | LIMIT | POCKET | 1 | | |
|---|---|---|---|---|---|
| REMOVE | NOTES | AND | PRESS | CONT. | |
| | | | | | |
| | | CONT | | | |
| | | | | | |

| NO | CALL | PRESS | KEY: | | |
|---|---|---|---|---|---|
| | | | | | |
| $ 1 | $ 2 | $ 5 | $ 10 | $ 20 | $ 50 |
| $ 100 | | | | | |
| | | | | | CONT. |

Figures 31, 32:
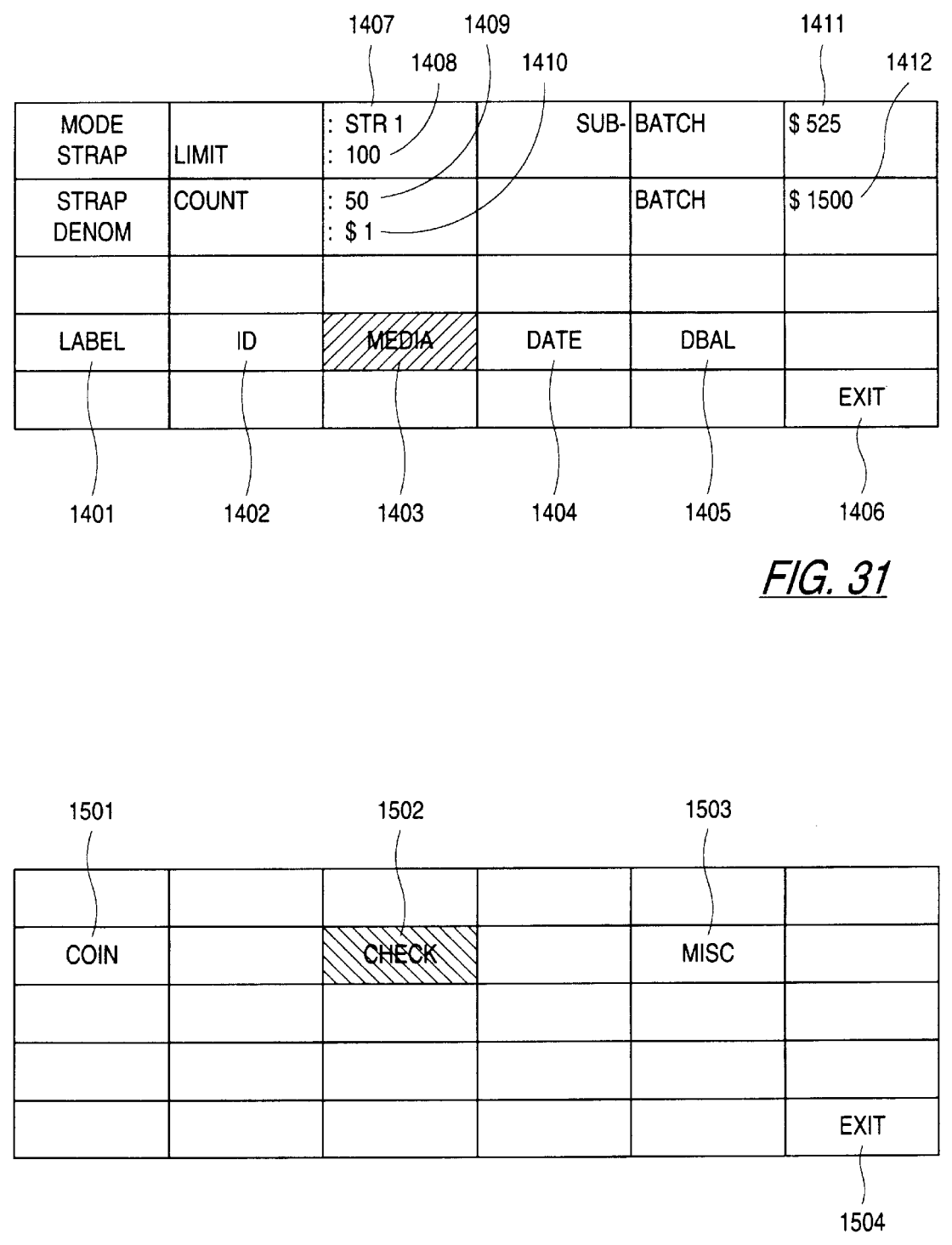

| MODE STRAP | LIMIT | : STR 1 : 100 | SUB- | BATCH | $ 525 |
|---|---|---|---|---|---|
| STRAP DENOM | COUNT | : 50 : $ 1 | | BATCH | $ 1500 |
| | | | | | |
| LABEL | ID | ///MEDIA/// | DATE | DBAL | |
| | | | | | EXIT |

| | | | | | |
|---|---|---|---|---|---|
| COIN | | ///CHECK/// | | MISC | |
| | | | | | |
| | | | | | |
| | | | | | EXIT |

MODE: _____

|  | SELECTION | OPTIONS |
|---|---|---|
| TARGET 1 (POCKET 1) | | |
| R1 — DENOM. ? | | OFF / 1st BILL / US / ALL<br>$1 / $2 / $5 / $10 / $20 / $50 / $100 |
| R2 — FACE ? | | OFF / 1st BILL / FACE UP / FACE DOWN / US |
| R3 — ORIENTATION ? | | OFF / 1st BILL / FORWARD / REVERSE / US |
| R4 — SERIES ? | | OFF / 1st BILL / DEFINED - GROUPS / US |
| R5 — UPDATE ? | | YES / NO |
| TARGET 2 (POCKET 2) | | |
| R6 — DENOM. ? | | OFF / 1st BILL / US / ALL<br>$1 / $2 / $5 / $10 / $20 / $50 / $100 |
| R7 — FACE ? | | OFF / 1st BILL / FACE UP / FACE DOWN / US |
| R8 — ORIENTATION ? | | OFF / 1st BILL / FORWARD / REVERSE / US |
| R9 — SERIES ? | | OFF / 1st BILL / DEFINED - GROUPS / US |
| R10 — UPDATE ? | | YES / NO |
| R11 — STRANGER (S) | | P1 / P2 / CONT - 2 / ST |
| R12 — DENOM CHANGE (DC) | | P1 / P2 / CONT - 2 / ST |
| R13 — NO CALL (NC) | | P1 / P2 / CONT - 2 |
| R14 — SUSPECT DOC. (SD) | | P1 / P2 / CONT - 2 |
| R15 — IMPROPER SIZE (SZ) | | P1 / P2 / CONT - 2 |
| R16 — UNFIT DOC. (UD) | | P1 / P2 / CONT - 2 |
| R17 — REVERSE FACED (RF) | | P1 / P2 / CONT - 2 |
| R18 — REV. ORIENTED (RO) | | P1 / P2 / CONT - 2 |
| R19 — SEP. SERIES (SS) | | P1 / P2 / CONT - 2 / ST |
| R20 — STACKER FULL (SF) | | STOP / SWITCH |
| R21 — STRAP LIMIT (SL) | | STOP / SWITCH / COMBINE P1 + P2 |
| R22 — CHAIN (C) | | STOP - 1 / STOP - 2 |
| R23 — DOUBLE (D) | | STOP - 1 / STOP - 2 |

*FIG. 35*

MODE: STRANGER FACING

|  | | SELECTION | OPTIONS |
|---|---|---|---|
| | TARGET 1 (POCKET 1) | | |
| R1 | DENOM. ? | 1st BILL | ~~OFF /~~ 1st BILL / US / ALL $1 / $2 / $5 / $10 / $20 / $50 / $100 |
| R2 | FACE ? | 1st BILL | ~~OFF /~~ 1st BILL / FACE UP / FACE DOWN / US |
| R3 | ORIENTATION ? | OFF | OFF / 1st BILL / FORWARD / REVERSE / US |
| R4 | SERIES ? | OFF | OFF / 1st BILL / DEFINED - GROUPS / US |
| R5 | UPDATE ? | NO | YES / NO |
| | TARGET 2 (POCKET 2) | | |
| R6 | DENOM. ? | — | ~~OFF / 1st BILL / US / ALL $1 / $2 / $5 / $10 / $20 / $50 / $100~~ |
| R7 | FACE ? | — | ~~OFF / 1st BILL / FACE UP / FACE DOWN / US~~ |
| R8 | ORIENTATION ? | — | ~~OFF / 1st BILL / FORWARD / REVERSE / US~~ |
| R9 | SERIES ? | — | ~~OFF / 1st BILL / DEFINED - GROUPS / US~~ |
| R10 | UPDATE ? | — | ~~YES / NO~~ |
| | | | |
| R11 | STRANGER (S) | P2 | P1 / P2 / CONT - 2 / ST |
| R12 | DENOM CHANGE (DC) | — | ~~P1 / P2 / CONT - 2 / ST~~ |
| R13 | NO CALL (NC) | P2 | P1 / P2 / CONT - 2 |
| R14 | SUSPECT DOC. (SD) | P2 | P1 / P2 / CONT - 2 |
| R15 | IMPROPER SIZE (SZ) | P2 | P1 / P2 / CONT - 2 |
| R16 | UNFIT DOC. (UD) | P2 | P1 / P2 / CONT - 2 |
| R17 | REVERSE FACED (RF) | C2 | P1 / P2 / CONT - 2 |
| R18 | REV. ORIENTED (RO) | — | ~~P1 / P2 / CONT - 2~~ |
| R19 | SEP. SERIES (SS) | — | ~~P1 / P2 / CONT - 2 / ST~~ |
| | | | |
| R20 | STACKER FULL (SF) | STOP | STOP / SWITCH |
| R21 | STRAP LIMIT (SL) | COMBINE | STOP / SWITCH / COMBINE P1 + P2 |
| R22 | CHAIN (C) | STOP - 2 | STOP - 1 / STOP - 2 |
| R23 | DOUBLE (D) | STOP - 2 | STOP - 1 / STOP - 2 |

*FIG. 36*

MODE: SORT 3

| | | SELECTION | OPTIONS |
|---|---|---|---|
| | TARGET 1 (POCKET 1) | | |
| R1 | DENOM. ? | $5 | ~~OFF~~ / 1st BILL / US / ALL $1 / $2 / $5 / $10 / $20 / $50 / $100 |
| R2 | FACE ? | OFF | OFF / 1st BILL / FACE UP / FACE DOWN / US |
| R3 | ORIENTATION ? | OFF | OFF / 1st BILL / FORWARD / REVERSE / US |
| R4 | SERIES ? | OFF | OFF / 1st BILL / DEFINED - GROUPS / US |
| R5 | UPDATE ? | NO | YES / NO |
| | TARGET 2 (POCKET 2) | | |
| R6 | DENOM. ? | 1st BILL | OFF / 1st BILL / US / ALL $1 / $2 / $5 / $10 / $20 / $50 / $100 |
| R7 | FACE ? | OFF | OFF / 1st BILL / FACE UP / FACE DOWN / US |
| R8 | ORIENTATION ? | OFF | OFF / 1st BILL / FORWARD / REVERSE / US |
| R9 | SERIES ? | OFF | OFF / 1st BILL / DEFINED - GROUPS / US |
| R10 | UPDATE ? | YES | YES / NO |
| | | | |
| R11 | STRANGER (S) | — | ~~P1 / P2 / CONT - 2 / ST~~ |
| R12 | DENOM CHANGE (DC) | P2 | P1 / P2 / CONT - 2 / ST |
| R13 | NO CALL (NC) | P2 | P1 / P2 / CONT - 2 |
| R14 | SUSPECT DOC. (SD) | P2 | P1 / P2 / CONT - 2 |
| R15 | IMPROPER SIZE (SZ) | P2 | P1 / P2 / CONT - 2 |
| R16 | UNFIT DOC. (UD) | P2 | P1 / P2 / CONT - 2 |
| R17 | REVERSE FACED (RF) | — | ~~P1 / P2 / CONT - 2~~ |
| R18 | REV. ORIENTED (RO) | — | ~~P1 / P2 / CONT - 2~~ |
| R19 | SEP. SERIES (SS) | — | ~~P1 / P2 / CONT - 2 / ST~~ |
| | | | |
| R20 | STACKER FULL (SF) | STOP | STOP / SWITCH |
| R21 | STRAP LIMIT (SL) | STOP | STOP / SWITCH / COMBINE P1 + P2 |
| R22 | CHAIN (C) | STOP - 2 | STOP - 1 / STOP - 2 |
| R23 | DOUBLE (D) | STOP - 2 | STOP - 1 / STOP - 2 |

Columns: C1, C2, C3

FIG. 37

MODE: USER - DEFINED 1

|  | SELECTION | OPTIONS |
|---|---|---|
| TARGET 1 (POCKET 1) | | |
| R1 — DENOM. ? | $100 | OFF / 1st BILL / ALL $1 / $2 / $5 / $10 / $20 / $50 / $100 |
| R2 — FACE ? | FACE UP | OFF / 1st BILL / FACE UP / FACE DOWN / US |
| R3 — ORIENTATION ? | OFF | OFF / 1st BILL / FORWARD / REVERSE / US |
| R4 — SERIES ? | 1996 + | OFF / 1st BILL / DEFINED - GROUPS / US |
| R5 — UPDATE ? | NO | YES / NO |
| TARGET 2 (POCKET 2) | | |
| R6 — DENOM. ? | $100 | OFF / 1st BILL / ALL $1 / $2 / $5 / $10 / $20 / $50 / $100 |
| R7 — FACE ? | FACE DOWN | OFF / 1st BILL / FACE UP / FACE DOWN / US |
| R8 — ORIENTATION ? | OFF | OFF / 1st BILL / FORWARD / REVERSE / US |
| R9 — SERIES ? | 1995 - | OFF / 1st BILL / DEFINED - GROUPS / US |
| R10 — UPDATE ? | NO | YES / NO |
| R11 — STRANGER (S) | P2 | P1 / P2 / CONT - 2 / ST |
| R12 — DENOM CHANGE (DC) | — | ~~P1 / P2 / CONT - 2 / ST~~ |
| R13 — NO CALL (NC) | P2 | P1 / P2 / CONT - 2 |
| R14 — SUSPECT DOC. (SD) | P2 | P1 / P2 / CONT - 2 |
| R15 — IMPROPER SIZE (SZ) | P2 | P1 / P2 / CONT - 2 |
| R16 — UNFIT DOC. (UD) | P2 | P1 / P2 / CONT - 2 |
| R17 — REVERSE FACED (RF) | P2 | P1 / P2 / CONT - 2 |
| R18 — REV. ORIENTED (RO) | — | ~~P1 / P2 / CONT - 2~~ |
| R19 — SEP. SERIES (SS) | P2 | P1 / P2 / CONT - 2 / ST |
| R20 — STACKER FULL (SF) | STOP | STOP / SWITCH |
| R21 — STRAP LIMIT (SL) | STOP | STOP / SWITCH / COMBINE P1 + P2 |
| R22 — CHAIN (C) | STOP - 2 | STOP - 1 / STOP - 2 |
| R23 — DOUBLE (D) | STOP - 2 | STOP - 1 / STOP - 2 |

Columns: C1, C2, C3

*FIG. 38*

MODE: USER - DEFINED 2

| | SELECTION | OPTIONS |
|---|---|---|
| TARGET 1 (POCKET 1) | | |
| R1 — DENOM. ? | ALL | OFF / 1st BILL / US / ALL $1 / $2 / $5 / $10 / $20 / $50 / $100 |
| R2 — FACE ? | OFF | OFF / 1st BILL / FACE UP / FACE DOWN / US |
| R3 — ORIENTATION ? | OFF | OFF / 1st BILL / FORWARD / REVERSE / US |
| R4 — SERIES ? | OFF | OFF / 1st BILL / DEFINED - GROUPS / US |
| R5 — UPDATE ? | —— | ~~YES / NO~~ |
| TARGET 2 (POCKET 2) | | |
| R6 — DENOM. ? | OFF | OFF / 1st BILL / US / ALL $1 / $2 / $5 / $10 / $20 / $50 / $100 |
| R7 — FACE ? | OFF | OFF / 1st BILL / FACE UP / FACE DOWN / US |
| R8 — ORIENTATION ? | OFF | OFF / 1st BILL / FORWARD / REVERSE / US |
| R9 — SERIES ? | OFF | OFF / 1st BILL / DEFINED - GROUPS / US |
| R10 — UPDATE ? | —— | ~~YES / NO~~ |
| R11 — STRANGER (S) | —— | ~~P1 / P2 / CONT - 2 / ST~~ |
| R12 — DENOM CHANGE (DC) | —— | ~~P1 / P2 / CONT - 2 / ST~~ |
| R13 — NO CALL (NC) | P1 | P1 / P2 / CONT - 2 |
| R14 — SUSPECT DOC. (SD) | P2 | P1 / P2 / CONT - 2 |
| R15 — IMPROPER SIZE (SZ) | P2 | P1 / P2 / CONT - 2 |
| R16 — UNFIT DOC. (UD) | P2 | P1 / P2 / CONT - 2 |
| R17 — REVERSE FACED (RF) | —— | ~~P1 / P2 / CONT - 2~~ |
| R18 — REV. ORIENTED (RO) | —— | ~~P1 / P2 / CONT - 2~~ |
| R19 — SEP. SERIES (SS) | —— | ~~P1 / P2 / CONT - 2 / ST~~ |
| R20 — STACKER FULL (SF) | STOP | STOP / SWITCH |
| R21 — STRAP LIMIT (SL) | STOP | STOP / SWITCH / COMBINE P1 + P2 |
| R22 — CHAIN (C) | STOP-1 | STOP - 1 / STOP - 2 |
| R23 — DOUBLE (D) | STOP-1 | STOP - 1 / STOP - 2 |

Columns: C1, C2, C3

FIG. 39

MODE: <u>USER - DEFINED 3</u>

| | | SELECTION (C2) | OPTIONS (C3) |
|---|---|---|---|
| | TARGET 1 (POCKET 1) | | |
| R1 | DENOM. ? | OFF | OFF / 1st BILL / US / ALL $1 / $2 / $5 / $10 / $20 / $50 / $100 |
| R2 | FACE ? | OFF | OFF / 1st BILL / FACE UP / FACE DOWN / US |
| R3 | ORIENTATION ? | OFF | OFF / 1st BILL / FORWARD / REVERSE / US |
| R4 | SERIES ? | OFF | OFF / 1st BILL / DEFINED - GROUPS / US |
| R5 | UPDATE ? | —— | ~~YES / NO~~ |
| | TARGET 2 (POCKET 2) | | |
| R6 | DENOM. ? | ALL | OFF / 1st BILL / US / ALL $1 / $2 / $5 / $10 / $20 / $50 / $100 |
| R7 | FACE ? | OFF | OFF / 1st BILL / FACE UP / FACE DOWN / US |
| R8 | ORIENTATION ? | OFF | OFF / 1st BILL / FORWARD / REVERSE / US |
| R9 | SERIES ? | OFF | OFF / 1st BILL / DEFINED - GROUPS / US |
| R10 | UPDATE ? | —— | ~~YES / NO~~ |
| R11 | STRANGER (S) | —— | ~~P1 / P2 / CONT - 2 / ST~~ |
| R12 | DENOM CHANGE (DC) | —— | ~~P1 / P2 / CONT - 2 / ST~~ |
| R13 | NO CALL (NC) | P2 | P1 / P2 / CONT - 2 |
| R14 | SUSPECT DOC. (SD) | P1 | P1 / P2 / CONT - 2 |
| R15 | IMPROPER SIZE (SZ) | P1 | P1 / P2 / CONT - 2 |
| R16 | UNFIT DOC. (UD) | P1 | P1 / P2 / CONT - 2 |
| R17 | REVERSE FACED (RF) | —— | ~~P1 / P2 / CONT - 2~~ |
| R18 | REV. ORIENTED (RO) | —— | ~~P1 / P2 / CONT - 2~~ |
| R19 | SEP. SERIES (SS) | —— | ~~P1 / P2 / CONT - 2 / ST~~ |
| R20 | STACKER FULL (SF) | STOP | STOP / SWITCH |
| R21 | STRAP LIMIT (SL) | STOP | STOP / SWITCH / COMBINE P1 + P2 |
| R22 | CHAIN (C) | STOP-1 | STOP - 1 / STOP - 2 |
| R23 | DOUBLE (D) | STOP-1 | STOP - 1 / STOP - 2 |

2-POCKET POCKET DELIVERY / STOPPING CONDITIONS

| | | STR 1 | STR 2 | STR FO | SRT 1 | SRT 2 | SRT 3 | SRT FO |
|---|---|---|---|---|---|---|---|---|
| POCKET 1 | NOTE | TARGET NOTE | TARGET NOTE | TARGET NOTE FACE / ORIENT | TARGET NOTE 1 WITH AUTOMATIC DENOMINATION CHANGE | TARGET NOTE | TARGET NOTE 1 | TARGET NOTE FACE / ORIENT |
| | STOP CONDITION | C, SL, D, SF, J; OPTIONAL: S, NC, SS, SD | C, SL, D, SF, S, NC, J, SD; OPTIONAL: SS | C, SF, J, D, SD, NC, S; SL COMBINE POCKETS; OPTIONAL: SS | C, SF, SL, J, D, NC, SD, DC; OPTIONAL: SS | C, SF, J, D, DC; OPTIONAL: NC, SS, SD | C, SF, J, SL, D, NC, SD; OPTIONAL: SS | C, SF, J, D, SD, NC, DC; SL COMBINE POCKETS; OPTIONAL: SS |
| POCKET 2 | NOTE | NONE | TARGET NOTE | TARGET NOTE UNFACED / NON-ORIENTED | TARGET NOTE 2 WITH AUTOMATIC DENOMINATION CHANGE | NONE | NONE | TARGET NOTE UNFACED / NON-ORIENTED |
| | STOP CONDITION | OPTIONAL: S, NC, SS, SD | C, SL, D, SF, S, NC, J, SD; OPTIONAL: SS | C, SF, J, D, SD, NC, S; SL COMBINE POCKETS; OPTIONAL: SS | C, SF, SL, J, D, NC, SD, DC; OPTIONAL: SS | OPTIONAL: NC, SS, SD | C, SF, SL, J, D, NC, SD, DC; OPTIONAL: SS | C, SF, J, D, SD, NC, DC; SL COMBINE POCKETS; OPTIONAL: SS |

FIG. 42

2-POCKET
POCKET DELIVERY / STOPPING CONDITIONS

| | | MIX 1 | MIX 2 | MIX FO | CNT |
|---|---|---|---|---|---|
| POCKET 1 | NOTE | MIXED NOTES | MIXED NOTES | FACE / ORIENT | NOTES |
| | STOP CONDITION | C, D, SF, J<br>OPTIONAL: NC, SD | C, D, SF, J, NC, SD | C, SF, J, D, SD, NC | SF, J, SL, C, D, SD |
| POCKET 2 | NOTE | NONE | MIXED NOTES | UNFACED / NON-ORIENTED | NOTES |
| | STOP CONDITION | OPTIONAL: NC, SD | C, D, SF, J, NC, SD | C, SF, J, D, SD, NC | SF, J, SL, C, D, SD |

METHOD AND APPARATUS FOR DOCUMENT PROCESSING

CROSS-REFERENCE TO RELATED APPLICATIONS

This application is a continuation of copending U.S. patent application Ser. No. 08/864,423 filed May 28, 1997 entitled "Method and Apparatus for Document Processing", which is hereby incorporated by reference in its entirety. This application is a continuation-in-part and further claims the benefit of U.S. application Ser. No. 09/126,580, filed Jul. 30, 1998 entitled "Method and Apparatus for Discriminating and Counting Documents", which claims the benefit of U.S. application Ser. No. 08/573,392, which was issued on Aug. 4, 1998 as U.S. Pat. No. 5,790,697 entitled "Method and Apparatus for Discriminating and Counting Documents".

BACKGROUND OF THE INVENTION

U.S. patent application Ser. No. 08/864,423 claims the benefit of Provisional Patent Application Ser. No. 60/018,563 filed May 29, 1996 entitled "Method and Apparatus for Document Identification and Authentication", No. 60/034,954 filed Jan. 16, 1997 entitled "Method and Apparatus for Document Processing", and No. 60/038,340 filed Feb. 27, 1997 entitled "Method and Apparatus for Document Processing."

U.S. patent application Ser. No. 08/864,423 is a continuation-in-part and further claims the benefit of U.S. patent application Ser. No. 08/800,053, which was issued on Nov. 30, 1999 as U.S. Pat. No. 5,992,601 entitled "Method and Apparatus for Document Identification and Authentication".

U.S. patent application Ser. No. 08/800,053 claims the benefit of Provisional Patent Application Ser. Nos. 60/011,688 filed Feb. 15, 1996, now abandoned, and No. 60/018,563 filed May 29, 1996.

FIELD OF THE INVENTION

The present invention relates, in general, to document processing. More specifically, the present invention relates to a method and apparatus for document discrimination, authentication, and/or sorting.

BACKGROUND

A variety of techniques and apparatus have been used in automated currency handling systems. Traditionally, these currency handling systems utilized a complex series of belts, pulleys, wheels and rollers to guide a currency bill through a complicated pathway having many twists and turns to pass the currency bill through the discriminating and/or authenticating sensors and to deliver the bills to an assigned output receptacle. These complicated pathways have sometimes led to jams of the currency bills which are difficult to clear.

Therefore, a need exists for a transport mechanism that reduces currency jams and is more accessible when clearing currency jams.

There is also a need for a currency evaluation device that can distinguish bills based on a number of criteria and that is flexible in permitting the operator of the device to specify which criteria are to be used to distinguish bills and how bills meeting or failing to meet various criteria are to be handled. There is also a need for a currency evaluation device having an input/output means that is simply to operate, flexible, and customizable.

SUMMARY OF THE INVENTION

It is an object of the present invention to provide a method and apparatus for document transport which reduces currency jams and is more accessible when clearing currency jams. Briefly, according to one embodiment, a method and apparatus for transporting a currency bill to be evaluated by a discrimination and/or authentication apparatus is provided. A transport mechanism includes a pair of substantially smooth opposing plates. These plates are substantially free of surface features. The smooth plates comprise a transport plate and a follower plate and define a currency pathway there between. A plurality of transport rolls protrude through apertures in the transport plate so as to frictionally engage the bills and actively advance the bills through the currency pathway. Furthermore, the follower plate is preferably mounted on a hinged module so that it may rotate out and away from the transport plate to allow easy access to the currency pathway.

In one embodiment, a transport mechanism includes a transport plate which defines in a substantially planar transport path between an evaluating mechanism and a plurality of output receptacles. The transport mechanism may include a follower plate that is substantially smooth and without surface features. The follower plate is positioned substantially parallel and in spaced relation to the opposing transport plate so as to define a currency pathway there between.

According to another embodiment, a currency evaluation device for receiving a stack of currency bills and rapidly evaluating all the bills in the stack is provided. The device has an input receptacle for receiving a stack of bills to be evaluated and a number of output receptacles for receiving the bills after the bills have been evaluated. A transport mechanism transports the bills, one at a time, from the input receptacle to one of the output receptacles along a transport path. A discriminating unit evaluates the bills including determining certain information concerning the bills. A control panel includes a touch screen for displaying the information concerning the bills and for receiving operational instructions from a user. A controller coupled to the touch screen and the discriminating unit causes the discriminating unit to operate in a number of modes in response to the operational instructions from the user. In one embodiment, the evaluation device has exactly two output receptacles.

According to another embodiment, a currency evaluation device for receiving a stack of currency bills and rapidly evaluating all the bills in the stack is provided wherein the device flags bills meeting or failing to meet certain criteria. A bill may be flagged, for example, by presenting the bill in one of the output pockets (delivering the bill to one of the pockets and suspending the operation of the device) or by off-sorting the bill to a different output pocket and continuing to process other bills. According to one embodiment the currency evaluation device has two output receptacles for receiving bills after they have been evaluated.

According to another embodiment a currency evaluation device has a routing interface. The routing interface has a data retrieval device such as a touch screen that receives information from a user of the evaluation device specifying into which output receptacle bills are to be delivered based on one or more criteria such as, e.g., a bill being a stranger.

According to another embodiment a currency evaluation device has a flagging control interface. The flagging control interface has a data retrieval device such as a touch screen that receives information from a user of the evaluation device specifying whether the evaluation device should suspend its operation based on the detection of a bill meeting or failing to meet one or more criteria such as, e.g., a bill being a no call bill.

BRIEF DESCRIPTION OF THE DRAWINGS

Other objects and advantages of the invention will become apparent upon reading the following detailed description in conjunction with the drawings in which:

FIG. 7b is a front view of a first region of a transport plate according to one embodiment of the present invention;

FIG. 7c is a sectional side view of the first region of a transport plate depicted in FIG. 7b;

FIG. 8a is a sectional side view taken across a currency pathway depicting a bill passing below a first follower plate according to one embodiment of the present invention;

FIG. 8b is a sectional side view of a first follower plate according to one embodiment of the present invention;

FIG. 8c is a front view of the first follower plate depicted in FIG. 8b;

FIG. 9a is a sectional side view taken across a currency pathway depicting a bill passing below a second follower plate according to one embodiment of the present invention;

FIG. 9b is a sectional side view of a second follower plate according to one embodiment of the present invention;

FIGS. 21–33 illustrate various touch screen displays according to various embodiments of the present invention;

FIGS. 35–40 illustrate examples of operating parameters selection screens; and

FIGS. 41 and 42 are tables summarizing various embodiments of several operating modes.

DETAILED DESCRIPTION OF THE EMBODIMENTS

The transport mechanism of the present invention may be used and incorporated in an apparatus which sorts, analyzes, transports, evaluates, authenticates, discriminates, counts or otherwise processes documents. In one embodiment, a transport mechanism of the present invention is incorporated in an evaluation apparatus for discriminating and/or authenticating currency bills. However, the transport mechanism of the present invention may be employed in conjunction with the processing of other documents such as, for example, stock certificates, bonds, postage stamps and food stamps.

Figure 1A:
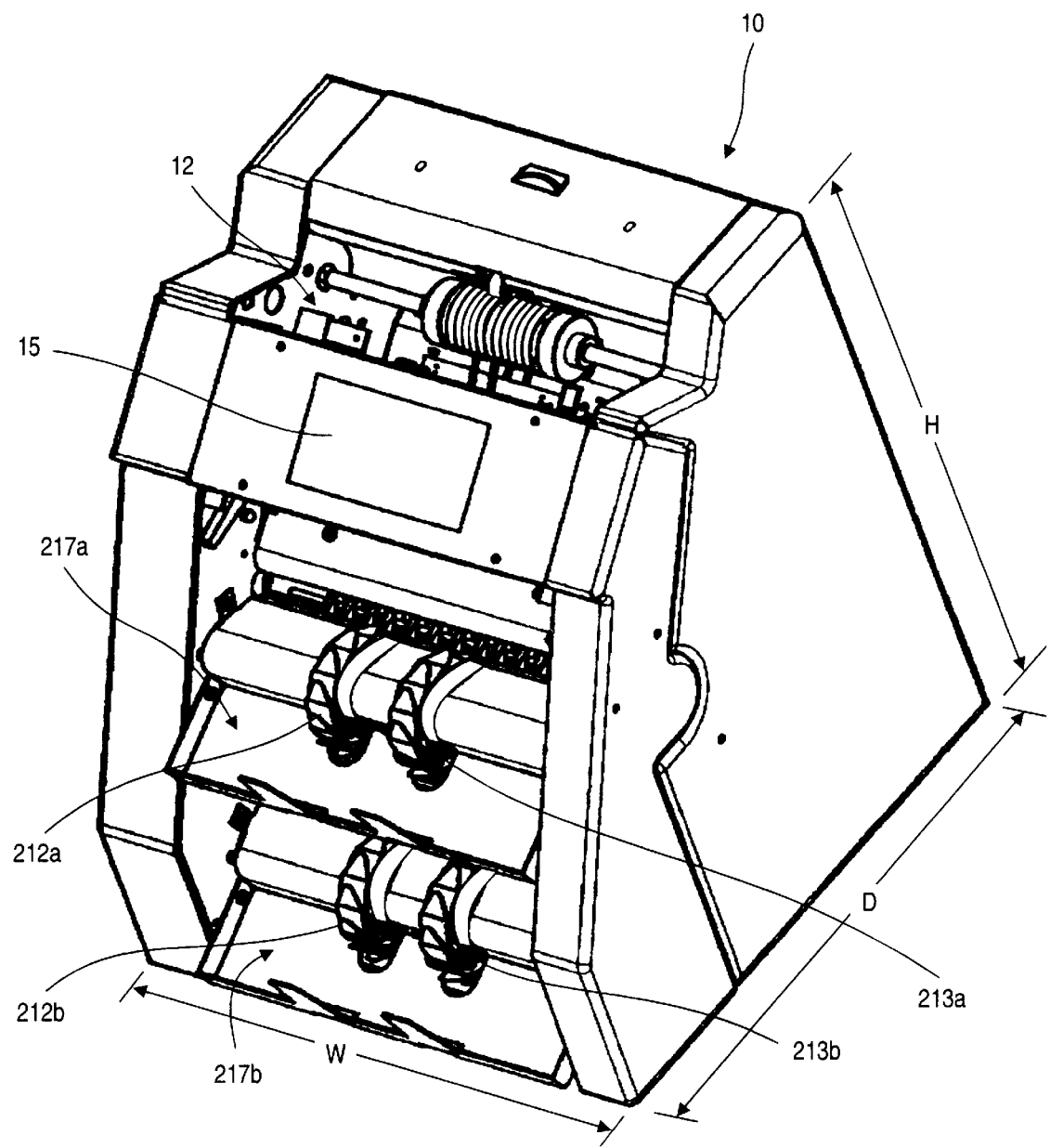
FIG. 1a is a perspective view of a multi-pocket document evaluation device according to one embodiment of the present invention.
Figure 1B:
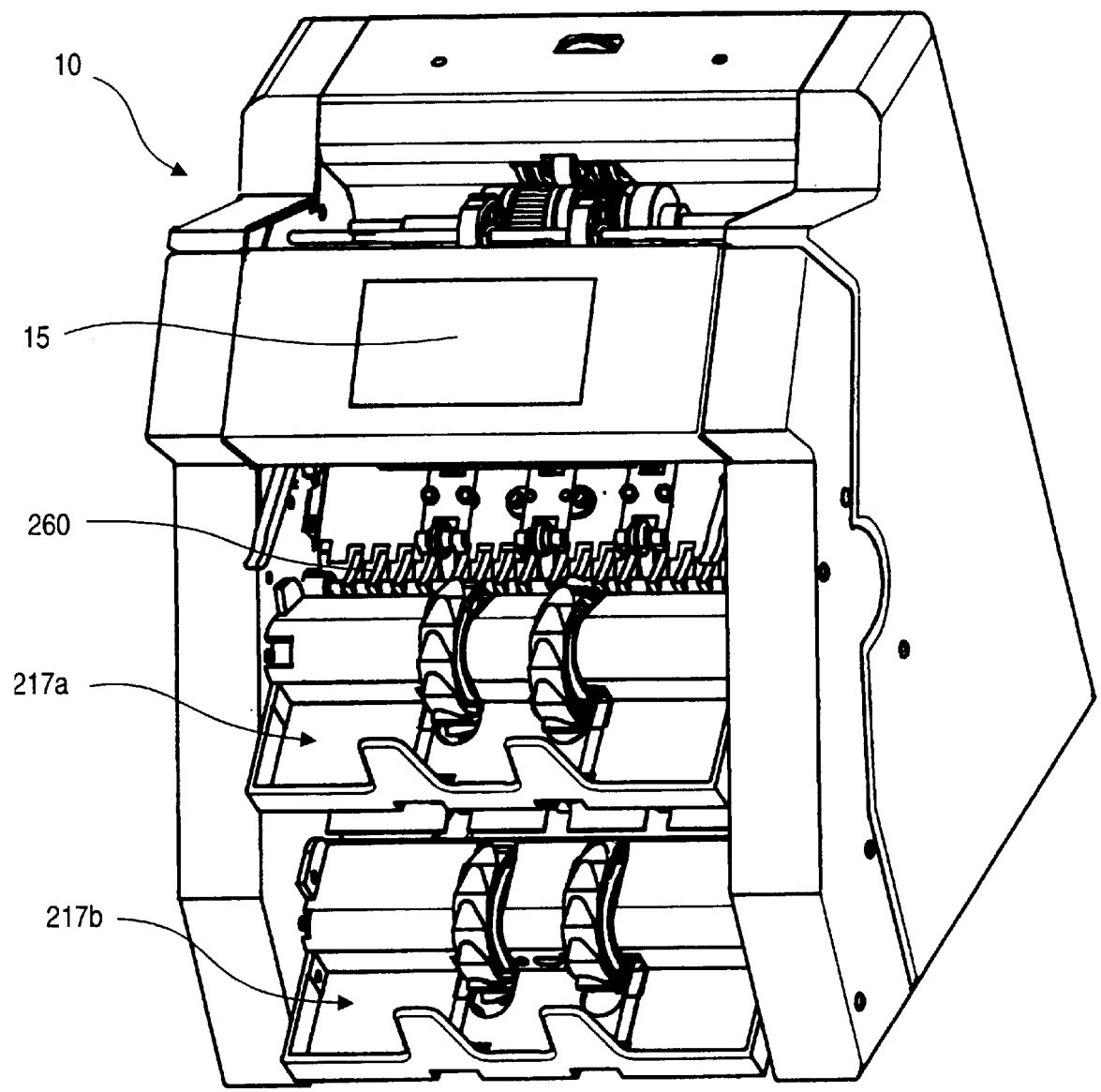
FIG. 1b is another perspective view of a multi-pocket document evaluation device according to one embodiment of the present invention.
Figure 2:
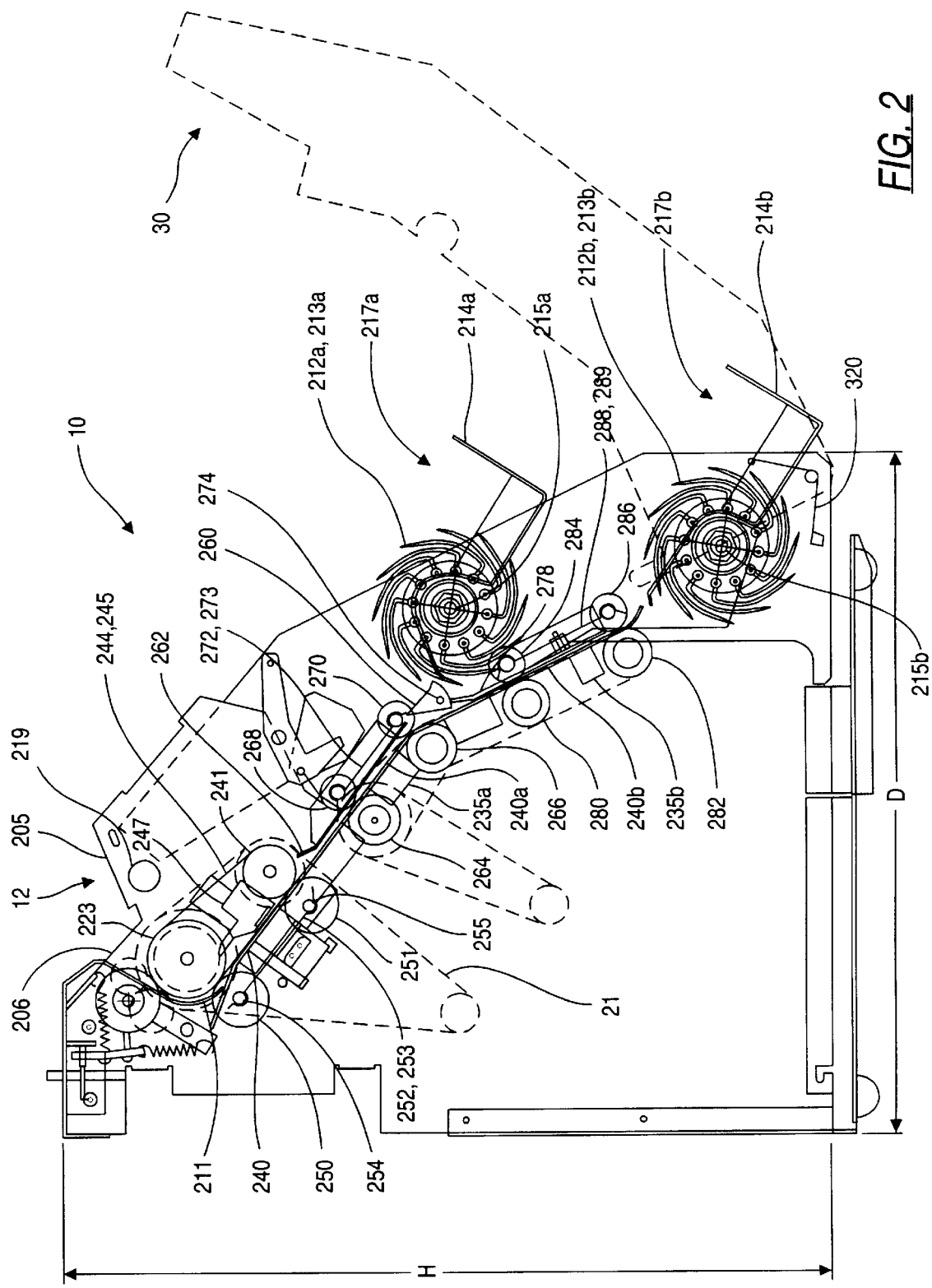
FIG. 2 is a side view of an evaluation device depicting various transport rolls in side elevation according to one embodiment of the present invention.

FIGS. 1a and 1b depict an exterior perspective view and FIG. 2 is a side view of a multi-pocket document evaluation device 10 such as a currency discriminator according to one embodiment of the present invention. According to one embodiment the currency discriminator 10 is compact having a height (H) of about 17½ inches (44.5 cm), width (W) of about 13½ inches (34.3 cm), and a depth (D) of about 15 inches (38.1 cm) and weighs approximately 35 lbs. (16 kg). The evaluation device 10 may be rested upon a tabletop.

In FIGS. 1a, 1b, and 2, currency bills are fed, one by one, from a stack of currency bills placed in an input receptacle 12 into a transport mechanism. The transport mechanism includes a transport plate or guide plate 240 for guiding currency bills to one of a plurality of output receptacles 217a and 217b. Before reaching the output receptacles 217a, 217b a bill can be, for example, evaluated, analyzed, authenticated, discriminated, counted and/or otherwise processed. The results of the above process or processes may be used to determine to which output receptacle 217a, 217b a bill is directed. In one embodiment, documents such as currency bills are transported, scanned, and identified at a rate equal to or greater than 600 bills per minute. In another embodiment, documents such as currency bills are transported, scanned, and identified at a rate equal to or greater than 800 bills per minute. In another embodiment, documents such as currency bills are transported, scanned, and identified at a rate equal to or greater than 1000 bills per minute. For currency bills, the identification may include the determination of the denomination of each bill.

The input receptacle 12 for receiving a stack of bills to be processed is formed by downwardly sloping and converging walls 205 and 206 (see FIG. 2) formed by a pair of removable covers (not shown) which snap onto a frame. The converging wall 206 supports a removable hopper (not shown) that includes vertically disposed side walls (not shown). One embodiment of an input receptacle is described and illustrated in more detail in U.S. patent application Ser. No. 08/450,505 filed May 26, 1995, entitled "Method and Apparatus for Discriminating and Counting Documents" which is incorporated by reference in its entirety. The currency discriminator 10 in FIGS. 1a and 1b has a touch panel display 15 in one embodiment of the present invention which displays appropriate "functional" keys when appropriate. The touch panel display 15 simplifies the operation of the multi-pocket currency discriminator 10. The touch panel display 15 may be a full graphics display. Alternatively or additionally physical keys or buttons may be employed.

From the input receptacle 12, the currency bills are moved in seriatim from the bottom of a stack of bills along a curved guideway 211 (shown in FIG. 2) which receives bills moving downwardly and rearwardly and changes the direction of travel to a forward direction. A stripping wheel 220 (shown in FIG. 3) mounted on a stripping wheel shaft 219 aids in feeding the bills to the curved guideway 211. The curvature of the guideway 211 corresponds substantially to the curved periphery of a drive roll 223 so as to form a narrow passageway for the bills along the rear side of the drive roll 223. An exit end of the curved guideway 211 directs the bills onto the transport plate 240 which carries the bills through an evaluation section and to one of the output receptacles 217a, 217b.

Stacking of the bills in one embodiment is accomplished by a pair of driven stacking wheels 212a and 213a for the first or upper output receptacle 217a and by a pair of stacking wheels 212b and 213b for the second or bottom output receptacle 217b. The stacker wheels 212a,b and 213a,b are supported for rotational movement about respective shafts 215a,b journalled on a rigid frame and driven by a motor (not shown). Flexible blades of the stacker wheels 212a and 213a deliver the bills onto a forward end of a stacker plate 214a. Similarly, the flexible blades of the stacker wheels 212b and 213b deliver the bills onto a forward end of a stacker plate 214b.

A diverter 260 directs the bills to either the first or second output receptacle 217a, 217b. When the diverter is in a lower position, bills are directed to the first output receptacle 217a. When the diverter 260 is in an upper position, bills proceed in the direction of the second output receptacle 217b.

Figure 4:
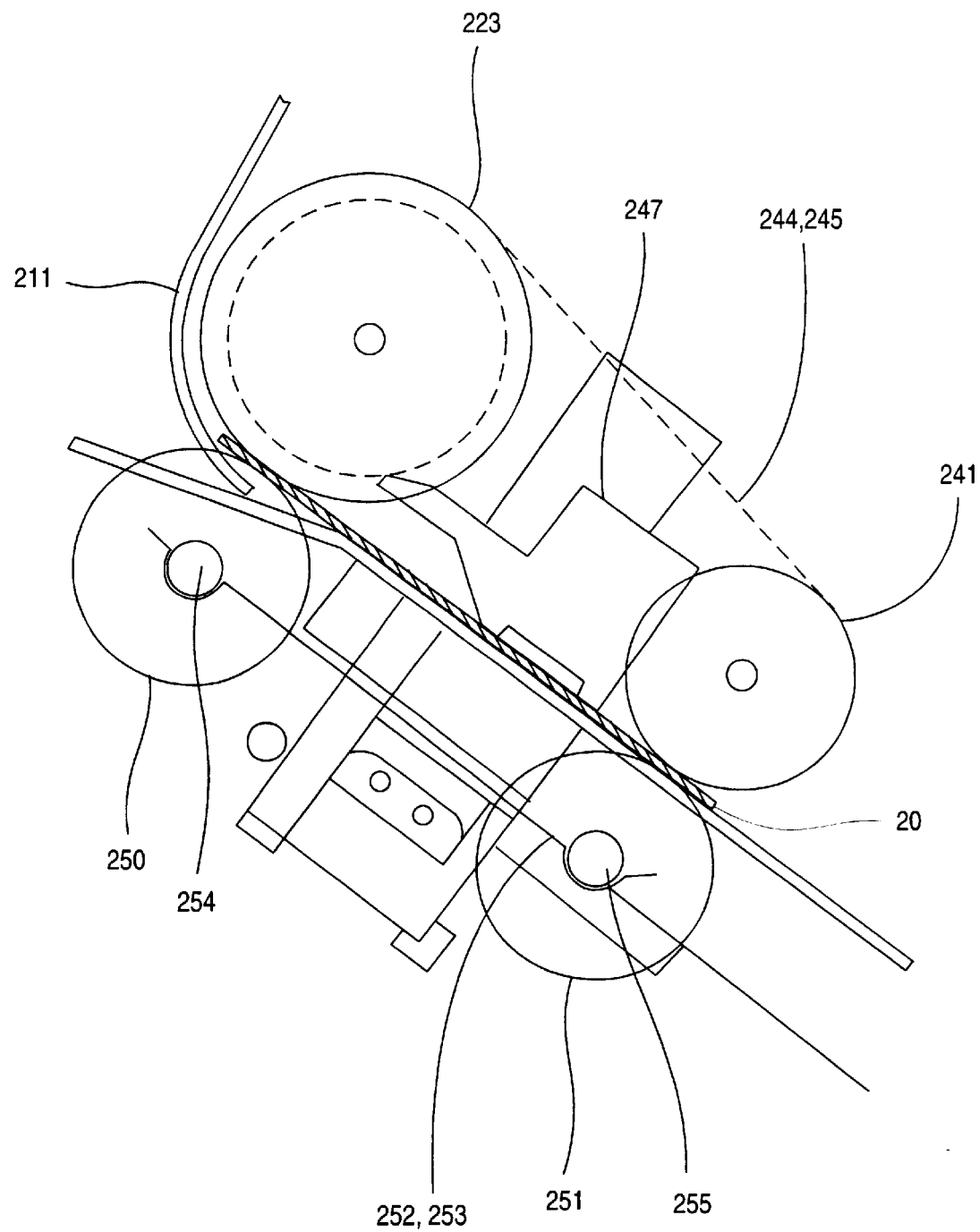
FIG. 4 is a sectional side view taken across a currency pathway depicting a bill in the region of an evaluating mechanism according to one embodiment of the present invention.

Referring to FIG. 4, at a lower end of the curved guideway 211, a bill 20 being transported by the drive roll 223 engages the transport plate 240. Bills are positively driven along the transport plate 240 by means of a transport roll arrangement comprising both driven and passive rolls. A pair of O-rings 244 and 245 fit into grooves formed in a drive roll 241 and in the drive roll 223. The pair of O-rings 244 and 245 engage the bill 20 continuously between the two driven upper rolls 223 and 241 and assist in holding the bill 20 flat against the transport plate 240. Such an embodiment aids to the performance of the sensors of the evaluation region 247. Rolls 223 and 241 are driven by a motor (not shown) via a belt 21. Such an arrangement is illustrated in more detail in U.S. patent application Ser. No. 08/450,505 referred to above.

Figure 5:
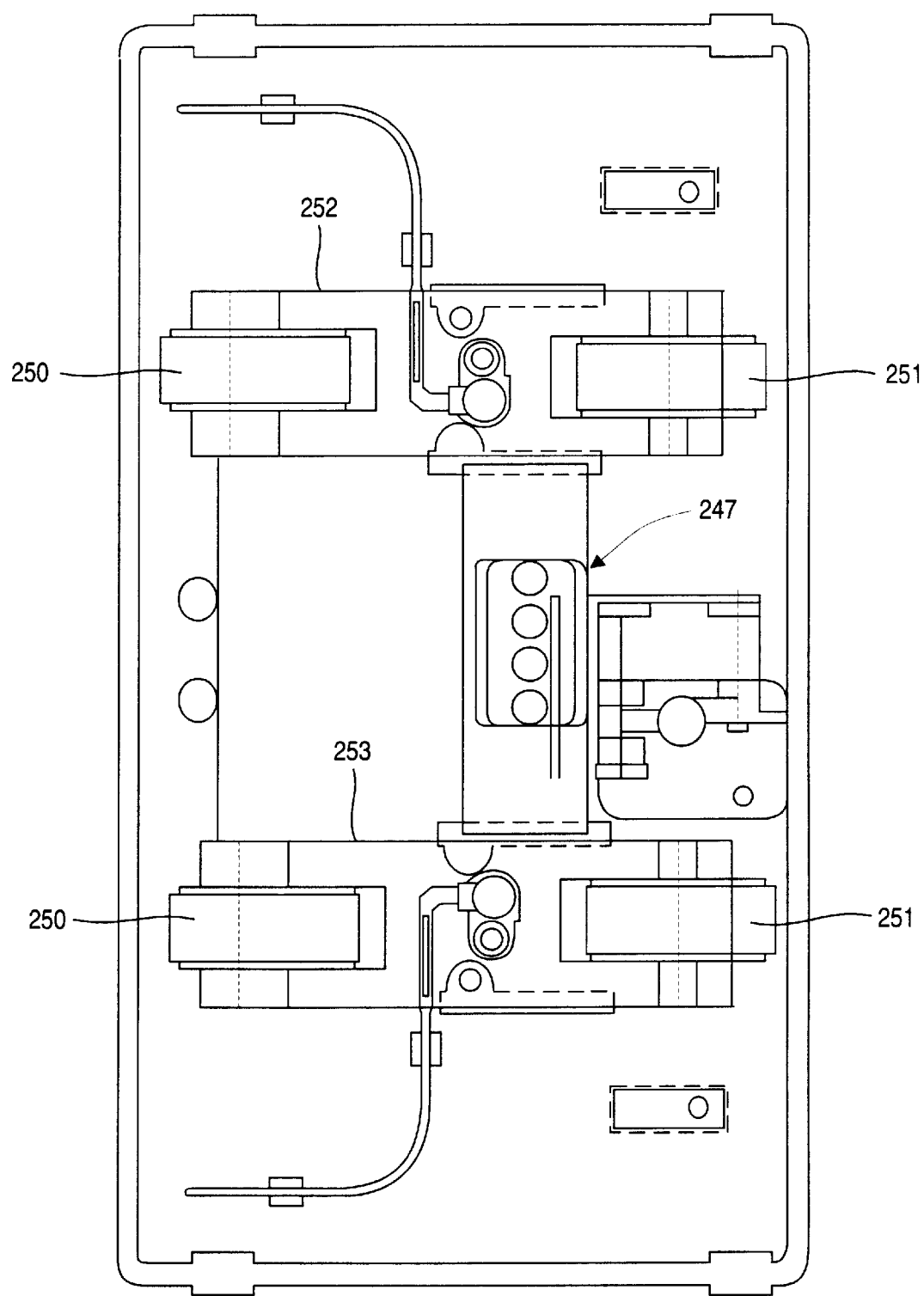
FIG. 5 is a sectional bottom view depicting a portion of a transport plate illustrating H-shaped leaf springs in conjunction with passive rolls according to one embodiment.

Passive rolls 250, 251 are mounted on an underside of the transport plate 240 in such a manner as to be freewheeling about their respective axes 254 and 255 and biased into counter-rotating contact with their corresponding driven upper rolls 223 and 241. The passive rolls 250 and 251 preferably have high-friction rubber surfaces and are biased into contact with their respective driven upper rolls 223 and 241 by means of a pair of H-shaped leaf springs 252 and 253 (see FIG. 5). The central portion of each leaf spring is fastened to the transport plate 240, which is fastened rigidly to the machine frame, so that the relatively stiff arms of the H-shaped springs exert a constant biasing pressure against the passive rolls 250 and 251 and push them against the corresponding upper rolls 223 and 241.

Referring back to FIG. 4, the driven and passive transport rolls are preferably coplanar with a flat upper surface of the transport plate 240 so that currency bills can be positively driven along the top surface of the plate in a flat manner. To minimize the possibility of bill skew and to enhance the reliability of the overall scanning and recognition process, the bills are firmly gripped under uniform pressure between the driven and passive rolls. The H-shaped leaf springs 252 and 253 aid in reducing bill twisting or skewing. The O-rings 244, 245 are also effective in ensuring that central portions of the bills are held flat. The distance between the axes of the two driven upper rolls 223 and 241 and the corresponding counter-rotating passive rolls 250 and 251 is selected to be just short of a length of a narrow dimension of the currency bills.

Figure 6:
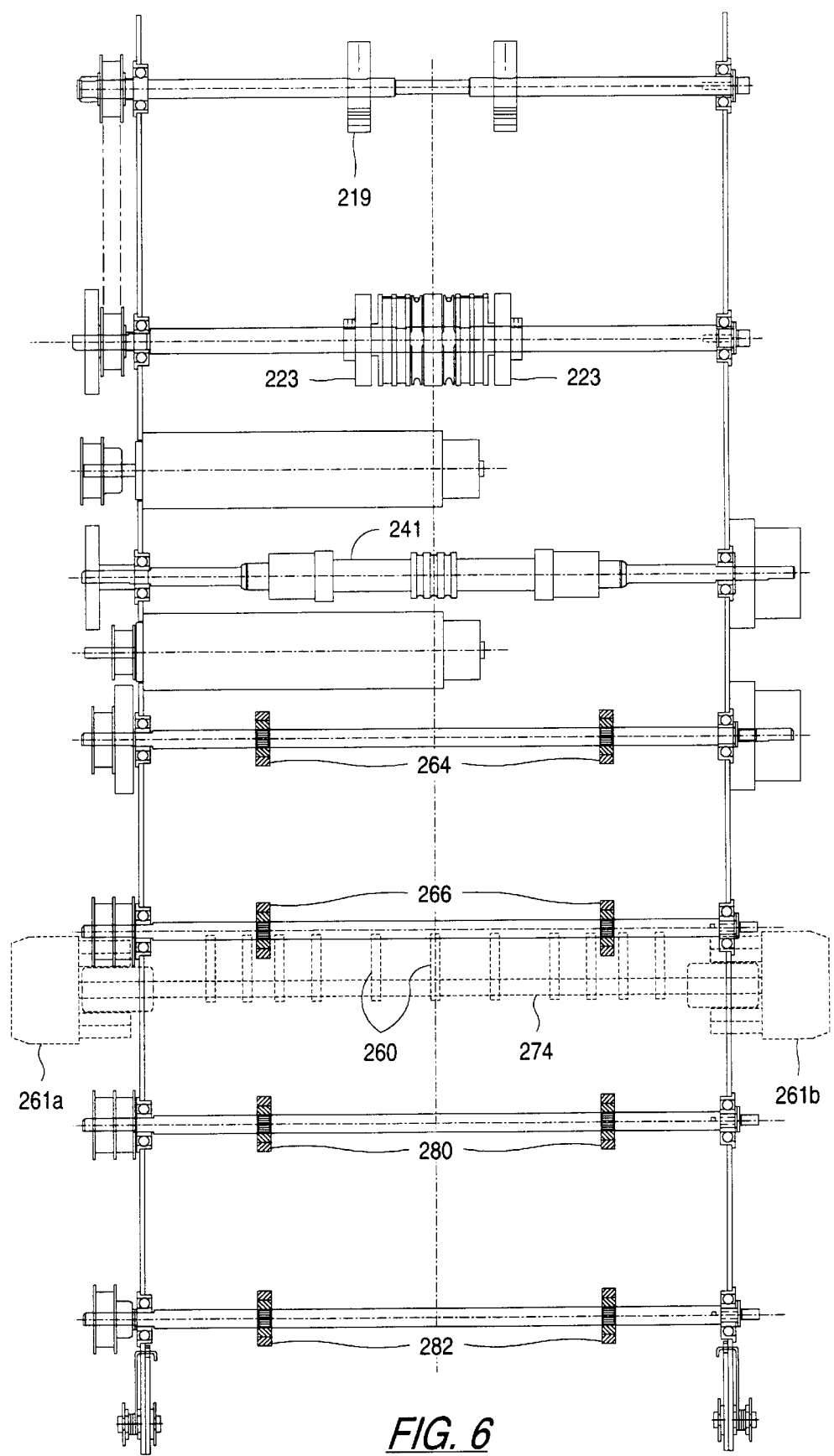
FIG. 6 is a top view of a machine depicting various shafts according to one embodiment of the present invention.

FIG. 6 depicts various shafts of the multi-pocket document evaluation device 10 according to one embodiment of the present invention. The distance between the shafts should preferably be less than the width of the bills that are to be evaluated.

Figure 7A:
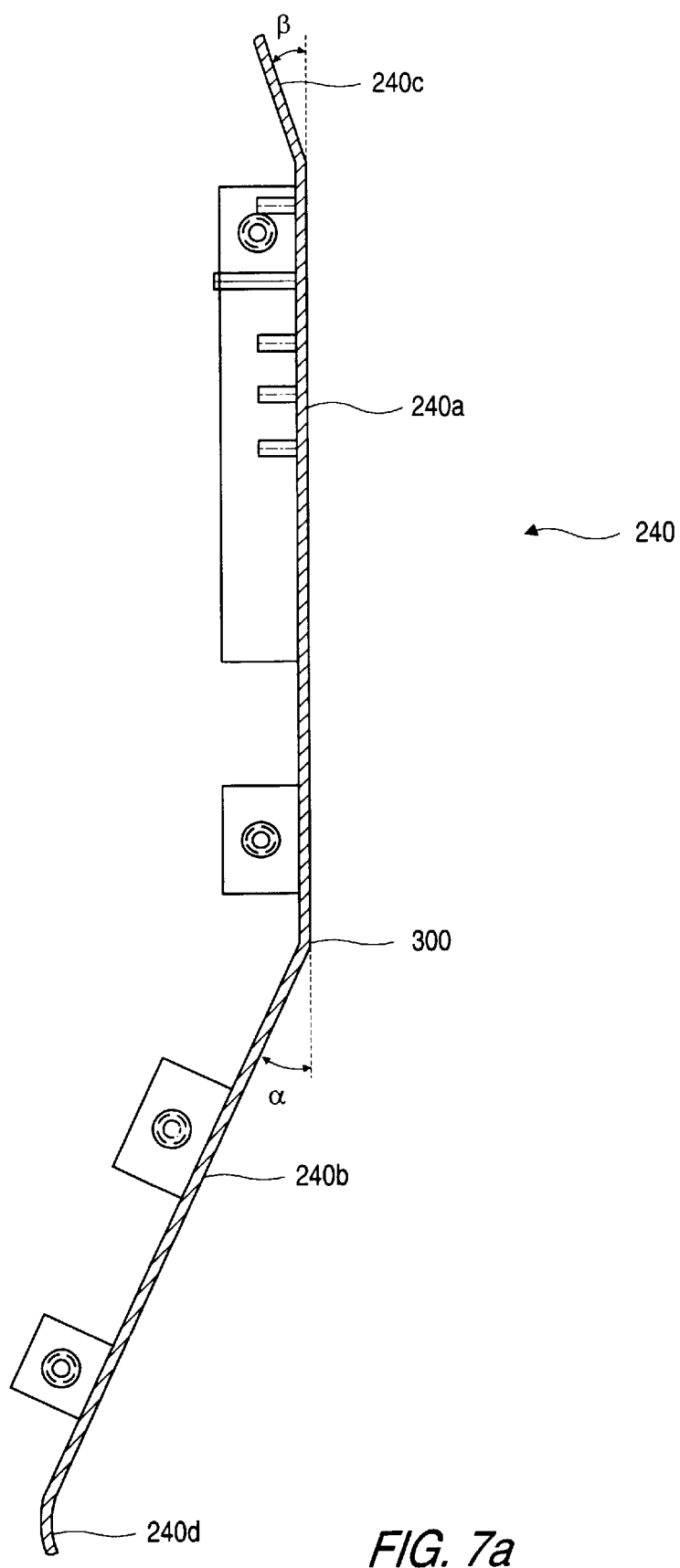
FIG. 7a is a sectional side view of a transport plate according to one embodiment of the present invention.
Figure 7E:
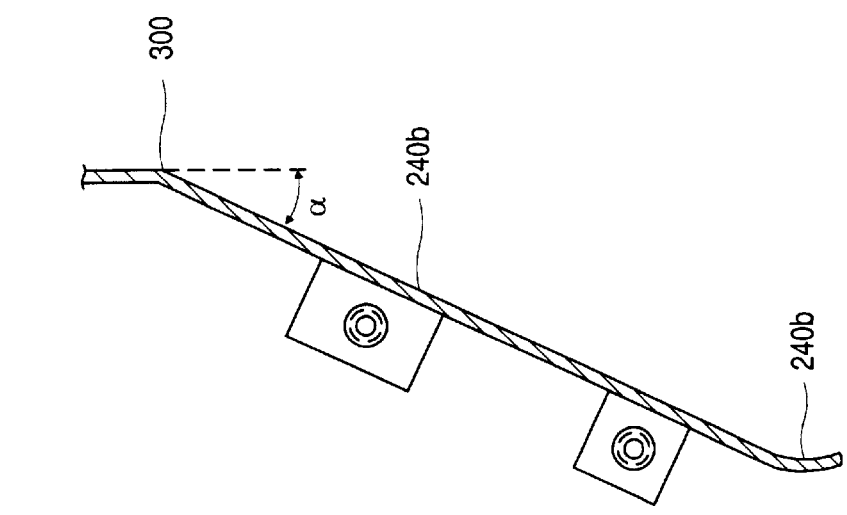
FIG. 7e is a sectional side view of the second region of a transport plate depicted in FIG. 7d.

As best shown in FIG. 7a, according to one embodiment of the present invention the transport plate 240 is substantially flat and linear. The uncomplicated surfaces of the transport plate 240 have no protruding features. In one embodiment, there are no belts employed to engage and advance bills after they have been evaluated in the evaluation region 247. In this embodiment, the bills are delivered to an appropriate output receptacle 217a or 217b after being evaluated without the use of belts contacting the bills.

The transport plate 240 has a first substantially planar region 240a defining a first plane. The evaluation of bills is performed in the first substantially planar region 240a. The first substantially planar region 240a ends at a point 300. The transport plate 240 also has a second substantially planar region 240b defining a second plane. The second substantially planar region 240b begins at the point 300. The second substantially planar region extends up to a diverting flange 240d. In one embodiment, the first and second substantially planar regions 240a and 240b substantially define the entire region of the transport path from the evaluation mechanism to the plurality of output receptacles 217a,b.

In one embodiment, the second substantially planar region 240b does not deviate from the first substantially planar region 240a by more than about 90 degrees. In a second embodiment, the second region 240b does not deviate from the first region 240a by more than about 60 degrees. In a third embodiment, the second region 240b does not deviate from the first region 240a by more than about 45 degrees. In a fourth embodiment, the second region 240b does not deviate from the first region 240a by more than about 30 degrees. As depicted in FIG. 7a, the second region 240b is substantially planar with the first region 240a, deviating from the first region 240a by an angle of α degrees where at is about 26 degrees.

The transport plate 240 also has a third substantially planar region 240c defining a third plane. In one embodiment, the third substantially planar region 240c does not deviate by more than about 45 degrees from the first region 240a. In another embodiment, the third region 240c does not deviate by more than about 25 degrees from the first region 240a. As depicted in FIG. 7a, the third region 240c deviates from the first region 240a by an angle of β degrees where β is about 16 degrees.

The transport plate 240 has a plurality of apertures 25 therein. According to one embodiment, apertures 25 are present only where necessary to facilitate the functioning of passive rolls and driven rolls and a diverter 260. According to another embodiment, apertures 25 are present only where necessary to facilitate the functioning of passive and driven rolls, diverter 260, and various sensors such as scanheads, doubles detectors, and document location sensors. Apertures for sensors may covered with materials that do not interfere with the functioning of corresponding sensors while nonetheless facilitating the transport plate in appearing smooth and continuous to passing bills. For example, when optical sensors are being employed, corresponding apertures may contain lenses that are flush with the transport surface of the transport plate. Likewise, materials that do not interfere with the operation of magnetic sensors may be employed to cover any apertures created to facilitate their operation. Accordingly, such coverings essentially become part of the transport plate, effectively negating the existence of the corresponding apertures. Alternatively, the transport plate may be constructed from a material that does not interfere with the operation of such sensors so that no apertures need be created in the first place, e.g., a clear plastic transport plate permitting the functioning of optical sensors.

Apertures 25 in first region 240a of the transport plate 240 are shown in FIG. 7b. Apertures 25a permit passive and driven rolls to protrude into the currency pathway to thereby advance bills along the pathway. Apertures 25b permit ends of the diverter 260 to rotate below the upper surface of the transport plate 240. Aperture 25c permits a lower scanhead to read the underside of a passing document. The lower scanhead may be, for example, an optical scanhead. Apertures 25d provide access for double detection sensors that determine whether two or more bills are being transported in a stacked or overlapping manner. An example of optical scanheads and double detection sensor are described in more detail in conjunction with FIGS. 13–16. Apertures 25c and 25d may contain lenses that are flush with the transport surface of the transport plate. Where apertures 25c and 25d contain such lenses, the transport plate 240a effectively contains only apertures 25a and 25b (i.e., apertures only for the transport rolls and the diverter).

Figure 7D:
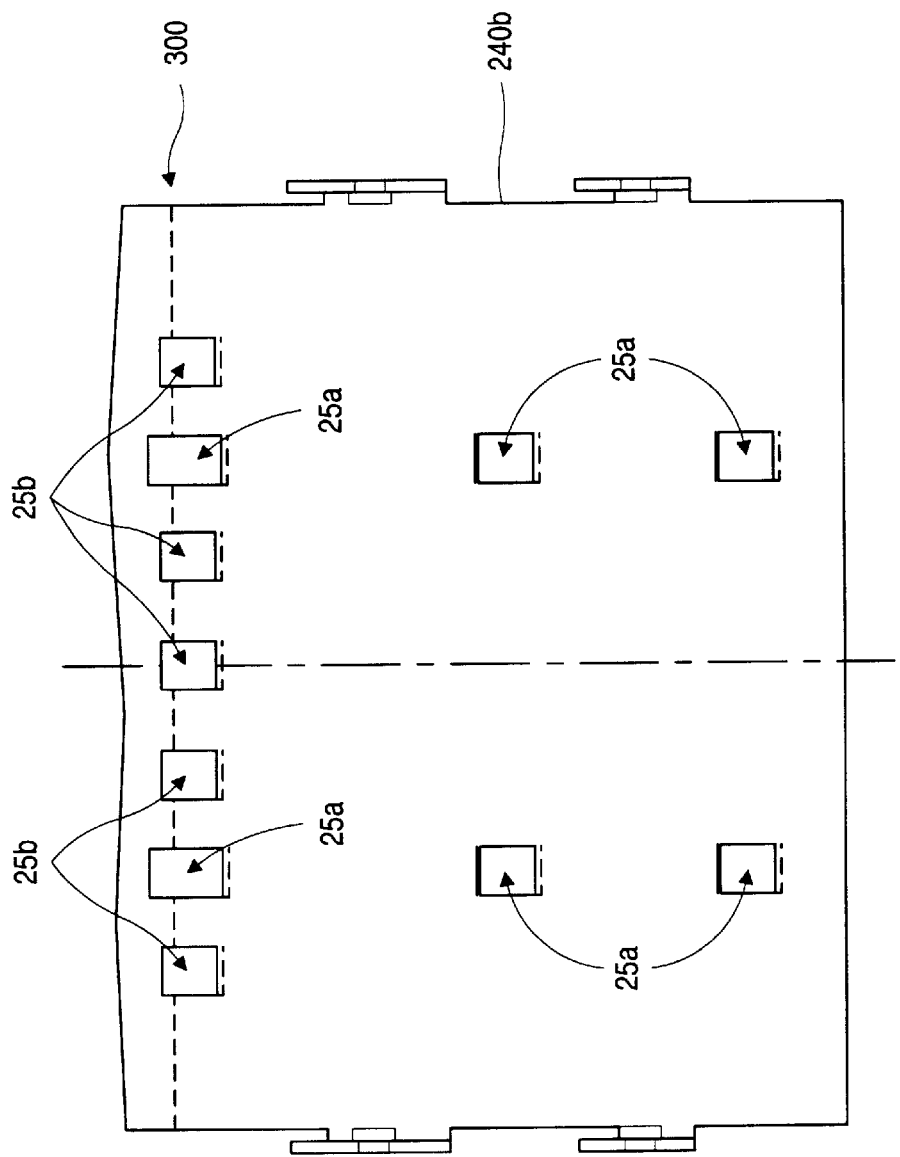
FIG. 7d is a front view of a second region of a transport plate according to one embodiment of the present invention.

Apertures 25a and 25b in a second region 240b of the transport plate 240 are shown in FIG. 7d. This clean and unobstructed of transport plate 240 facilitates a reduction in the jamming of the currency bills as well as facilitating the ease with which jammed bills can be removed from the system 10.

According to one embodiment, the transport plate 240 has a unitary and integral construction. Such an embodiment is depicted in FIGS. 2 and 7a–7e. However, the transport plate 240 may be constructed of a plurality of individual plates. Such an alternate embodiment is illustrated in FIGS. 10a–10b and 11a–11b. Referring to FIG. 11b, a portion of a transport plate 240' is depicted in which one of a plurality of individual plates is illustrated. The transport plate 240' includes the portion depicted in FIG. 11b and another portion 240" (see FIG. 10a) in the vicinity of the evaluation region. In one embodiment, the transport plate 240" is comprised of a molded plastic plate. Both portions of the transport plate 240' and 240" in this embodiment are substantially flat and linear. As depicted, the surfaces of the transport plate 240' have no protruding features. As described above in connection with plate 240, in this embodiment, the bills are delivered to an appropriate output receptacle 217a or 217b after being evaluated without the use of belts contacting the bills.

The portion of the transport plate 240' depicted in FIG. 11b has a first substantially planar region 240e defining a first plane. The substantially planar region 240e according to this embodiment begins after the bills have been evaluated. The substantially planar region 240e may optionally be slightly angled at a point 301' to assist in preventing bills from getting caught in the area between the evaluating mechanism and the substantially planar region 240e. As illustrated, the first substantially planar region 240e ends at a point 300'. The transport plate 240' also has a second substantially planar region 240f defining a second plane. The second substantially planar region 240f begins at the point 300'. The second substantially planar region extends up to a diverting flange 240g. In one embodiment, the first and second substantially planar regions 240e and 240f define substantially the entire path from the evaluation region to the plurality of output receptacles 217a,b.

In one embodiment, the second substantially planar region 240f does not deviate from the first substantially planar region 240e by more than about 90 degrees. In a second embodiment, the second region 240f does not deviate from the first region 240e by more than about 60 degrees. In a third embodiment, the second region 240f does not deviate from the first region 240e by more than about 45 degrees. In a fourth embodiment, the second region 240f does not deviate from the first region 240e by more than about 30 degrees. As depicted in FIG. 11b, the second region 240f is substantially planar with the first region 240e, deviating from the first region 240e by an angle of γ degrees where γ is about 26 degrees.

As with the transport plate 240, transport plate 240' has a plurality of apertures 27 therein. According to one embodiment, apertures 27 are present only where necessary to facilitate the functioning of passive rolls and driven rolls and a diverter 260. According to another embodiment, apertures 27 are present only where necessary to facilitate the functioning of passive and driven rolls, diverter 260, and various sensors such as scanheads, doubles detectors, and document location sensors. Apertures for sensors may filled with materials that do not interfere with the functioning of corresponding sensors while nonetheless facilitating the transport plate in appearing smooth and continuous to passing bills. For example, when optical sensors are being employed, corresponding apertures may contain lenses that are flush with the transport surface of the transport plate.

Figure 11A:
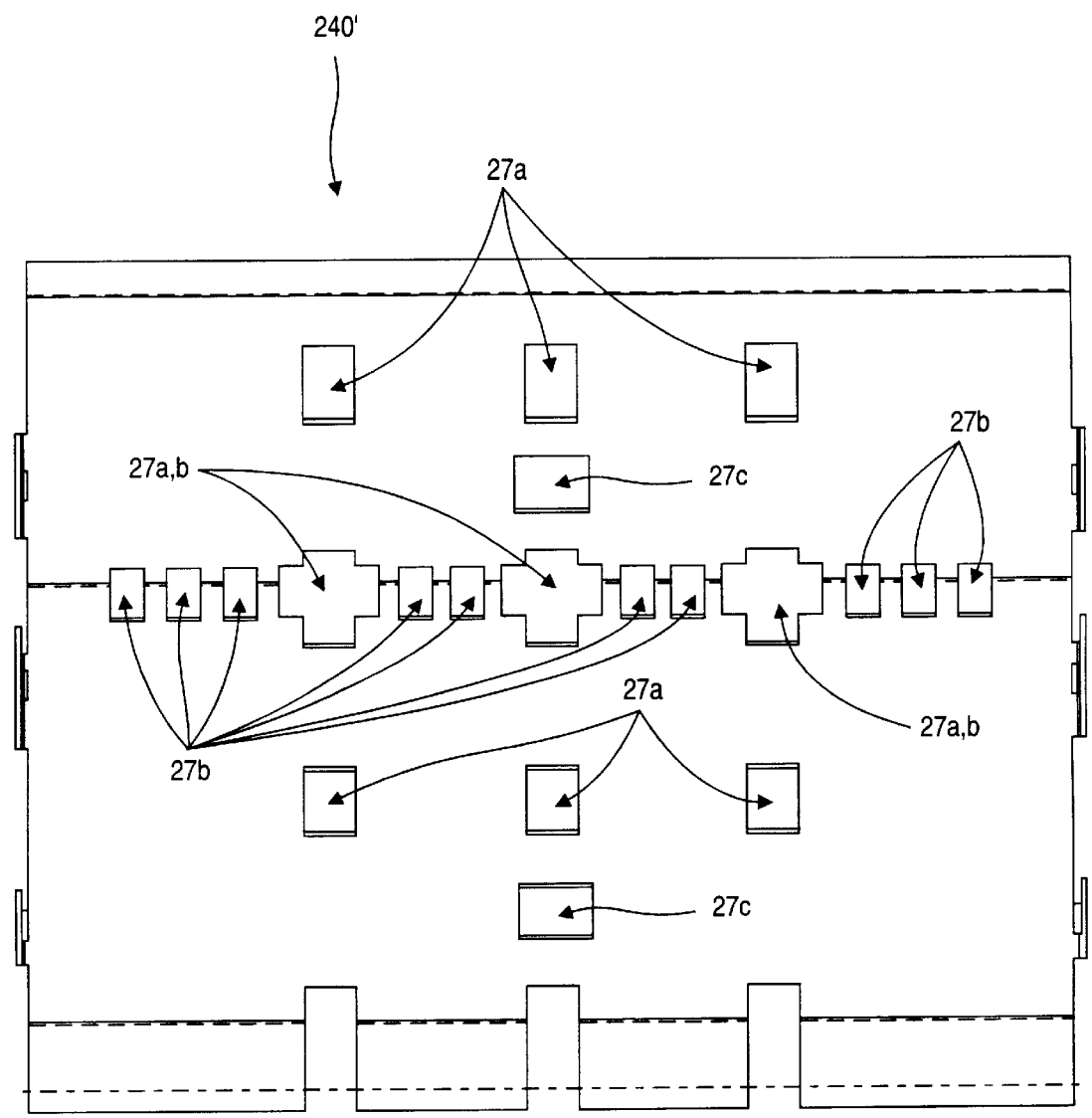
FIG. 11a is a front view of a transport plate according to one embodiment of the present invention.

Apertures 27 of the transport plate 240' are shown in FIG. 11a. Apertures 27a permit passive and driven rolls to protrude into the currency pathway. Apertures 27b permit ends of the diverter 260 to rotate below the upper surface of the transport plate 240'. Apertures 27c facilitate the functioning of sensors such as sensors 235a and 235b described below in connection with FIGS. 8a and 9a. This clean and unobstructed of transport plate 240' facilitates a reduction in the jamming of the currency bills as well as facilitating the ease with which jammed bills can be removed from the system 10.

Figure 9C:
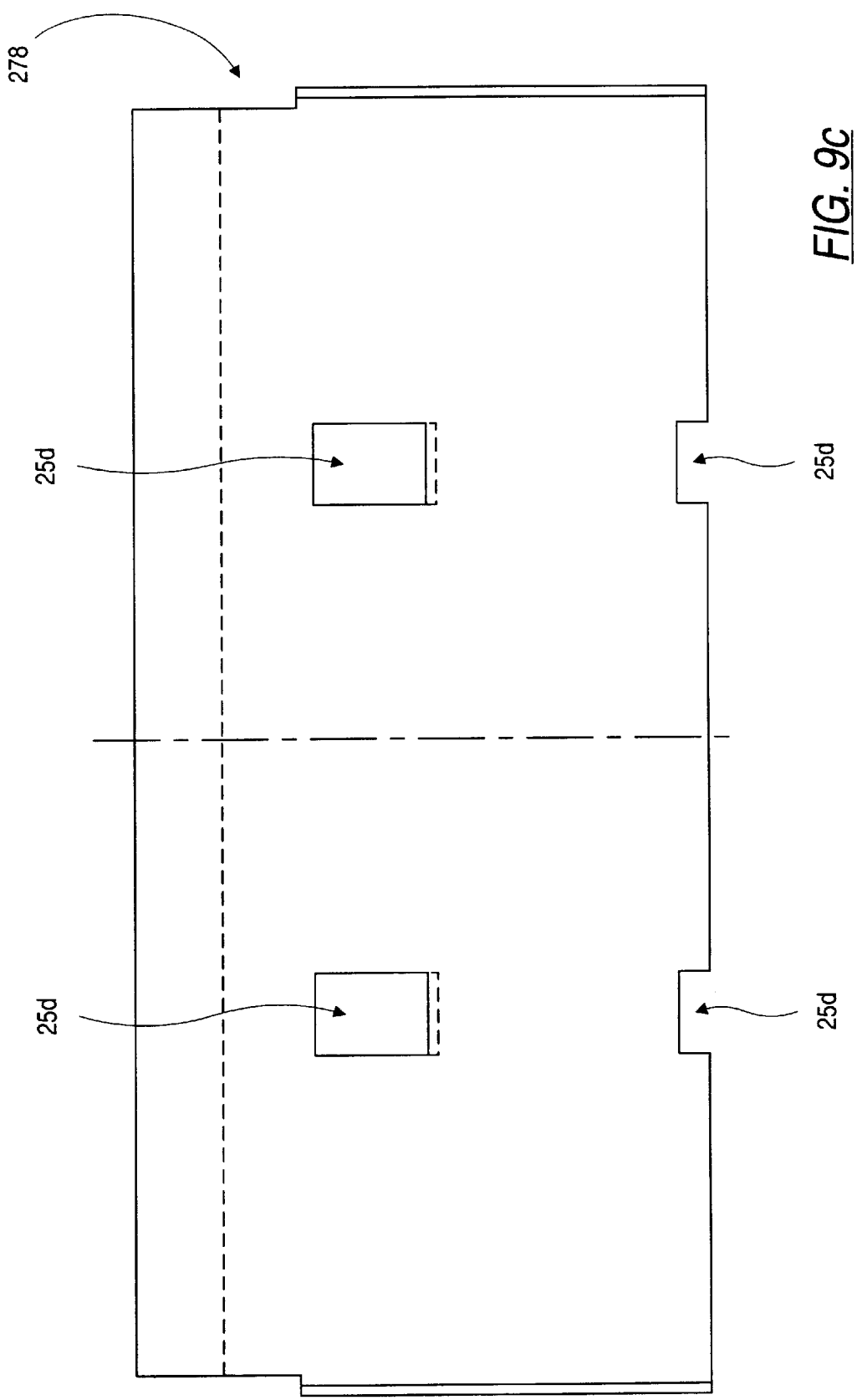
FIG. 9c is a front view of the second follower plate depicted in FIG. 9b.

FIGS. 8a–8c and 9a–9c illustrate, respectively, first and second follower plates 262 and 278. As illustrated, these plates are substantially free from surface features and are substantially smooth like the transport plate 240. The follower plates 262 and 278 are positioned in spaced relation to transport plate 240 so as to define a currency pathway therebetween. The follower plates 262 and 278 and the transport plate such a 240 or 240' contribute to defining a pathway that is free and unencumbered between the roll 251 and the output receptacles 217a and 217b for the bill. As illustrated, the follower plates 262 and 278 have apertures only where necessary for accommodation of passive rolls 268, 270, 284, and 286. The apertures 25c accommodating passive rolls 268 and 270 in the follower plate 262 are shown in FIG. 8c, while the apertures 25d accommodating passive rolls 284 and 286 are shown in FIG. 9c. Thus according to one embodiment a transport mechanism is employed that uses no belts to advance bills from the evaluation region to a plurality of output receptacles.

Referring specifically to FIG. 8a, the follower plate 262 in conjunction with the upper portion of the transport plate 240 guide a bill 20 from the passive roll 251 to a driven roll 264 and then to a driven roll 266. The passive rolls 268, 270 are biased by H-springs 272 and 273 into counter-rotating contact with the corresponding driven rolls 264 and 266 in a manner similar as described above in connection with passive rolls 250 and 251.

A diverter 260 is employed to direct the bill 20 to the appropriate output receptacle 217a or 217b. The bill 20 will encounter the diverter 260 after emerging from between the driven roll 266 and the passive roll 270. Diverter 260 includes a plurality of flanges mounted across the transport path on a shaft 274. Two solenoids 261a,b, one mounted on each end of the shaft 274 (see FIG. 6), cause the shaft and the attached diverter flanges to rotate into either a lower position or an upper position. The two solenoids drive the shaft 274 in opposite directions and an appropriate one of the two solenoids is energized depending upon whether the diverter 260 is to be moved from its lower position to its upper position or vice versa. The use of a separate solenoid for each rotational direction enhances the performance of the diverter 260 by increasing of the speed with which the position of the diverter 260 may be changed.

When the diverter 260 is in the lower position, the ends of the flanges are positioned below the upper surface of the transport plate 240. Apertures 25b in transport plate 240 (see FIGS. 7b and 7d) facilitate this position while apertures 27b in transport plate 240' (see FIG. 11a) facilitate this position. The apertures 25b and 27b correspond in location and size to the diverter 260 which enables the diverter 260 to protrude through the transport plate 240 and create a smooth ramp for directing the bills into the upper output receptacle 217a.

When the diverter 260 is in the upper position (as shown in FIG. 8a), bills are directed between the transport plate 240 and the follower plate 278 (see FIG. 9a). The transport plate 240 and the follower plate 278 guide bills after the diverter 260 to a driven roll 280 and then to a driven roll 282.

Also illustrated in FIG. 8a is a sensor 235a. Sensor 235a may be used to detect when bills pass by the sensor. This sensor may be used to aid in determining when the position of diverter 260 may be changed and/or used to detect when bills have become jammed either upstream of this sensor or over this sensor. For example, if no bills pass this sensor for a predetermined period of time when bills are expected to be passing this sensor, a jam condition error may be generated to stop the transport mechanism and prompt the operator as to the existence and location of a jam. Sensor 235a may be, for example, an optical sensor that detects light reflected off the follower plate 262. A change in the amount of light being reflected back to the sensor 235a may then indicate that a bill is passing by this sensor.

FIG. 9a illustrates a bill 20 between the driven rolls 280 and 282 and their respective passive rolls 284 and 286. The passive rolls 284, 286 are biased by H-springs 288, 289 into passive counter-rotating contact with the driven rolls 280, 282, respectively, in a manner similar to that described above in connection with passive rolls 250, 251. Bills are then directed to the lower output receptacle 217b via the stacker wheels 212b and 213b. Also illustrated in FIG. 9a is a sensor 235b. Sensor 235b may be used to detect when bills pass by the sensor. The above description of sensor 235a in connection with FIG. 8a likewise applies to sensor 235b.

Figure 10A:
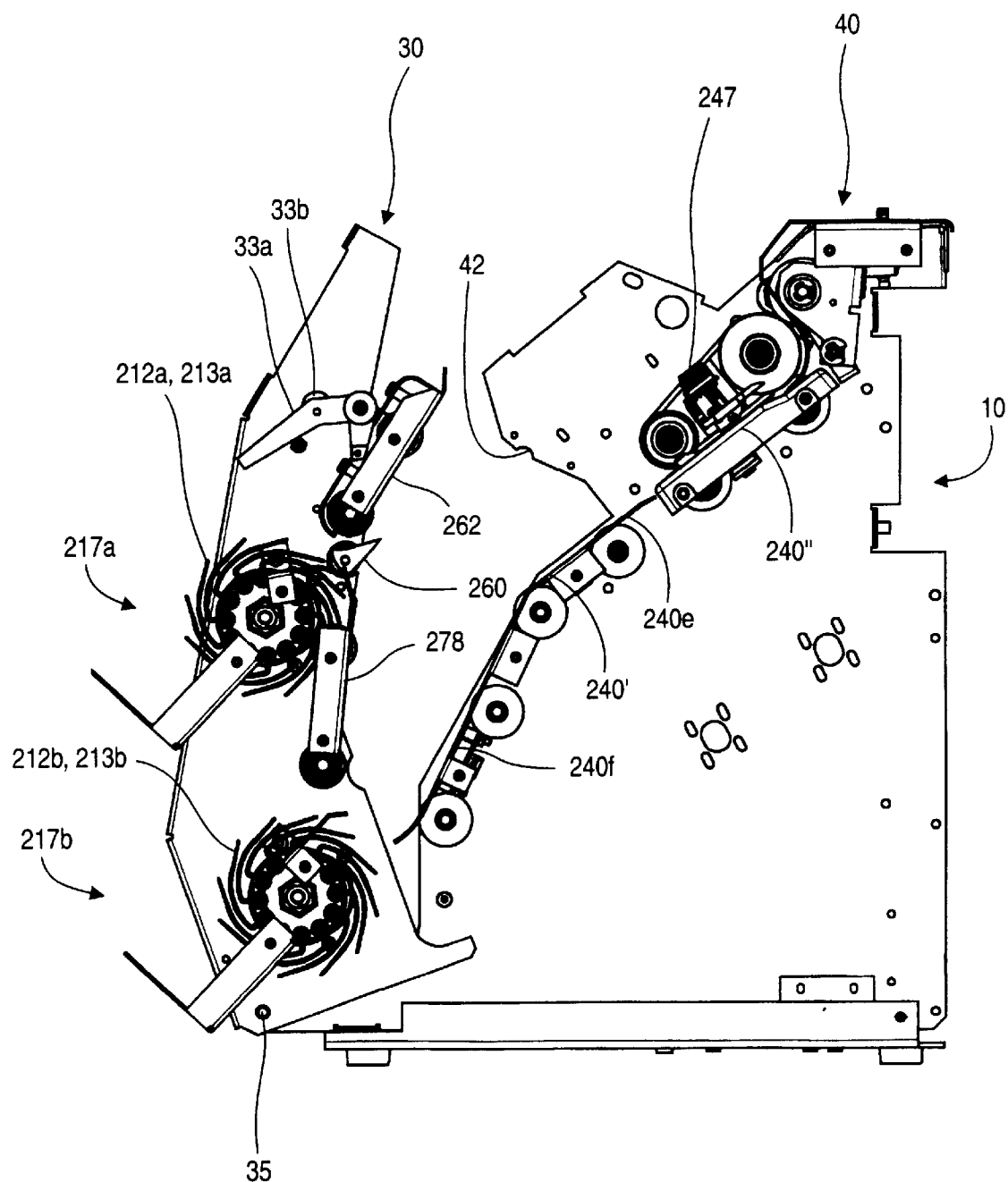
FIG. 10a is a side view depicting an evaluation device in an open position according to one embodiment of the present invention.
Figure 11B:
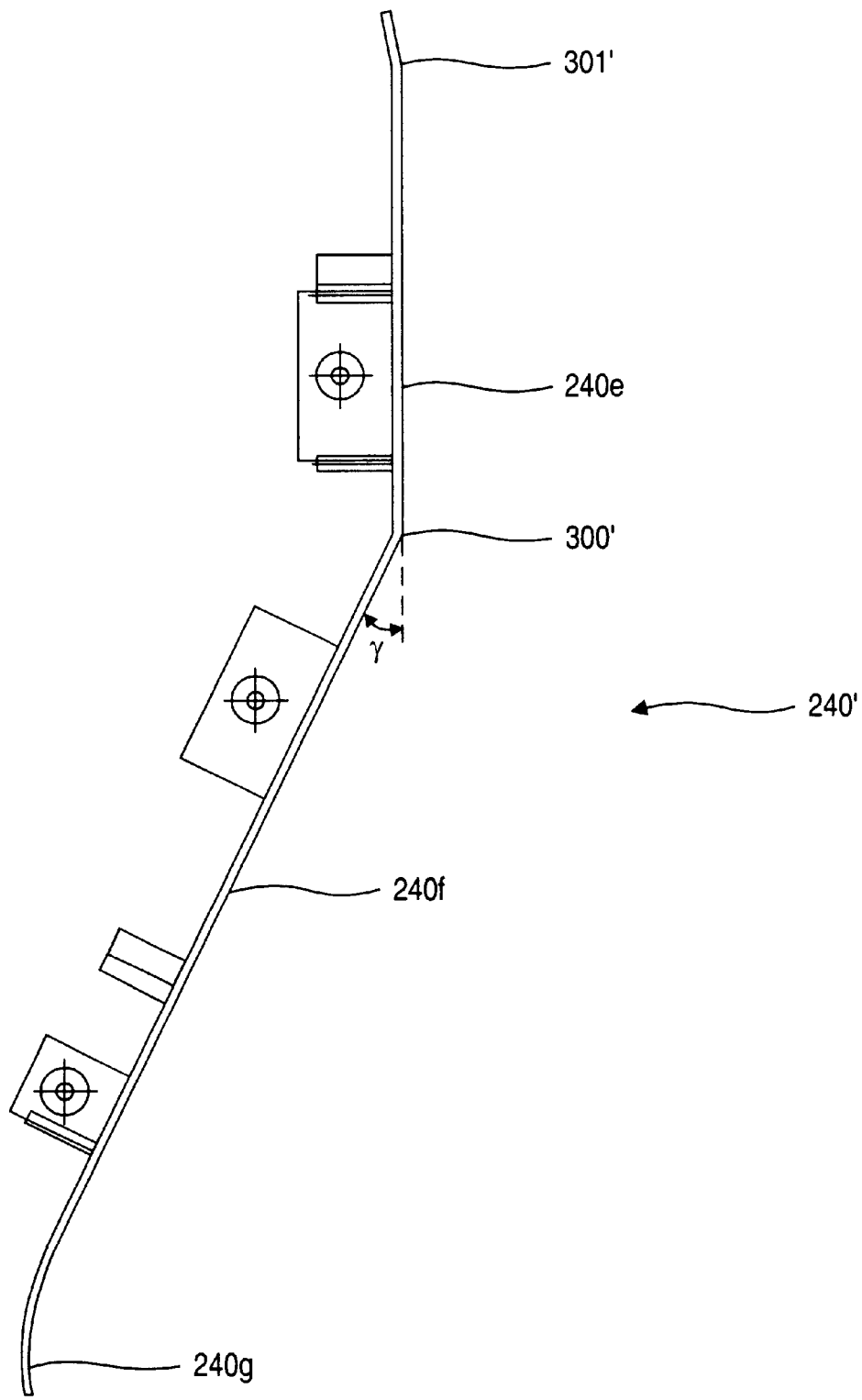
FIG. 11b is a sectional side view of a transport plate according to one embodiment of the present invention.

As shown in FIG. 10a in one embodiment of the invention, the follower plates 262 and 278 are part of an assembly 30 that also includes the output receptacles 217a,b including stacker wheels 212a,b, 213a,b (a moveable assembly 30 can also be seen in phantom in FIG. 2). As shown in FIG. 10a, this assembly 30 can be moved away from the remainder 40 of the document evaluation device 10 which may be, for example, a currency discriminator. Assembly 30 is hingedly connected to the remainder of document evaluation device 40 about pivot 35. This arrangement allows the assembly 30 to rotate outward and away from the remainder of currency discriminator 40 and to expose the transport plate 240', thereby permitting access to the transport plate 240' after the evaluation region 247. In one embodiment, assembly 30 is maintained in its open position by its own weight. Alternatively, springs 320 (see FIG. 2) may be used in conjunction with the pivot 35 to maintain this assembly in its open position. The resulting unobstructed access allows users of the discriminator to easily clear jams without a complicated procedure or the need to put a hand into a restricted, difficult to access, and sometimes dirty region. Likewise, the smooth transport and follower plates contribute to the easy removal of bills.

Assembly 30 in one embodiment of the present invention also includes a pivoting mechanism or lever 33a adjacent to follower plate 262. When in its closed position, the lever 33a is biased upward by a spring (not shown) with a hub 33b fitting into a notch 42 which maintains the assembly 30 in its closed position and the follower plate 262 in spaced relation to transport plate 240e. To move assembly 30 into its open position, the lever 33a is moved downward so that hub 33b is not engaging notch 42. The assembly 30 may then be rotated away from the remainder of the document evaluation device. The lever 33a also assists in moving the assembly 30 away from the remainder of currency discriminator 40.

Figure 10B:
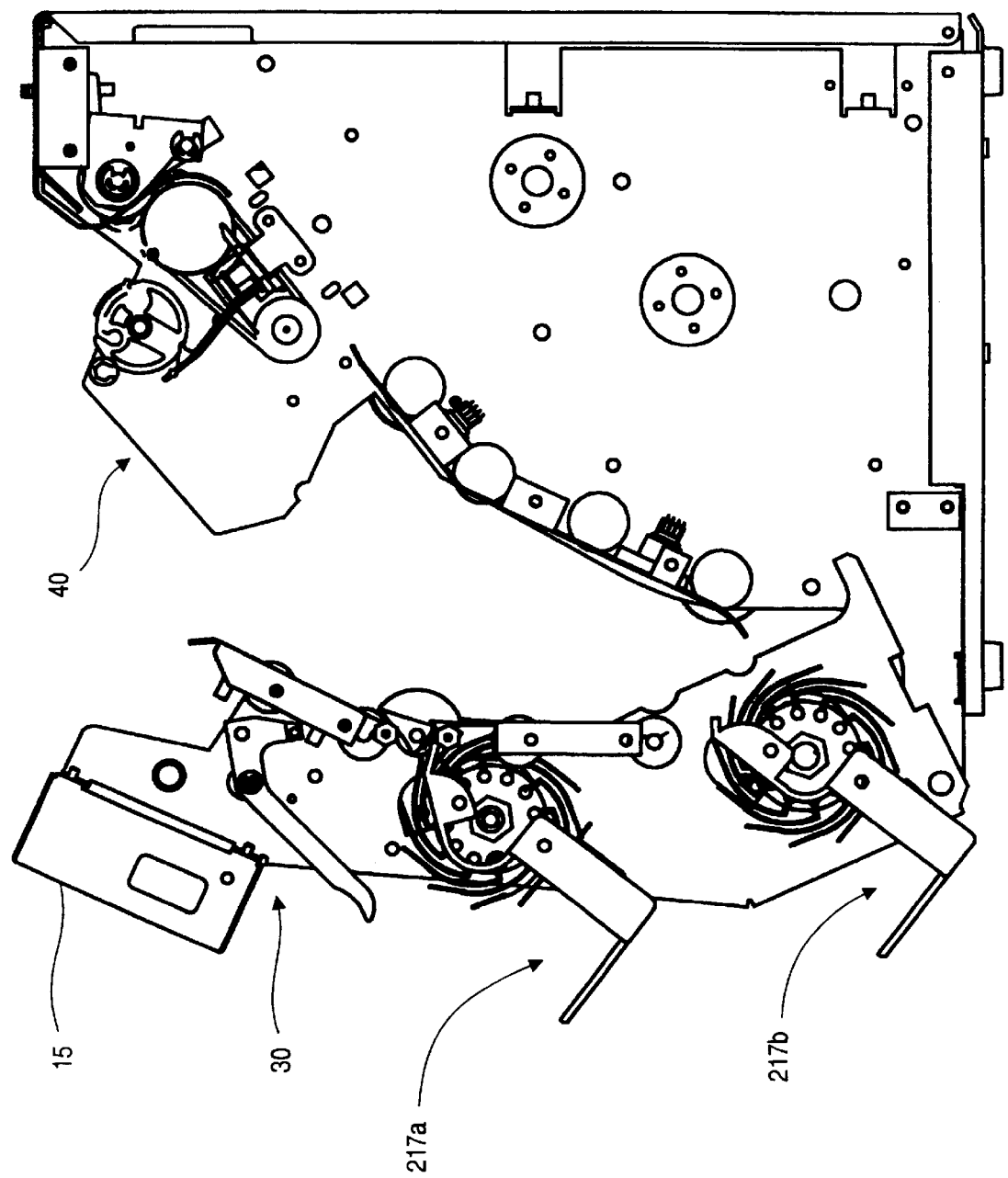
FIG. 10b is a side view depicting an evaluation device in an open position according to one embodiment of the present invention.

FIG. 10b is a side view depicting an evaluation device in an open position according to another embodiment of the present invention that is similar to that shown in FIG. 10a.

Figure 12A:
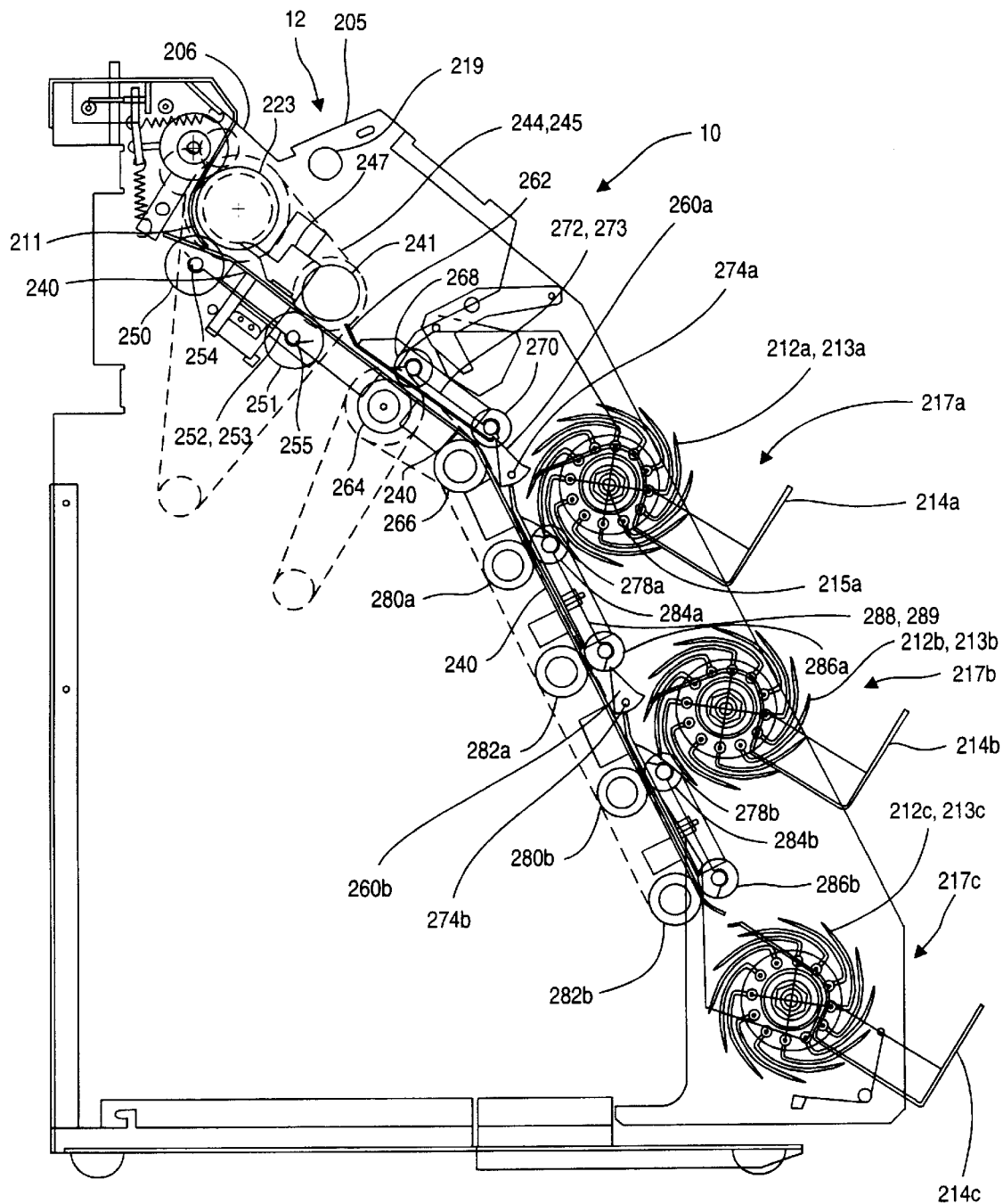
FIG. 12a is a side view of an evaluation device having three output receptacles depicting various transport rolls in side elevation according to one embodiment of the present invention.
Figure 12B:
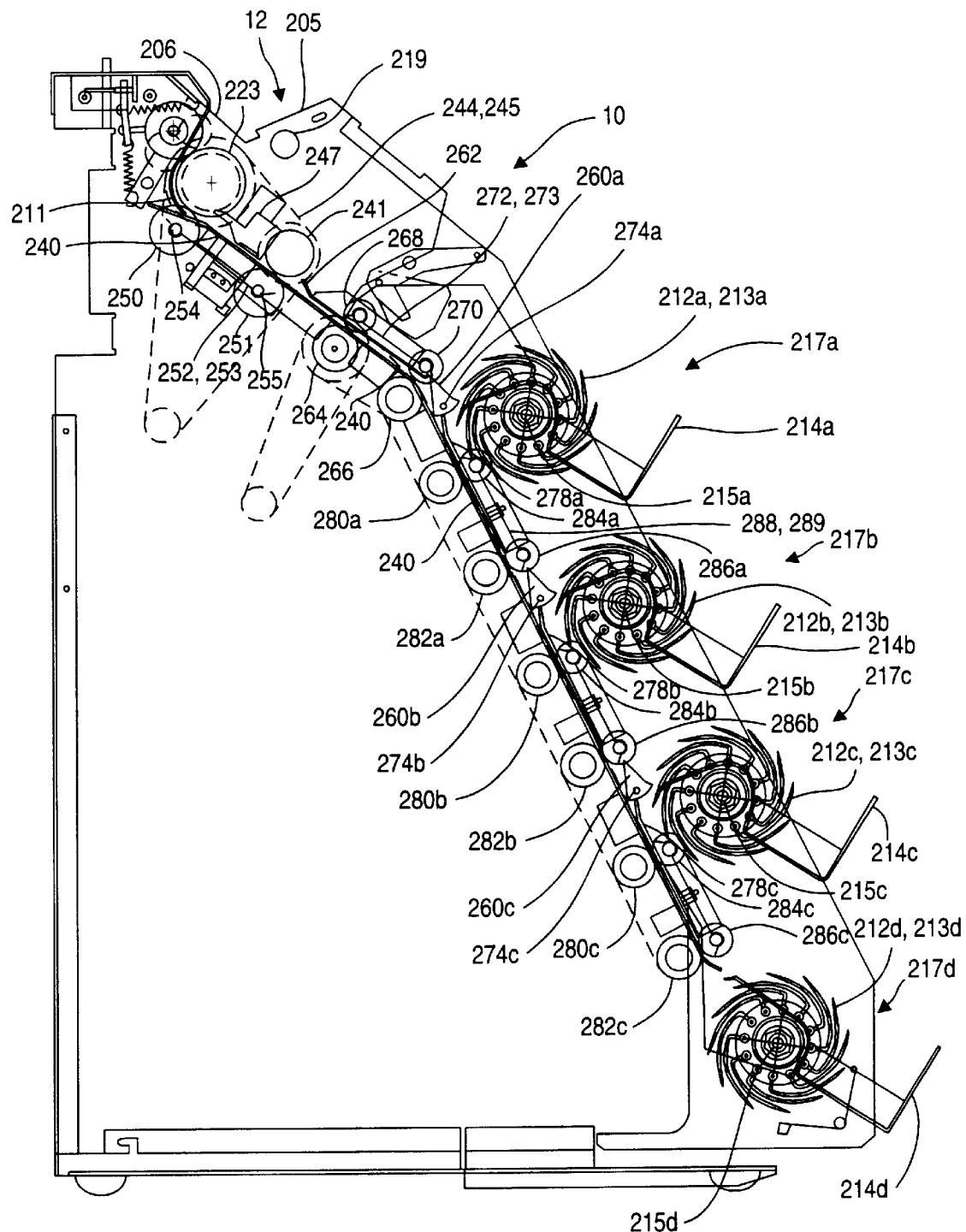
FIG. 12b is a side view of an evaluation device having four output receptacles depicting various transport rolls in side elevation according to one embodiment of the present invention.
Figure 12C:
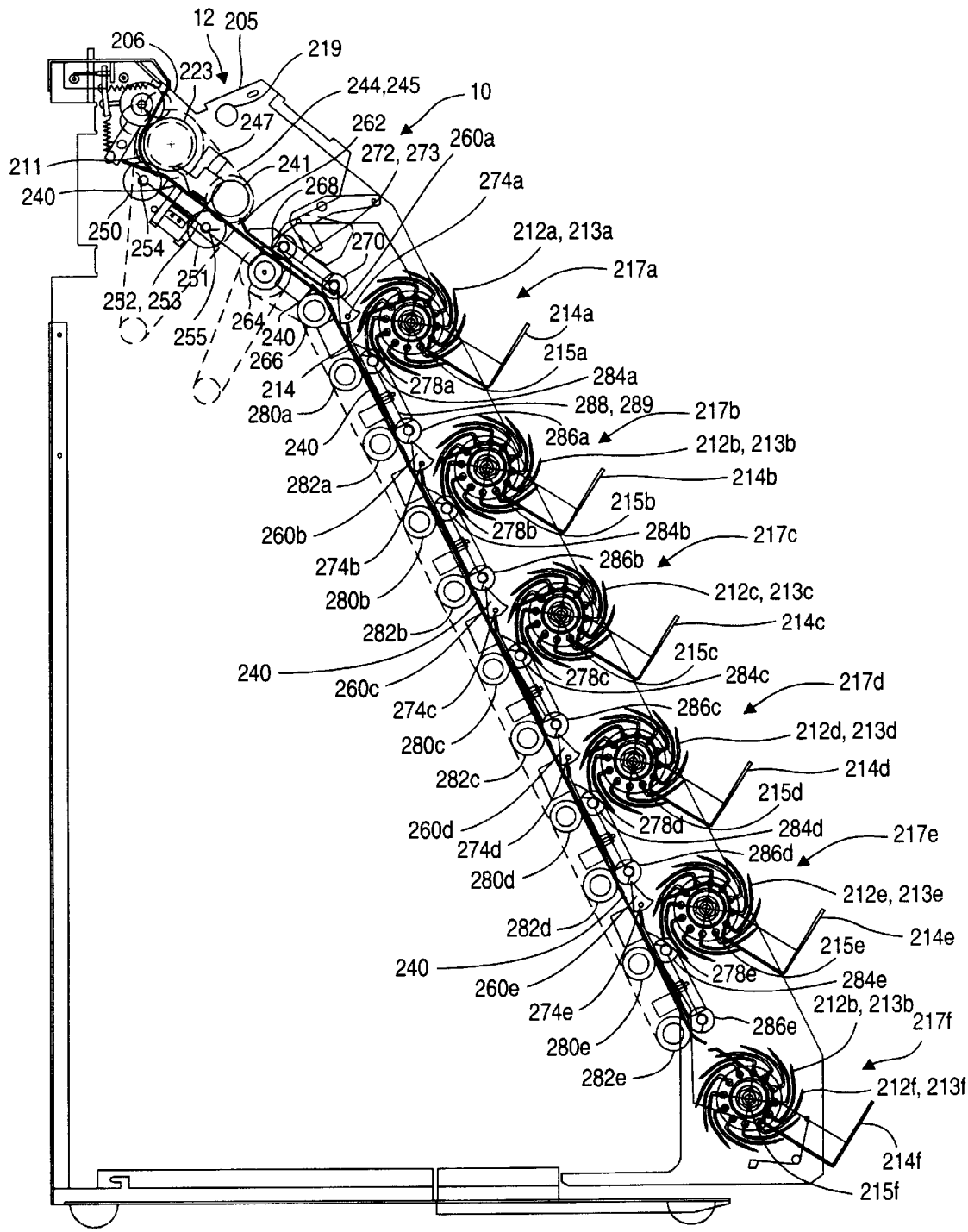
FIG. 12c is a side view of an evaluation device having six output receptacles depicting various transport rolls in side elevation according to one embodiment of the present invention.

FIGS. 12a–c depict multi-pocket document evaluation devices 10, such as a currency discriminators, according to other embodiments of the present invention. FIG. 12a depicts a three-pocket document evaluation device 10, such as a currency discriminator. FIG. 12b depicts a four-pocket document evaluation device 10, such as a currency discriminator. FIG. 12c depicts a six-pocket document evaluation device 10, such as a currency discriminator.

The multi-pocket document evaluation devices 10 in FIGS. 12a–c have a transport mechanism which includes a transport plate or guide plate 240 for guiding currency bills to one of a plurality of output receptacles 217. The transport plate 240 according to one embodiment is substantially flat and linear without any protruding features. Before reaching the output receptacles 217, a bill can be, for example, evaluated, analyzed, authenticated, discriminated, counted and/or otherwise processed.

The multi-pocket document evaluation devices 10 move the currency bills in seriatim from the bottom of a stack of bills along the curved guideway 211 which receives bills moving downwardly and rearwardly and changes the direction of travel to a forward direction. An exit end of the curved guideway 211 directs the bills onto the transport plate 240 which carries the bills through an evaluation section and to one of the output receptacles 217. A plurality of diverters 260 direct the bills to the output receptacles 217. When a diverter 260 is in its lower position, bills are directed to the corresponding output receptacle 217. When a diverter 260 is in its upper position, bills proceed in the direction of the remaining output receptacles.

The multi-pocket document evaluation devices 10 of FIGS. 12a–c according to one embodiment includes passive rolls 250, 251 which are mounted on an underside of the transport plate 240 and are biased into counter-rotating contact with their corresponding driven upper rolls 223 and 241. Other embodiments includes a plurality of follower plates which are substantially free from surface features and are substantially smooth like the transport plate 240. The follower plates 262 and 278 are positioned in spaced relation to transport plate 240 so as to define a currency pathway there between. In one embodiment, follower plates 262 and 278 have apertures only where necessary for accommodation of passive rolls 268, 270, 284, and 286.

The follower plate 262 works in conjunction with the upper portion of the transport plate 240 to guide a bill 20 from the passive roll 251 to a driven roll 264 and then to a driven roll 266. The passive rolls 268, 270 are biased by H-springs into counter-rotating contact with the corresponding driven rolls 264 and 266.

Figure 13:
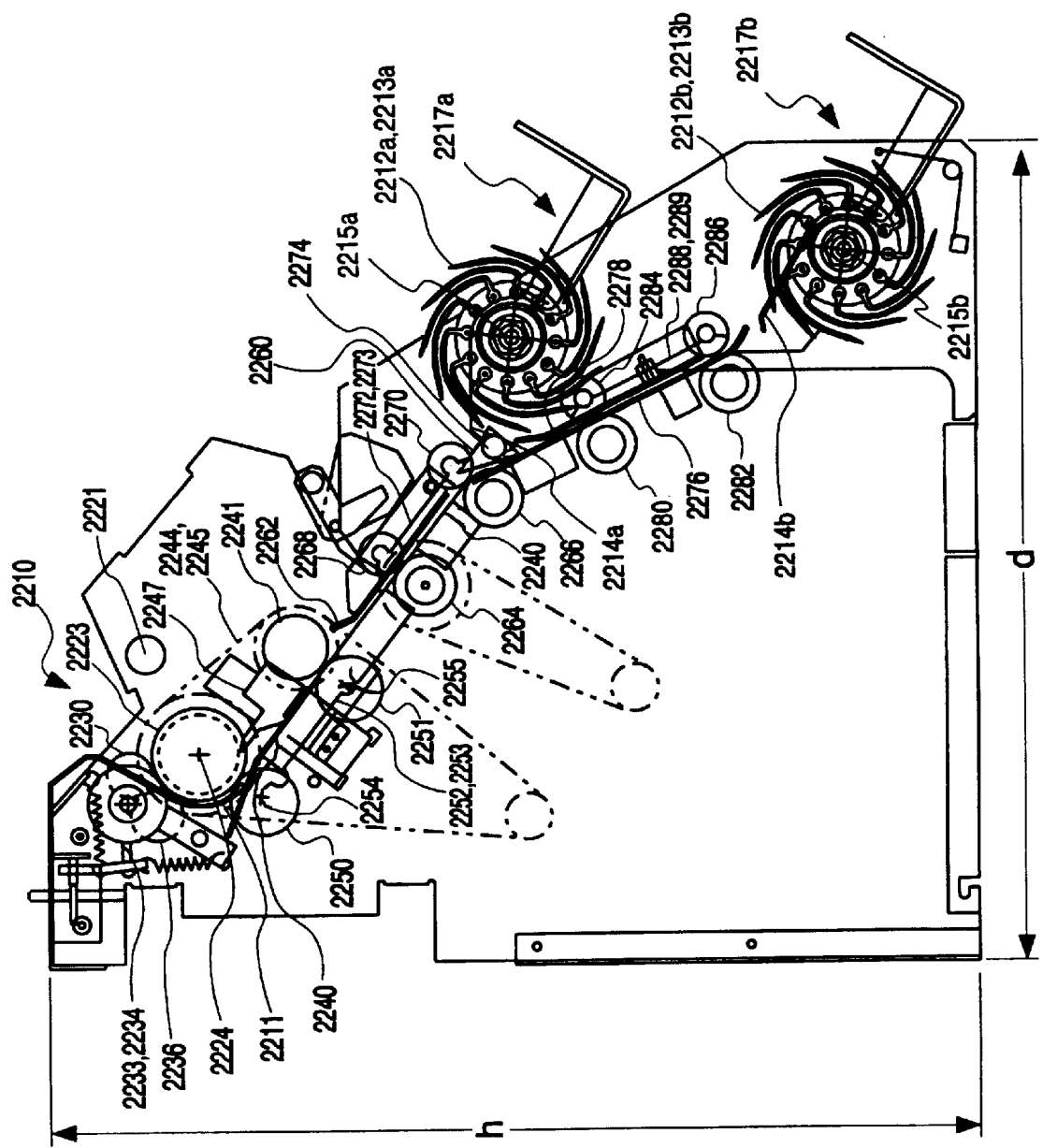
FIG. 13 is a sectional view taken approximately through the center of another embodiment of a currency discriminating machine having two output receptacles showing the various transport rolls in side elevation.
Figure 14B:
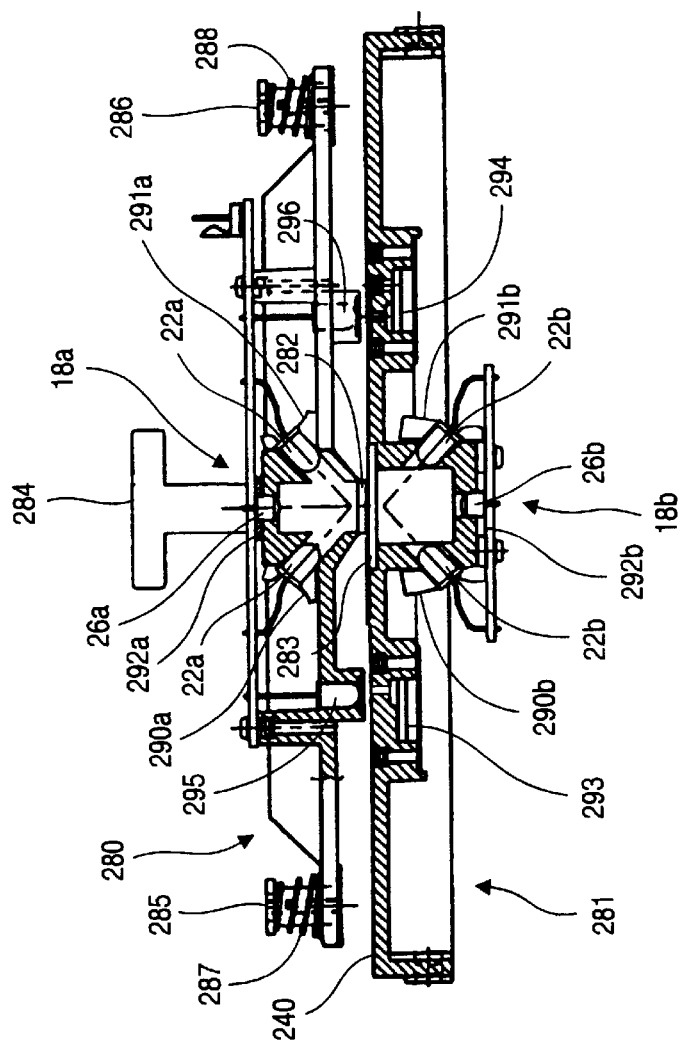
FIG. 14b is an end elevation of a upper support member which includes an upper scanhead and a sectional view of a lower support member mounted beneath a upper support member according to one embodiment.
Figure 14A:
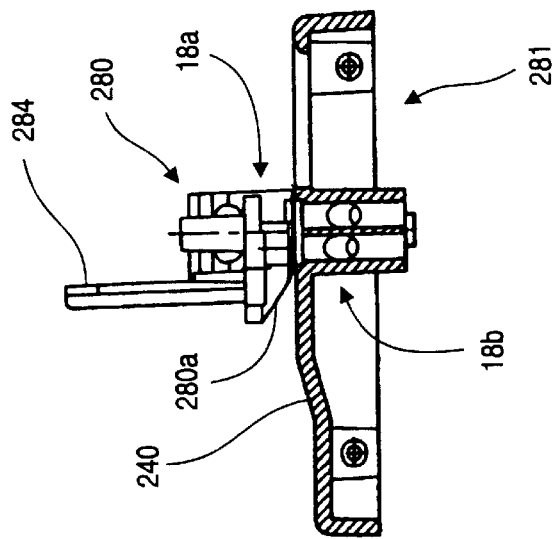
FIG. 14a is a sectional view of a scanhead according to one embodiment.
Figure 15:
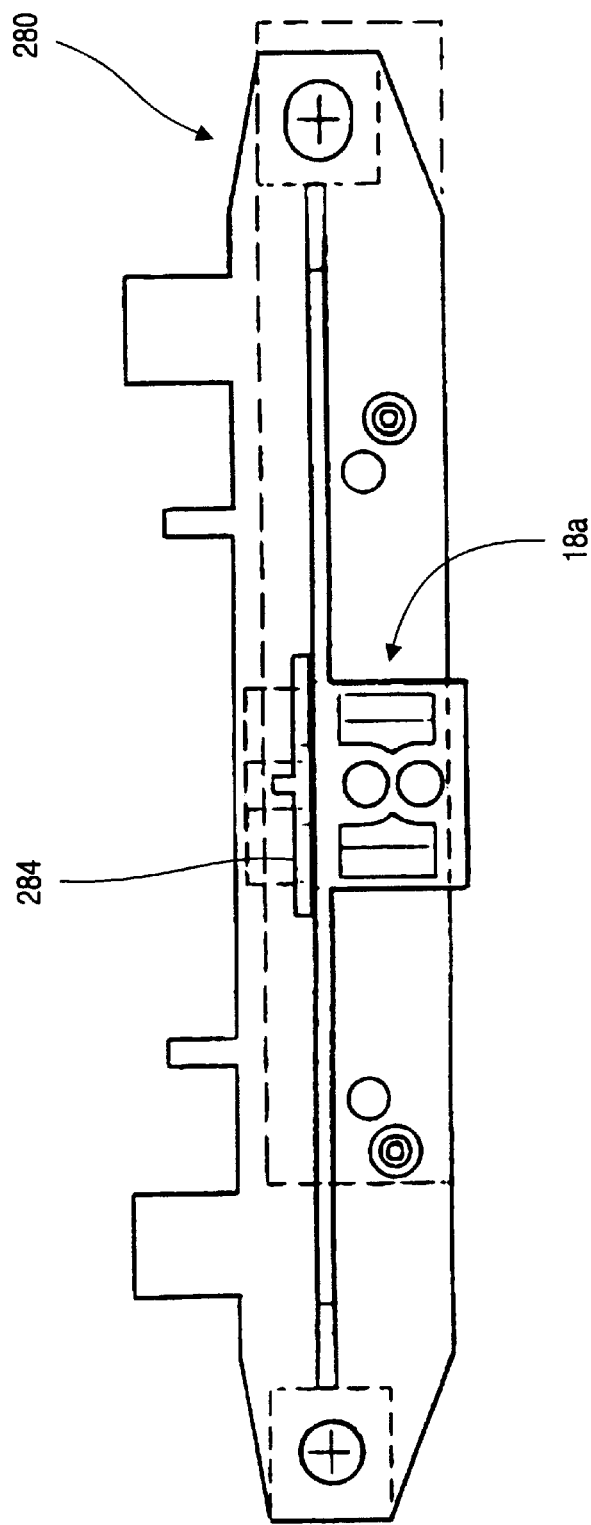
FIG. 15 is a top plan view of an upper support member which includes an upper scanhead according to one embodiment.
Figure 16:
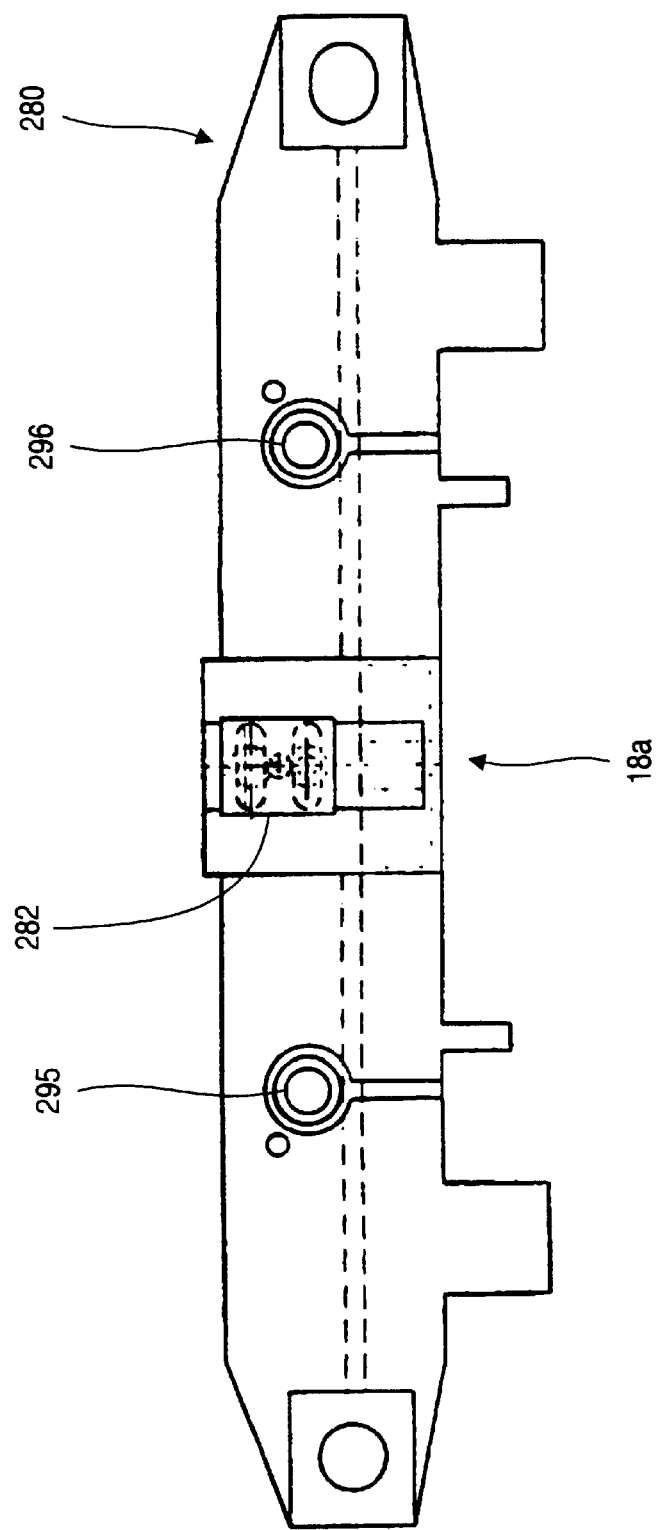
FIG. 16 is a bottom plan view of an upper support member which includes an upper scanhead according to one embodiment.

FIG. 13 is an enlarged vertical section taken approximately through the center of another embodiment of a machine having two output receptacles, 2217a and 2217b, showing various transport rolls in side elevation. A diverter 2260 is provided to direct bills into either receptacle 2217a or 2217b depending upon the results of the denomination discriminating unit and any authenticating means that may be present.

From the input receptacle 2210, the currency bills are moved in seriatim from the bottom of the stack along a curved guideway 2211 which receives bills moving downwardly and rearwardly and changes the direction of travel to a forward direction. The curvature of the guideway 2211 corresponds substantially to the curved periphery of the drive roll 2223 so as to form a narrow passageway for the bills along the rear side of the drive roll. The exit end of the guideway 2211 directs the bills onto a linear path where the bills are scanned. The bills are transported and stacked with the narrow dimension of the bills maintained parallel to the transport path and the direction of movement at all times.

Stacking of the bills is effected in each output receptacle by a pair of driven stacking wheels 2212a and 2213a in output receptacle 2217a and stacking wheels 2212b and 2213b in output receptacle 2217b. These wheels project upwardly through a pair of openings in respective stacker plates 2214a,b. The stacker wheels 2212a,b and 2213a,b are supported for rotational movement about respective shafts 2215a,b journalled on a rigid frame and driven by a motor. The flexible blades of the stacker wheels deliver the bills into a respective one of the output receptacles 2217a,b at the forward end of the respective stacker plates 2214a,b. During operation, a currency bill which is delivered to a respective stacker plate 2214a,b is picked up by the flexible blades and becomes lodged between a pair of adjacent blades which, in combination, define a curved enclosure which decelerates a bill entering therein and serves as a means for supporting and transferring the bill into a respective output receptacle 2217a,b as the stacker wheels 2212a,b and 2213a,b rotate. The mechanical configuration of the stacker wheels, as well as the manner in which they cooperate with the stacker plate, is conventional and, accordingly, is not described in detail herein.

Figure 3:
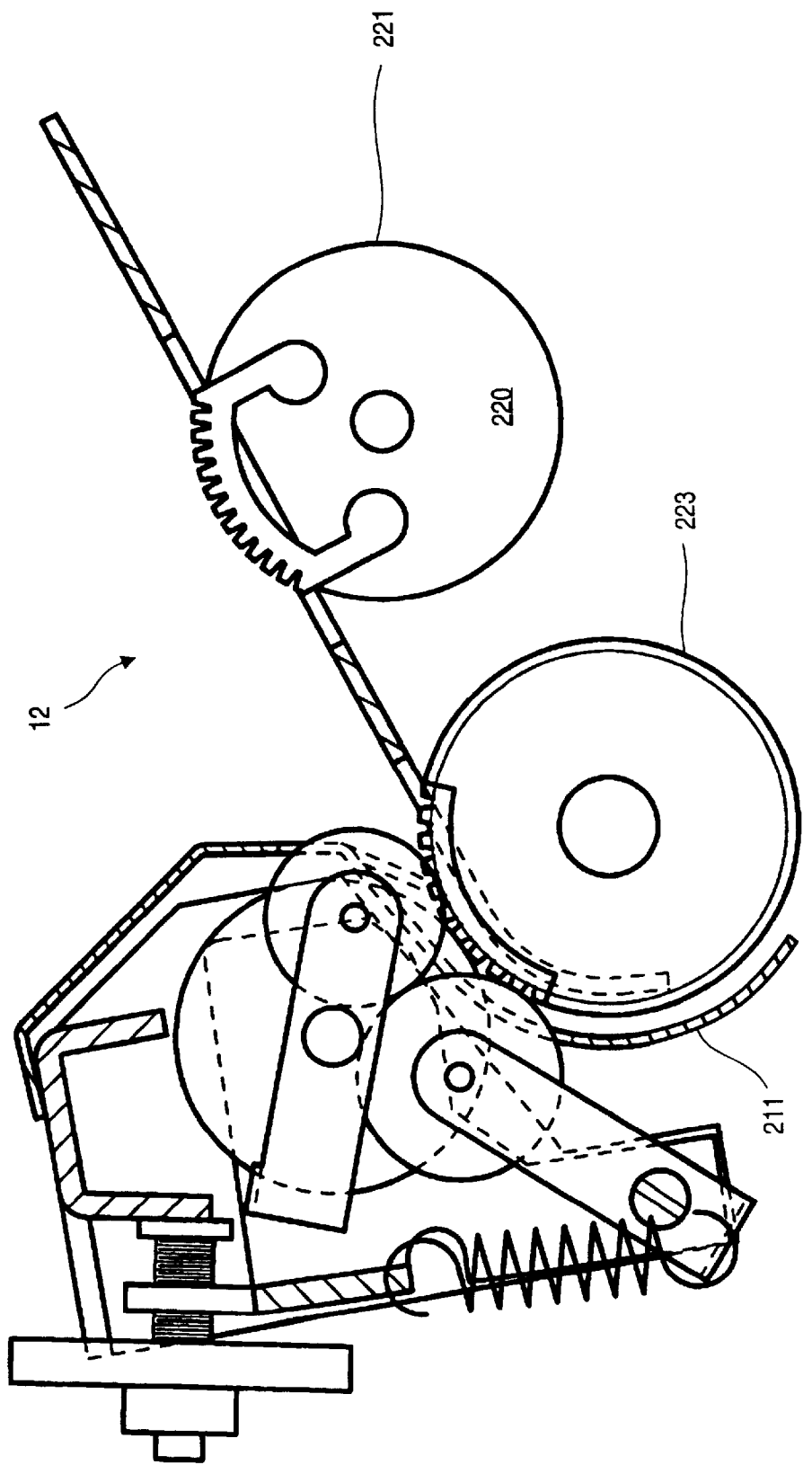
FIG. 3 is a side view depicting a stripping wheel according to one embodiment.

The input region of the machine as shown in FIG. 13 the same as that described in connection with FIG. 3 and according will not be described again here.

The stripping wheels mounted on shaft 2221 feed each bill onto a drive roll 2223 mounted on a driven shaft 2224 supported across the side walls. The drive roll 2223 is the same as drive roll 223 (FIG. 2) described above. Likewise the operation of the stripping wheel and drive roll 2223 is the same as described above in connection with stripping wheels 220 and drive roll 223 (FIG. 3). Likewise, in order to ensure firm engagement between the drive roll 2223 and the currency bill being fed, an idler roll 2230, stripper wheels 2233,2234, and pressure roll 2236 operate as described above in connection with FIG. 3. and in U.S. patent application Ser. No. 08/450,505 filed May 26, 1995, entitled "Method and Apparatus for Discriminating and Counting Documents" which is incorporated by reference in its entirety.

At the lower end of the curved guideway 2211, the bill being transported by the drive roll 2223 engages a flat guide plate 2240. Currency bills are positively driven along the flat plate 2240 by means of a transport roll arrangement which includes the drive roll 2223 at one end of the plate and a smaller driven roll 2241 at the other end of the plate. Both the driver roll 2223 and the smaller roll 2241 include pairs of smooth raised cylindrical surfaces which hold the bill flat against the plate 2240. A pair of O rings 2244 and 2245 fit into grooves formed in both the roll 2241 and the roll 2223 to engage the bill continuously between the two rolls 2223 and 2241 to transport the bill while helping to hold the bill flat against the guide plate 2240.

The flat guide plate 2240 is provided with openings through which the raised surfaces of both the drive roll 2223 and the smaller driven roll 2241 are subjected to counter-rotating contact with corresponding pairs of passive transport rolls 2250 and 2251 having high-friction rubber surfaces. The passive rolls 2250, 2251 are mounted on the underside of the flat plate 2240 in such a manner as to be freewheeling about their axes 2254 and 2255 and biased into counter-rotating contact with the corresponding upper rolls 2223 and 2241. The passive rolls 2250 and 2251 are biased into contact with the driven rolls 2223 and 2241 by means of a pair of H-shaped leaf springs 2252 and 2253. Each of the four rolls 2250, 2251 is cradled between a pair of parallel arms of one of the H-shaped leaf springs 2252 and 2253.

The points of contact between the driven and passive transport rolls are preferably coplanar with the flat upper surface of the plate 2240 so that currency bills can be positively driven along the top surface of the plate in a flat manner. The distance between the axes of the two driven transport rolls, and the corresponding counter-rotating passive rolls, is selected to be just short of the length of the narrow dimension of the currency bills. Accordingly, the bills are firmly gripped under uniform pressure between the upper and lower transport rolls within the area of scanhead 2247, thereby minimizing the possibility of bill skew and enhancing the reliability of the overall scanning and recognition process. The positive guiding arrangement described above is advantageous in that uniform guiding pressure is maintained on the bills as they are transported through the scanhead area, and twisting or skewing of the bills is substantially reduced. This positive action is supplemented by the use of the H-springs 2252, 2253 for uniformly biasing the passive rollers into contact with the active rollers so that bill twisting or skew resulting from differential pressure applied to the bills along the transport path is avoided. The O-rings 2244, 2245 function as simple, yet extremely effective means for ensuring that the central portions of the bills are held flat.

Guide plate 2240 extends from the region of curved guideway 2211 to a region in the vicinity the diverter 2260. A guide plate 2262 in conjunction with the lower portion of the guide plate 2240 guide bills from between rolls 2241 and 2251 to driven roll 2264 and then to driven roll 2266. Passive rolls 2268, 2670 are biased by H-springs 2272,2273 into counter-rotating contact with rolls 2264 and 2266, respectively, in a manner similar to that described above in connection with rolls 2250, 2251. Bills emerge from between rolls 2266 and 2270 and are directed into diverter 2260. Diverter 2260 comprises a plurality of flanges mounted across the transport path on shaft 2274. Two solenoids, one mounted on each end of shaft 2274, cause the shaft and the attached diverter flanges to rotate into either a lower position or an upper position. The two solenoids drive the shaft 2274 in opposite directions and an appropriate one of the two solenoids is energized depending upon whether the diverter 2260 is to be moved from its lower position to its upper position or vice versa. The use of a separate solenoid for each rotational direction enhances the performance of the diverter by increasing the speed with which the position of the diverter may be changed.

When the diverter is in its lower position, bills are directed to the upper output receptacle 2217a via stacker wheels 2212a and 2213a. When the diverter is in its upper position, bills are directed between guide plates 2276 and 2278. Guide plates 2276 and 2278 guide bills from the diverter 2260 to driven roll 2280 and then to driven roll 2282. Passive rolls 2284, 2286 are biased by H-springs 2288,2289 into counter-rotating contact with rolls 2280 and 2282, respectively, in a manner similar to that described above in connection with rolls 2250, 2251. Bills are then directed to the lower output receptacle 2217b via stacker wheels 2212b and 2213b.

Evaluation Region

The characteristics of the evaluation region 247, 2247 may vary according to the particular application and needs of the user. The evaluation region can accommodate a number and variety of different types of sensors depending on a number of variables. These variables are related to whether the machine is authenticating, counting or discriminating and what distinguishing characteristics are being examined, e.g., size, color, magnetism, reflectivity, absorbability, transmissivity, electrical conductivity, etc.

The evaluation region 247, 2247 may employ a variety of detection means such as magnetic or optical sensors. For example, a variety of currency characteristics can be measured using magnetic sensing. These include detection of patterns of changes in magnetic flux (U.S. Pat. No. 3,280,974), patterns of vertical grid lines in the portrait area of bills (U.S. Pat. No. 3,870,629), the presence of a security thread (U.S. Pat. No. 5,151,607), total amount of magnetizable material of a bill (U.S. Pat. No. 4,617,458), patterns from sensing the strength of magnetic fields along a bill (U.S. Pat. No. 4,593,184), and other patterns and counts from scanning different portions of the bill such as the area in which the denomination is written out (U.S. Pat. No. 4,356,473). Additionally, a magnetoresistive sensor or a plurality of such sensors including an array of magnetoresistive sensors may be employed to detect, for example, magnetic flux. Examples of magnetoresistive sensors are described in, for example, U.S. Pat. Nos. 5,119,025, 4,683,508, 4,413,296, 4,388,662, and 4,164,770. Another example of a magnetoresistive sensor that may be used is the Gradiometer available from NVE Nonvolatile Electronics, Inc., Eden Prairie, Minn. Additionally, other types of magnetic sensors may be employed for detecting magnetic flux such as Hall effect sensors and flux gates.

With regard to optical sensing, a variety of currency characteristics can be measured such as detection of density (U.S. Pat. No. 4,381,447), color (U.S. Pat. Nos. 4,490,846, 3,496,370; 3,480,785), length and thickness (U.S. Pat. No. 4,255,651), the presence of a security thread (U.S. Pat. No. 5,151,607) and holes (U.S. Pat. No. 4,381,447), and other patterns of reflectance and transmission (U.S. Pat. No. 3,496,370; 3,679,314; 3,870,629; 4,179,685). Color detection techniques may employ color filters, colored lamps, and/or dichroic beamsplitters (U.S. Pat. Nos. 4,841,358; 4,658,289; 4,716,456; 4,825,246, 4,992,860 and EP 325,364). The use of ultraviolet light is also a useful discrimination and authentication tool. An optical sensing system using ultraviolet light is described in the assignee's co-pending U.S. patent application Ser. No. 08/317,349, filed Oct. 4, 1994, and incorporated herein by reference in its entirety.

In addition to magnetic and optical sensing, other techniques of detecting characteristic information of currency include electrical conductivity sensing, capacitive sensing (U.S. Pat. No. 5,122,754 [watermark, security thread]; 3,764,899 [thickness]; 3,815,021 [dielectric properties]; 5,151,607 [security thread]), and mechanical sensing (U.S. Pat. No. 4,381,447 [limpness]; 4,255,651 [thickness]). Alternatively or additionally, sensors may be employed to detect bills or security threads printed or coated with thermochromatic materials (materials that change color with a change in temperature). Examples of threads incorporating thermochromatic materials are described in U.S. Pat. No. 5,465,301 incorporated herein by reference.

Although not illustrated in the drawings, it should be noted that corresponding photodetectors (not shown) may be provided within the evaluation area in immediate opposition to corresponding light sources. These detectors detect the beam of coherent light directed downwardly onto the bill transport path from corresponding the light sources and generate an analog output which corresponds to the sensed light. Two-sided scanning may be used to permit bills to be fed into a currency discrimination system according to the present invention with either side face up. An example of a two-sided scanhead arrangement is disclosed in U.S. Pat. No. 5,467,406, incorporated herein by reference in its entirety. Another example of a two-sided scanhead arrangement is described in co-pending U.S. patent application Ser. No. 08/450,505 referred to above and incorporated by reference in its entirety. Further, to accommodate scanning in areas other than the central portion of a bill, multiple scanheads may be laterally positioned next to each other. Examples of multiple scanhead arrangements are described in co-pending U.S. patent application Ser. No. 08/287,882 incorporated herein by reference in its entirety.

Some examples of scanheads are depicted in FIGS. 13–16. These scanheads may be, for example, incorporated into the evaluation devices depicted in FIGS. 1, 3, 10a–10b and 12a–12c. As illustrated in FIGS. 13–16, the housing for each scanhead is formed as an integral part of a unitary molded plastic support member 280 or 281. The lower member 281 also forms the transport plate 240 that receives the bills from the drive roll 223 and supports the bills as they are driven past the scanheads 18a and 18b.

The two support members 280 and 281 are mounted facing each other so that the lenses 282 and 283 of the two scanheads 18a, 18b define a narrow gap through which each bill is transported. The upper support member 280 includes a tapered entry guide 280a which guides an incoming bill into the gaps between the various pairs of opposed lenses.

The lower support member 281 is attached rigidly to the machine frame. The upper support member 280, however, is mounted for limited vertical movement when it is lifted manually by a handle 284, to facilitate the clearing of any paper jams that occur beneath the member 280. To allow for such vertical movement, the member 280 is slidably mounted on a pair of posts 285 and 286 on the machine frame, with a pair of springs 287 and 288 biasing the member 280 to its lowermost position.

Each of the two optical scanheads 18a and 18b housed in the support members 280, 281 includes a pair of light sources acting in combination to uniformly illuminate light strips of the desired dimension on opposite sides of a bill as it is transported across the plate 240. Thus, the upper scanhead 18a includes a pair of LEDs 22a, directing light downwardly through an optical mask on top of the lens 282 onto a bill traversing the flat guide plate 240 beneath the scanhead. The LEDs 22a are angularly disposed relative to the vertical axis of the scanhead so that their respective light beams combine to illuminate the desired light strip defined by an aperture in the mask. The scanhead 18a also includes a photodetector 26a mounted directly over the center of the illuminated strip for sensing the light reflected off the strip. A lower scanhead 18b includes a pair of LEDs 22b, directing light upwardly through an optical mask on top of the lens 283 onto a bill traversing the flat guide plate 240 above the scanhead.

Figure 17:
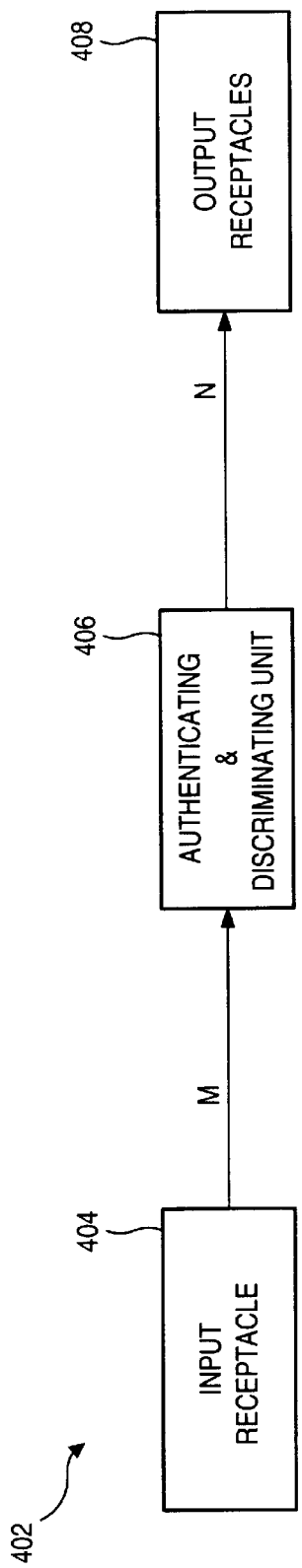
FIG. 17 is a functional block diagram illustrating a document authenticator and discriminator according to one embodiment of the present invention.

Turning now to FIG. 17, there is shown a functional block diagram illustrating an embodiment of a document authenticator and discriminator according to the present invention. The discriminator system 402 comprises an input receptacle 404 for receiving a stack of currency bills. A transport mechanism defining a transport path (as represented by arrow M) transports the bills in the input receptacle, one at a time, past one or more sensors of an authenticating and discriminating unit 406. Bills are then transported to one of a plurality of output receptacles 408 (arrow N). The system 402 may correspond, for example, to the discriminators described above having multiple output pockets such as those shown in FIGS. 1–2, 10a–10b, and 12a–12c. The authenticating and discriminating unit scans and determines the denomination of each passing bill. Any variety of discriminating techniques may be used. For example, the discriminating method disclosed in U.S. Pat. No. 5,295,196 (incorporated by reference herein in its entirety) may be employed to optically scan each bill. Depending on the characteristics of the discriminating unit employed, the discriminator may be able to recognize bills only if fed face up or face down, regardless of whether fed face up or face down, only if fed in a forward orientation or reverse orientation, regardless of whether fed in a forward or reverse orientation, or some combination thereof. Additionally, the discriminating unit may be able to scan only one side or both sides of a bill. In addition to determining the denomination of each scanned bill, the authenticating and discriminating unit 406 may additionally include various authenticating tests such as an ultraviolet authentication test as disclosed in U.S. patent application Ser. No. 08/317,349 filed on Oct. 4, 1994 for a "Method and Apparatus for Authenticating Documents Including Currency" incorporated herein by reference in its entirety. Likewise, the authenticating and discriminating unit 406 may additionally include other authentication tests such as thread detection, enhanced magnetics tests, and color authentication tests including those described in co-pending U.S. patent application Ser. No. 08/800,053, filed on Feb. 14, 1997 entitled "Method and Apparatus for Document Identification and Authentication" incorporated herein by reference in its entirety.

Signals from the authenticating and discriminating unit 406 are sent to a signal processor such as a central processor unit ("CPU"). The CPU records the results of the authenticating and discriminating tests in a memory. When the authenticating and discriminating unit 406 is able to confirm the genuineness and denomination of a bill, the value of the bill is added to a total value counter in memory that keeps track of the total value of the stack of bills that were inserted in the input receptacle 404 and scanned by the authenticating and discriminating unit 406. Additionally, depending on the mode of operation of the discriminator system 402, counters associated with one or more denominations may be maintained in the memory. For example, a $1 counter may be maintained to record how many $1 bills were scanned by the authenticating and discriminating unit 406. Likewise, a $5 counter may be maintained to record how many $5 bills were scanned, and so on. In an operating mode where individual denomination counters are maintained, the total value of the scanned bills may be determined without maintaining a separate total value counter. The total value of the scanned bills and/or the number of each individual denomination may be displayed on a display such as a monitor or LCD display.

A discriminating unit such as the authenticating and discriminating unit 406 may not be able to identify the denomination of one or more bills in the stack of bills loaded into the input receptacle 404. For example, if a bill is excessively worn or soiled or if the bill is torn a discriminating unit may not be able to identify the bill. Furthermore, some known discrimination methods do not have a high discrimination efficiency and thus are unable to identify bills which vary even somewhat from an "ideal" bill condition or which are even somewhat displaced by the transport mechanism relative to the scanning mechanism used to discriminate bills. Accordingly, such poorer performing discriminating units may yield a relatively large number of bills which are not identified. Alternatively, some discriminating units may be capable of identifying bills only when they are fed in a predetermined manner. For example, some discriminators may require a bill to be faced in a predetermined manner. Accordingly, when a bill is fed face down past a discriminating unit which can only identify bills fed face up, the discriminating unit can not identify the bill. Likewise, other discriminators require a specific edge of a bill to be fed first, for example, the top edge of a bill. Accordingly, bills which are not fed in the forward direction, that is, those that are fed in the reverse direction, are not identified by such a discriminating unit.

According to one embodiment, the discriminator system 402 is designed so that when the authenticating and discriminating unit is unable to identify a bill, the unidentified note is "presented" in one of the output receptacles, that is, the transport mechanism is stopped so that the unidentified bill is located at a predetermined position within one of the output receptacles, such as being the last bill transported to one of the output receptacles. For example, where the unidentified bill is the last bill transported to an output receptacle, it may be positioned within the stacker wheels or positioned at the top of or at the rear of the stack of bills resting on a stacker plate in the output receptacle 408. The output receptacles 408 are preferably positioned within the discriminator system 402 so that the operator may conveniently see the flagged bill and/or remove it for closer inspection. Accordingly, the operator is able to easily see the bill which has not been identified by the authenticating and discriminating unit 406. The operator may then either visually inspect the flagged bill while it is resting on the top of or at the rear of the stack, or alternatively, the operator may chose to remove the bill from the output receptacle in order to examine the flagged bill more closely.

According to another embodiment, when a bill is flagged, the transport mechanism may be stopped before the flagged bill is transported to one of the output receptacles. Such an embodiment is particularly suited for situations in which the operator need not examine the bill being flagged, such as upon the occurrence of a denomination change or separate series error described below. For example, upon the occurrence of a denomination change where all available output receptacles already have one or more bills in them, the machine may stop with the denomination change bill residing within the transport mechanism. The machine may then prompt the operator to remove all the bills from a given output receptacle. When the operator does so, the machine automatically resumes operation (or alternatively, the machine may resume operation after the selection of a continue key) and delivers the denomination change bill into the cleared output receptacles.

The discriminator system 402 may be designed to continue operation automatically when a flagged bill is removed from the output receptacle or, according to one embodiment of the present invention, may be designed to require a selection element to be depressed. Upon examination of a flagged bill by the operator, it may be found that the flagged bill is genuine even though it was not identified by the discriminating unit. However, because the bill was not identified, the total value and/or denomination counters in the memory will not reflect its value. According to one embodiment, such an unidentified bill is removed from the output stack and either re-fed through the discriminator or set aside. In the latter case, any genuine set aside bills are counted by hand.

In order to avoid problems associated with re-feeding bills, counting bills by hand, and adding together separate totals, according to one embodiment of the present invention, a number of selection elements associated with individual denominations are provided. These selection elements may be in the form of keys or buttons of a keypad. Other types of selection elements such as switches or displayed keys in a touch-screen environment may be employed. When an operator determines that a flagged bill is acceptable, the operator may simply depress the selection element associated with the denomination of the flagged bill and the corresponding denomination counter and/or the total value counter are appropriately incremented and the discriminator system 402 resumes operating again. In non-automatic restart discriminators, where an operator has removed a genuine flagged bill from the output receptacle for closer examination, the bill is first replaced into the output receptacle before a corresponding selection element is chosen.

An advantage of the above described procedure is that appropriate counters are incremented and the discriminator is restarted with the touch of a single key, greatly simplifying the operation of the discriminator system 402 while reducing the opportunities for human error. When an operator determines that a flagged bill is not acceptable, the operator may remove the unacceptable flagged bill from the output receptacle without replacement and depress a continuation key on the keypad. When the continuation key is selected, the denomination counters and the total value counter are not affected and the discriminator system 402 will resume operating again. In automatic restart discriminators, the removal of a bill from the output receptacle is treated as an indication that the bill is unacceptable and the discriminator automatically resumes operation without affecting the denomination counters and/or total value counters.

With respect to FIG. 17, in one embodiment, where the authenticating and discriminating unit determines that a bill is a fake, the flagged bill is routed to a separate one of said output receptacles. The operation of the discriminator may or may not then be suspended. When a bill is not determined to be fake but for some reason the authenticating and discriminating unit 406 is not able to identify the denomination of the bill, the no call bill may be transported one of the output receptacles. In one embodiment, no call bills are transported to a separate one of the output receptacles. In another embodiment, no calls are not delivered to a special separate output receptacle. The operation of the discriminator may or may not then be suspended.

In another embodiment according to FIG. 17, no call bills are delivered to an output receptacle separate from the one or more output receptacles receiving identified bills. The operation of the discriminator need not be suspended until all the bills placed in the input receptacle have been processed. The value of any no call bills may then be added to the appropriate counters after the stack of bills has been processed through a reconciliation process.

One embodiment that may be used for stopping the transport mechanism in response to the detection of an unidentified bill or a bill meeting some other criteria such as being a suspect bill, denomination change, etc., is described in more detail in U.S. Pat. No. 5,295,196 incorporated herein by reference in its entirety. Basically, one or more sensors retrieve information from passing bills. This information is processed by a signal processor such as a CPU. The position of bills in the transport mechanism is monitored. This monitoring of bill positioned is accomplished via the use of an optical encoder as described in U.S. Pat. No. 5,295,196. If the denomination of the bill is identified, the signal processor generates a signal indicative of the determined denomination. If the denomination of the bill is not determined, the signal processor generates a no call signal. If the signal processor determines the bill to be suspect, a suspect signal is generated or a particular type of suspect signal is generated indicative of the reason why the bill is believed to be suspect, e.g., failure of a magnetic test, failure of a UV test, etc. Additionally, error signals may be generated for other reasons including the detection of various minor errors such as a denomination change or stranger condition or the detection a major error such as doubles or chains. As a result of the generation of one or more of these error signals, the signal processor can be programmed to generate one or more signals that cause the transport mechanism to halt in a particular manner such as by sending appropriate signals to the motor driving the transport mechanism and/or to cause one or more diverters to direct bills toward an appropriate output receptacle such as by sending appropriate signals to the diverter driving mechanisms such as the solenoids described above. Positional information obtained from the encoder may be employed to stop a bill in a controlled manner and so that the bill is stopped in a predetermined position or identifiable location.

Figure 18:
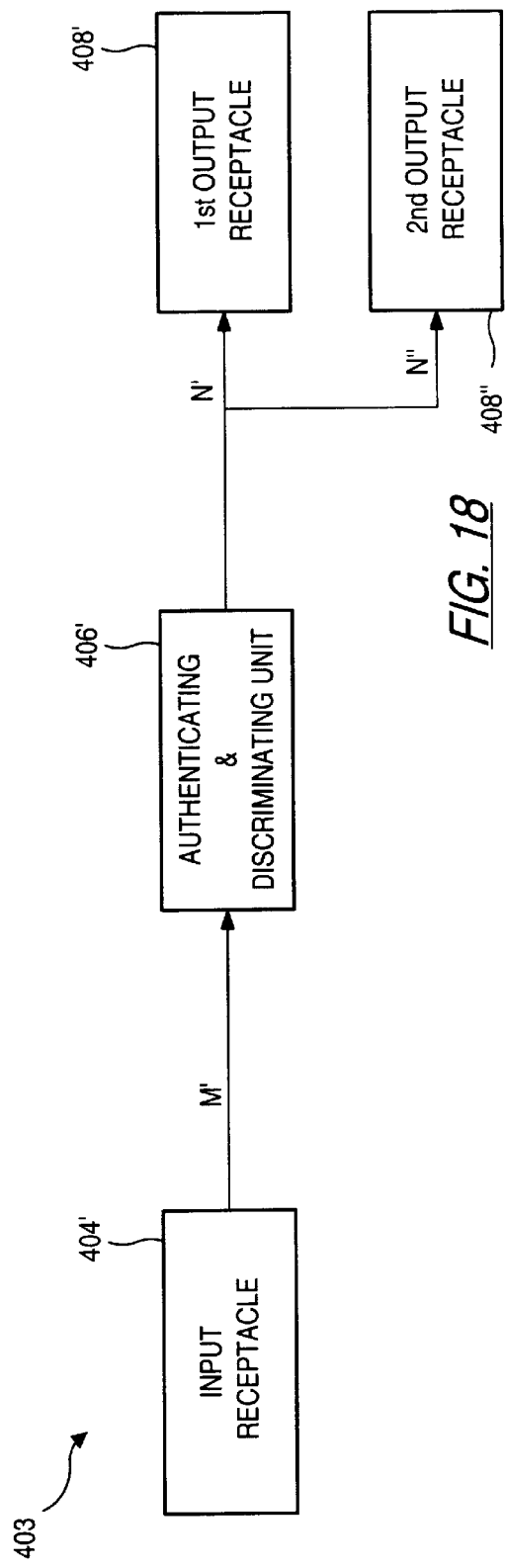
FIG. 18 is a functional block diagram illustrating a two-pocket document authenticator and discriminator according to one embodiment of the present invention.

Turning now to FIG. 18, there is shown a functional block diagram illustrating a two-pocket document authenticator and discriminator according to one embodiment of the present invention. The discriminator system 403 comprises an input receptacle 404' for receiving a stack of currency bills. A transport mechanism defining a transport path (as represented by arrow M') transports the bills in the input receptacle, one at a time, past one or more sensors of an authenticating and discriminating unit 406'. Bills are then transported to one of two output receptacles 408', 408" (as represented by arrows N', N").

In one embodiment, where the authenticating and discriminating unit 406 determines that a bill is a fake, the flagged bill is routed to a specific one of the output receptacles. The operation of the discriminator may or may not then be suspended. When a bill is not determined to be fake but for some reason the authenticating and discriminating unit 406 is not able to identify the denomination of the bill, the no call bill may be transported to one of the output receptacles 408', 408".

In one embodiment, no call bills are transported to a specific one of the output receptacles 408', 408". In another embodiment, no call bills are not delivered to a special separate output receptacle. The operation of the discriminator may or may not then be suspended. For example, in a two output pocket discriminator, all bills may be transported to the same output receptacle regardless of whether they are determined to be suspect, no call, or properly identified. In this example, the operation of the discriminator may be suspended and an appropriate message displayed when a suspect or no call bill is encountered. Alternatively, suspect bills may be delivered to a specific one of the two output receptacles (i.e., a reject receptacle) and no calls and identified bills may be sent to the other output receptacle. In this example, the operation of the discriminator need not be suspended when a suspect bill is encountered but may be suspended when a no call bill is encountered. If the operation is suspended at the time the no call bill is detected and the operator determines that the no call bill is acceptable, the operator returns the bill to the output receptacle from which it was removed (if it was removed) and selects a selection element (not shown) corresponding to the denomination of the flagged bill. Appropriate counters (not shown) are incremented, the discriminator system 403 resumes operation. On the other hand, if the operator determines that the flagged bill is unacceptable, the operator removes the bill without replacement from the output receptacle and selects a continuation element (not shown). The discriminator system 403 resumes operation without incrementing the counters associated with the various denomination and/or the total value counters.

In another embodiment, no call bills are delivered to a specific output receptacle separate from the output receptacle receiving identified bills. The operation of the discriminator need not be suspended until all the bills placed in the input receptacle 404 have been processed. Alternatively, the operation of the discriminator need not be suspended when a no call is encountered but may be suspended when a suspect bill is detected so that the operator may remove any suspect bills from the discriminator. The value of any no call bills may then be added to the appropriate counters after the stack of bills has been processed through a reconciliation process. In an alternate embodiment, suspect and no call bills may be delivered to a specific one of the two output receptacles (i.e., a reject receptacle) and identified bills may be sent to the other output receptacle. Additionally, according to this embodiment, the operation of the discriminator may be suspended and an appropriate message displayed when a suspect or no call bill is encountered.

As described above in connection with FIG. 17, when the transport mechanism is to be stopped in response to a bill being flagged, the flagged bill may be located at a predetermined position within an output receptacle, e.g., last bill, in stacker wheel, or alternatively, the transport mechanism may be stopped before the flagged bill is transported to one of the output receptacles.

The system 403 may correspond, for example, to the discriminators described above having two output pockets such as those shown in FIGS. 1–2, and 10*a*–10*b*. In one embodiment, the discrimination system is selectively programmable among several operating modes so that an operator may select, for example, which bills to flag, in which pocket to direct the flagged or unflagged bills, and/or which stopping conditions to activate or de-activate. The several operating modes will be discussed in detail below. In any of the selected operating modes, the system may be programmed to deliver a flagged bill into a selected pocket and suspend operation of the machine to allow for inspection of the bill, as described in relation to FIG. 17, or the machine may be programmed to "off-sort" flagged or unflagged bills into a different pocket and either stop to allow for inspection of the "off-sorted" bill or continue processing the stack of bills without stopping.

A bill may be flagged and the discriminator systems described above such as those in conjunction with FIGS. 1–2, 10*a*–10*b*, 12*a*–12*c*, and 17–18 may be stopped upon encountering an unidentified or "no call" bill, as discussed above, or for any number of other stopping conditions. In general, these discriminator systems may stop upon the occurrence of minor errors or major errors, both of which will be discussed in detail below. These discriminator systems may include an audio alarm to provide an audible signal upon the occurrence of one or more of the minor or major error conditions. Preferably, the audio alarm is programmable to permit the operator to selectively activate or de-activate the audio alarm for any or all of the minor or major error conditions. The following description including the description relating to error conditions, operating modes, and touch panel screens are applicable to these discriminator systems and particularly to the above described discriminator systems having two output pockets such as shown in FIGS. 1–2, 10a–10b, 13, and 18. Furthermore, such systems transport and divert bills to one of the output pockets at speeds equal to or greater than 600 documents per minute. According to another embodiment, such systems transport and divert bills to one of the output pockets at speeds equal to or greater than 800 documents per minute. According to another embodiment, such systems transport and divert bills to one of the output pockets at speeds equal to or greater than 1000 documents per minute. These systems may also employ flash card memories as described in co-pending U.S. application Ser. No. 08/715,029, filed on Sep. 17, 1996, entitled "Software Loading System for a Currency Scanner" incorporated herein by reference in its entirety.

Minor Error Conditions

Minor errors are conditions which may or may not cause the machine to stop depending on the set-up, mode of operation, and error involved. Minors errors do not involve the review of more than one, if any, note. Minor errors do not disrupt running totals such as batch or sub-totals. According to one embodiment, the minor error conditions may be selectively activated or de-activated as desired by the user. For example, the machine may be programmed stop upon the occurrence of a "no call" document but not upon the occurrence of a "suspect document". The minor error conditions are listed as follows:

1) No Call (NC)
2) Suspect Document (SD)
3) Denomination Change (DC)
4) Stranger (S)
5) Separate Series (SS)
6) Improper Size (SZ)
7) Unfit Document (UD)
8) Reverse-Faced (RF)
9) Reverse-Oriented (RO)
10) Strap Limit (SL)
11) Stacker Full (SF)

No Call

A "no call" condition occurs when the discriminating device is unable to identify or determine the denomination of a note, the unidentified note being termed a no call.

Suspect Document

A "Suspect Document" is a note that fails one or more authentication tests based on a variety of monitored parameters. A discriminating device may permit the operator to enable or disable the detection of Suspect Documents, by for example, enabling or disabling one or more the authentication tests.

Denomination Change

A "Denomination Change" condition occurs when a note is identified having a denomination other than prior bills or a target denomination while the machine is operating in one of the sort modes described below. For example, when a $100 bill is scanned in a stack of previously scanned $50 bills, the condition "Denomination Change" may occur under certain circumstances while the machine is operating in a sort mode.

Stranger

The "Stranger" condition occurs when a note is identified having a denomination other than prior bills or a target denomination while the machine is operating in one of the stranger modes described below. The stranger mode is generally used when it is expected that most bills in a stack are of the same denomination. The stranger condition will be discussed in greater detail hereinafter in connection with several stranger modes of operation.

Separate Series (SS)

A "Separate Series" condition occurs when a note is identified as having a different series than prior bills or a target series. For example, when a new-series $100 bill (i.e., a 1996-series $100 bill) is scanned in a stack of previously scanned old-series $100 bills, the condition "Separate Series" may occur. This function may be employed in conjunction with the modes described below where it is desired to discriminate of notes based on their series, e.g., to discriminate between a 1993-series $50 bills and 1950-series $50 bills or to discriminate between all pre-1996 series U.S. notes from all 1996 and later series U.S. notes.

Improper Size

An "Improper Size" condition occurs when a document has a size that does not correspond to the size of one of the genuine documents that the system is programmed to recognize. For example, if the machine is set to process U.S. bills, then all documents should have the same size and any document that is not the same size as genuine U.S. currency will cause an "improper size" condition to occur. Likewise, for foreign bills, any document having a size other than one of the sizes of genuine foreign currency will cause an "improper size" condition to occur.

Unfit Document

An "Unfit Document" condition occurs when a document fails one or more fitness tests. Such fitness tests may detect, for example, the degree to which a bill is soiled, torn, or otherwise damaged. Likewise, the limpness of a document may also be employed as a fitness test.

Reverse-Faced

An "Reverse-Faced" condition occurs when a machine is operating in a facing mode and a document having a face orientation other than a target face orientation is detected.

Reverse-Oriented

An "Reverse-Oriented" condition occurs when a machine is operating in a Forward/Reverse Orientation mode and a document having a forward/reverse orientation other than a target forward/reverse orientation is detected.

Strap Limit

The discrimination device may permit the setting of limits on the number of bills based on various conditions. For example, it may be desirable to gather $20 bills into stacks of fifty bills. Accordingly, if for example bills are being processed such that $20 bills and only $20 are being directed into the first output receptacle, the device may halt after fifty $20 bills have been delivered into the first pocket. The display may then indicate that a strap limit has been reached for the first output pocket. Various strap limits may be factory-preset or user-set. Alternatively, "Strap Limits" may be determined by combining the number of notes delivered to two or more of the output pockets.

Stacker Full

The "Stacker Full" condition occurs when either or both of the pockets are at or near capacity and are not to receive additional notes. For example, in an embodiment in which the pockets are designed to receive a maximum of 300 currency notes, the discriminating device may be programmed to halt after 300 notes have been delivered to either of the pockets. The "stacker full" condition thereby will occur upon delivery of the 300th note. Similarly, in an embodiment in which the pockets are designed to receive 600 currency notes, the "stacker full" condition will occur upon delivery of the 600th note.

Major Error Conditions

Major errors are conditions which typically will stop the machine and may require the operator to remove and re-process more than one note. According to one embodiment, major error conditions include Jam (J), Double (D) and Chain (C). The condition "Jam" occurs when one or more sensors detect that a jam is occurring when notes are being transported between the input receptacle and the output receptacles. The condition "Double" occurs when two or more notes are fed by the transport mechanism in a stacked manner. The condition "Chain" occurs when two or more notes are fed by the transport mechanism in an overlapping manner.

Operating Modes

The discrimination system may be selectively programmed to operate in any of several operating modes. In general, these operating modes may be categorized as "stranger modes", "sort modes", "mixed modes" and "count modes". As will be described in greater detail hereinafter, the operating mode categories generally include two or three specific operating modes. An operator may select an individual operating mode or combination of operating modes as desired.

A. Stranger Modes

In general, stranger modes are used to process a stack of notes expected to be of the same denomination, in which the operator desires to remove "stranger" notes, or notes not having the same denomination. For example, a stranger mode may be selected to process a stack of notes substantially comprised of $10 bills so that all non-$10 bills may be removed from the stack. In a stranger mode, the machine will process the stack and place the "target" $10 notes into a selected pocket (e.g., pocket 1). Upon encountering a stranger note (or upon encountering another selected error condition), the machine may "present" the flagged note into the same pocket as the target note (i.e., stop the machine after the flagged bill is delivered into an output pocket, e.g., pocket 1) to allow the operator to inspect the note, or the machine may be programmed to off-sort the flagged note into the other pocket (e.g., pocket 2). Upon off-sorting the stranger note into pocket 2, the machine may be designed to either stop (present the note into pocket 2) and allow the operator to inspect the note, or continue processing the remaining notes in the stack.

A display, such as a touch panel display (e.g., FIG. 1), may indicate the number or aggregate value of notes having the target denomination, e.g., $10 bills. In one embodiment, the display is also capable of including totals associated with stranger notes via operator selection choices. For example, if a $5 stranger bill is detected in a stack of $10 bills, the operator may be prompted via the display as to whether the $5 bill should be incorporated into the running totals. If the operator responds positively, the $5 bill is incorporated into appropriate running totals, otherwise it is not. Alternatively, a set-up selection may be chosen whereby all stranger notes are automatically incorporated into appropriate running totals. The machine may include the following stranger modes as described below: stranger 1, stranger 2, stranger facing and stranger orientation.

1. Stranger 1 (STR 1)

In "Stranger 1" mode, the discriminator will process a stack of notes and place notes having a target denomination into pocket 1. The target denomination may be selected automatically by the discriminator to be that of the first note in the stack, or the target denomination may be explicitly selected by the operator. Upon the occurrence of a "stranger" condition (i.e., upon encountering a note not having the target denomination), the system may either present the flagged note into pocket 1 or off-sort the flagged note into pocket 2. Depending upon the set-up selected, the machine may either present the off-sorted flagged bill or continue processing bills. Optionally, the system may be similarly programmed to either present or off-sort flagged notes upon the occurrence of the "no call", "separate series", or "suspect document" conditions (minor errors). Upon encountering either the "strap limit", "stacker full", "chain", "double" or "jam" condition, the machine will stop, requiring the operator to undertake the appropriate corrective action before continuing such as removing bills from a full pocket or clearing a jam.

2. Stranger 2 (STR 2)

In "Stranger 2" mode, as in "Stranger 1" mode, the discriminator will process the stack and place notes having a target denomination into pocket 1. Upon encountering either the "strap limit" or "stacker full" condition, however, the machine will automatically begin delivering the target notes to pocket 2 provided that pocket is empty. Thereafter, upon encountering the "strap limit" or "stacker full" conditions again, the machine will automatically switch pockets and begin delivering bills into the other pocket if the other pocket has been cleared by the operator. If the other pocket has not been cleared, the machine will stop, requiring the operator remove the bills from either pocket 1 or pocket 2 before continuing. The display may indicate the aggregate value of the notes in the stack and/or the value or number of notes of each denomination in either pocket 1 or pocket 2.

Upon the occurrence of a minor error condition such as "stranger" (when the other pocket has not been cleared), no call, suspect document or separate series, the system may either present the flagged note into the current pocket or off-sort the flagged note into the other pocket and stop (i.e., present the flagged note in the other pocket). Alternatively, the system may be set to always present flagged notes into a given pocket (e.g., pocket 2) regardless of which pocket is the current pocket. Major errors will cause the machine to stop and the operator to take appropriate corrective action such as clearing a jam and/or reprocessing a stack of notes.

3. Stranger Facing (STR F)

In "Stranger Facing" mode, the machine is designed to process a stack of notes faced in substantially the same direction, e.g., placed in the input hopper face up, and to detect any notes facing the opposite direction. The ability to detect and correct for reverse-faced notes is important as the Federal Reserve requires currency it receives to be faced in the same direction. Thus, in "Stranger Facing" mode, the discriminator will process a stack of notes and place notes faced in a target direction and having a target denomination into pocket 1. The target direction and denomination may be selected automatically by the discriminator to be that of the first note in the stack, or the target direction and/or denomination may be explicitly selected by the operator. Upon the occurrence of a "stranger" condition (i.e., upon encountering a note having a denomination other than the target denomination) or upon the occurrence of a "reverse-faced" condition (i.e., upon encountering an opposite-faced note of the target denomination), the machine will either present the flagged note into pocket 1 or pocket 2 or off-sort the flagged note into pocket 2 and continue processing notes. Minor errors such as "suspect document", "no call", or "separate series" may be handled as discussed above, such as by presenting a flagged bill into either pocket 1 or pocket 2 or off-sorting into pocket 2 and continuing to process bills. For example, target notes may be delivered to pocket 1 and all other notes (strangers, no calls, suspect, separate series, reverse-faced) may be delivered to pocket 2. These bills may be simply off-sorted to pocket 2 and the machine may continue to process successive notes. Alternatively, one or more of the above conditions may be presented into pocket 2 (e.g., no calls and suspects may cause the machine to halt and appropriate messages to be displayed while strangers and reverse-faced notes are simply off-sorted but not presented).

According to another embodiment, notes having the target denomination and face orientation are delivered to one pocket (e.g., pocket 1) and notes having the target denomination but not the target face orientation are delivered to the other pocket (e.g., pocket 2). Only notes not having the target denomination are treated as stranger notes and may be handled by being presented into one of the pockets. Likewise, minor errors such as "suspect document", "no call", or "separate series" may be handled by presenting a flagged bill into either pocket 1 or pocket 2.

"Stacker full" or "strap limit" conditions may be handled by stopping and waiting for the operator to clear one or both pockets. The "strap limit" may be set up on a pocket by pocket basis or based on the combined contents of pockets 1 and 2. Major errors are handled as discussed above (see e.g., discussion of the stranger 2 mode).

4. Stranger Orientation (STR O)

In "Stranger Orientation" mode, the machine is designed to process a stack of notes faced in substantially the same forward/reverse orientation, e.g., in a predetermined forward or reverse orientation direction. The forward direction may be defined as the feed direction whereby the top edge of a note is fed first and conversely for the reverse direction. The ability to detect and correct for reverse-oriented notes is important as the United States Federal Reserve may soon require currency it receives to be oriented in the same forward/reverse direction. Thus, in "Stranger Orientation" mode, the discriminator will process a stack of notes and place notes having a target forward/reverse orientation and having a target denomination into pocket 1. The target orientation and denomination may be selected automatically by the discriminator to be that of the first note in the stack, or the target direction and/or denomination may be explicitly selected by the operator. Upon the occurrence of a "stranger" condition (i.e., upon encountering a note having a denomination other than the target denomination) or a "reverse-oriented" condition (i.e., upon encountering an opposite-oriented note of the target denomination), the machine will either present the flagged note into pocket 1 or pocket 2 or off-sort the flagged note into pocket 2 and continue processing notes. Minor errors such as "suspect document", "no call", or "separate series" may be handled as discussed above, such as by presenting a flagged bill into either pocket 1 or pocket 2 or off-sorting into pocket 2 and continuing to process bills. For example, target notes may be delivered to pocket 1 and all other notes (strangers, no calls, suspect, separate series, reverse-oriented) may be delivered to pocket 2. These bills may be simply off-sorted to pocket 2 and the machine may continue to process successive notes. Alternatively, one or more of the above conditions may be presented into pocket 2 (e.g., no calls and suspects may cause the machine to halt and appropriate messages to be displayed while strangers and reverse-oriented notes are simply off-sorted but not presented).

According to another embodiment, notes having the target denomination and orientation are delivered to one pocket (e.g., pocket 1) and notes having the target denomination but not the target orientation are delivered to the other pocket (e.g., pocket 2). Only notes not having the target denomination are treated as stranger notes and may be handled by being presented into one of the pockets. Likewise, minor errors such as "suspect document", "no call", or "separate series" may be handled by presenting a flagged bill into either pocket 1 or pocket 2.

"Stacker full" or "strap limit" conditions may be handled by stopping and waiting for the operator to clear one or both pockets. The "strap limit" may be set up on a pocket by pocket basis or based on the combined contents of pockets 1 and 2. Major errors are handled as discussed above (see e.g., discussion of the stranger 2 mode).

B. Sort Modes

Generally speaking, sort modes are designed to accommodate a pre-sorted stack of notes having a "rainbow" configuration, e.g., wherein the stack of notes includes two or more groups of notes, each group having a different denomination but each note within a given group having the same denomination. For example, the stack of notes may be pre-sorted to include a group of $1 bills at the beginning of the stack, followed by a group of $5 bills, followed by a group of $10 bills, etc. Sort modes permit a user to separate such a "rainbow" stack of notes into separate stacks according to denomination. Alternatively, sort modes may be used to sort a mixed stack of notes, e.g., not pre-sorted, into separate stacks according to denomination.

For example, in a sort mode, the machine may process a stack of notes and deposit a first group of "target" notes (e.g., $1 bills) into a selected pocket. Upon encountering a "denomination change" condition (or upon encountering another selected flagging condition), the machine may "present" the flagged note into the same pocket as the target note and stop to allow the operator to inspect the note, or the machine may be programmed to off-sort the flagged note into the other pocket. Upon off-sorting the denomination change note or other flagged note into pocket 2, the machine may be designed to either stop and allow the operator to inspect the note or to continue processing the remaining notes in the stack.

As described in relation to stranger modes above, the discrimination system may include a display to indicate the number or aggregate value of notes of each respective denomination and/or the number or aggregate value of notes in the stack. The machine may include the following sort modes as described below: sort 1, sort 2, sort 3, sort facing and sort orientation.

1. Sort 1 (SRT 1)

In "Sort 1" mode, the discriminator is designed to process a stack of notes and place notes having a first target denomination (e.g., target denomination 1) into pocket 1 and a second target denomination (e.g., target denomination 2) into pocket 2. The target denominations may be selected by the operator prior to sorting through a stack, or may be selected automatically by the discriminator, e.g., the first encountered denomination being designated target denomination 1 and the second encountered denomination being designated target denomination 2.

Where target denominations are set by the operator, bills of target denomination 1 are delivered into pocket 1 and bills of target denomination 2 are delivered to pocket 2. Bills having a denomination other than target denomination 1 or 2 are flagged. The flagged bills are presented into either pocket 1 or pocket 2.

For example, in one embodiment, the discriminator automatically designates the first target denomination (target note 1) to be that of the first note in the stack, then proceeds to deliver target note 1 to pocket 1. Upon encountering a "denomination change" condition, the discriminator flags the note, designates the flagged note as the second target denomination (target note 2) and delivers target notes 2 to pocket 2. Thereafter, upon encountering another "denomination change" condition, if the appropriate pocket has been cleared by the operator, the machine will proceed to deliver the third denomination of bills into pocket 1, the fourth denomination of bills into pocket 2, and so on. If the appropriate pocket has not been cleared, the machine will stop upon a "denomination change" condition, requiring the operator remove the bills from the appropriate pocket before continuing.

Upon encountering other minor errors such as "no call", "suspect document", and "separate series", the machine will stop, presenting the flagged bills into one of the pockets.

"Stacker full" or "strap limit" conditions may be handled by stopping and waiting for the operator to clear one or both pockets. Major errors are handled as discussed above (see e.g., discussion of the stranger 2 mode).

For example, in an embodiment in which the discriminator automatically selects the target denominations, if the first note in the stack is a $1 bill, the machine will designate target note 1 as a $1 bill and deliver $1 bills into pocket 1 until encountering the first non-$1 bill. The first non-$1 bill, which for example may be a $5 bill, is then designated as target note 2 and is delivered to pocket 2. Then, if and when the discriminator encounters a bill having a third denomination, which for example may be a $10 bill, the machine will either direct any subsequent $10 bills into pocket 1, or will stop if necessary to allow the operator to clear pocket 1. The machine may be designed to automatically resume operation delivering subsequent $10 bills into pocket 1 when the operator removes all the bills present in pocket 1. Assuming that pocket 1 is clear, the machine will then deliver $10 bills into pocket 1 until encountering the next series of bills, and so on until the entire stack has been processed.

2. Sort 2 (SRT 2)

In "Sort 2" mode, the discriminator will process a stack of notes and place notes having a target denomination into pocket 1. The target denomination may be selected automatically by the discriminator to be that of the first note in the stack, or the target denomination may be selected by the operator. Upon the occurrence of the "denomination change" condition (e.g., upon encountering a note not having the target denomination), the system will "present" the flagged note into pocket 1 and stop to allow the operator to inspect the note. Alternatively, the system may be programmed to present "denomination change" notes in pocket 2.

Upon encountering other minor errors such as "no call", "suspect document", and "separate series", the machine will stop, presenting the flagged bills into one of the pockets. Alternatively, one or more of these conditions may cause flagged bills to be off-sorted into pocket 2 without causing the system to stop. The system may permit the operator to select how these bills are to be handled via a set-up option.

"Stacker full" or "strap limit" conditions may be handled by stopping and waiting for the operator to clear one or both pockets. Major errors are handled as discussed above (see e.g., discussion of the stranger 2 mode).

For example, in an embodiment in which the discriminator automatically selects the target denominations, if the first note in the stack is a $1 bill, the machine will designate $1 as the target note and will deliver $1 bills into pocket 1 until encountering the first non-$1 bill. The first non-$1 bill, which may for example be a $5 bill, will then be "presented" into pocket 1. The operator may then remove all $1 bills from pocket 1 and then select an appropriate continuation key. If the first note in the remainder of the stack is also a $5 bill, the machine will designate $5 as the new target note and will proceed to deliver $5 bills into pocket 1 until encountering the first non-$5 bill, and so on until the entire stack has been processed. If the first note in the remainder of the stack is not a $5 bill, then a denomination change error will occur and the machine will present the non-$5 bill into pocket 1, and so on. According to another embodiment, after a denomination change note is presented into pocket 1, the machine restarts automatically when the operator removes all the bills in pocket 1. The operator may then separate the bills by denomination (e.g., place all $1 bills into one stack and the last $5 bill into its own stack).

3. Sort 3 (SRT 3)

In "Sort 3" mode, the discriminator will process a stack of notes and place notes having a target denomination into pocket 1, as in the Sort 2 mode. However, upon the occurrence of the "denomination change" condition, the system will off-sort the flagged note into pocket 2 rather than present the flagged note into pocket 1. The system may or may not be designed to stop after encountering non-target notes, i.e., "denomination change" notes.

According to one embodiment notes having a target denomination (target 1) are delivered to pocket 1. Upon encountering a first denomination change, the denomination of the first non-target 1 note is designated as a target 2 denomination (target 2). Target 2 notes and then off-sorted into pocket 2 without causing the machine to stop. The machine continues to process notes, delivering target 1 notes to pocket 1 and target 2 notes to pocket 2, until the first note having a denomination other than target 1 denomination or target 2 denomination is encountered. At this point this third denomination note is designated as the "new" target 2 denomination and is directed toward pocket 2. According to one embodiment this third denomination note is delivered to pocket 2 and the machine is stopped with the display indicating a denomination change in pocket 2. The operator can then take the appropriate action such as removing all notes in pocket 2 (e.g., in an automatic restart configured set up) or remove all bills other than the third denomination bill and press a continuation key. The machine will then continue processing notes, continuing to deliver original target 1 notes to pocket 1 and delivering "new" target 2 notes to pocket 2, until encountering a bill having a denomination other than target 1 or the present target 2. At this point, a denomination change occurs as described above and a new target 2 denomination is designated.

According to another embodiment, when a new target 2 note is encountered, the transport mechanism stops before the new target 2 note is delivered into the second output receptacle and a denomination change in pocket 2 message is displayed. In this manner, when the machine stops, all the bills in pocket 2 have the same denomination. The operator may then remove all the bills in pocket 2 and set them aside. Depending on the set up, the machine may either resume operation automatically or resume upon the selection of a continuation key. When the machine resumes, the new target note 2 is delivered into the now empty pocket 2 and the machine continues processing bills until encountering a "new" target note 2 denomination.

Upon encountering other minor errors such as "no call", "suspect document", and "separate series", the machine will stop, presenting the flagged bills into one of the pockets. "Stacker full" or "strap limit" conditions may be handled by stopping and waiting for the operator to clear one or both pockets. Major errors are handled as discussed above (see e.g., discussion of the stranger 2 mode).

For example, in an embodiment in which the discriminator automatically selects the target denominations, if the first note in the stack is a $1 bill, the machine will designate $1 as the target note and will deliver $1 bills into pocket 1 until encountering the first non-$1 bill. The first non-$1 bill, which may for example be a $5 bill, will then be off-sorted into pocket 2. According to one embodiment, the machine then continues to process notes, delivering $1 bills into pocket 1 and $5 bills into pocket 2, until encountering the next denomination change (i.e., a bill other than a $1 or a $5). Thereafter, upon encountering the next denomination change, such as a $10 bill, the $10 bills are designated as the new target 2 denomination and the system halts so that pocket 2 may be cleared. When the system resumes operation, the machine continues to process notes, delivering $1 bills into pocket 1 and $10 bills into pocket 2, until encountering the next denomination change (i.e., a bill other than a $1 or a $10), and so on.

4. Sort 4 (SRT 4)

In "Sort 4" mode, the discriminator will process a stack of notes and place notes having a target denomination into pocket 1. All other notes are delivered to pocket 2. Thus, upon the occurrence of the "denomination change" condition, the system will off-sort the flagged note into pocket 2. The system then continues processing any remaining bills without stopping. According to one embodiment, only notes having the target denomination (pocket 1) are counted while all non-target notes are simply delivered to pocket 2 without being counted.

Upon encountering other minor errors such as "no call", "suspect document", and "separate series", the machine may be programmed to stop, presenting the flagged bills into one of the pockets such as pocket 2. Alternatively, the machine may be programmed to effectively ignore one or more of the minor errors such as "no call", "suspect document", and "separate series" and to simply off-sort such bills to pocket 2 and continue processing any remaining bills. For example, the system may be set-up to simply off-sort into pocket 2 and continue processing bills upon encountering a "no call" or "separate series" note while stopping and presenting any "suspect documents" into pocket 2. Thus in this example, the machine will quickly process an entire stack of bills, separating bills of a target denomination from all other notes in the stack. Apart from major errors and "stacker full" or "strap limit" conditions, the machine would only stop if a suspect document is encountered.

"Stacker full" or "strap limit" conditions may be handled by stopping and waiting for the operator to clear one or both pockets. Major errors are handled as discussed above (see e.g., discussion of the stranger 2 mode).

5. Sort Facing (SRT F)

"Sort Facing" mode is substantially similar to "Stranger Facing" mode, the primary difference being the configuration of the stack of notes prior to processing. In "Sort Facing" mode, the stack of notes is generally pre-sorted into one or more groups of notes, each group being faced in a different direction, but each note within a given group facing the same direction and having the same denomination as other notes in that group, whereas in "Stranger Facing" mode, each note in the stack is expected to be faced in the same direction and have the same denomination. Thus, in "Sort Facing" mode, the discriminator will process the stack and place notes of a target denomination faced in a target direction into pocket 1. Upon encountering a target denomination but reverse-faced note (i.e., a reverse-faced condition), the machine will either present the flagged note into pocket 1 or off-sort the flagged note into pocket 2. When the reverse-faced target note is off-sorted to pocket 2, the machine may either present this note into pocket 2 or continue processing notes. The system may permit the operator to select how these bills are to be handled via a set-up option (e.g., present into pocket 1, present into pocket 2, or off-sort into pocket 2 and continue).

Upon encountering other minor errors such as "no call", "suspect document", and "separate series", the machine will stop, presenting the flagged bills into one of the pockets. "Stacker full" or "strap limit" conditions may be handled by stopping and waiting for the operator to clear one or both pockets. The "strap limit" may be set up on a pocket by pocket basis or based on the combined contents of pockets 1 and 2. Major errors are handled as discussed above (see e.g., discussion of the stranger 2 mode).

6. Sort Orientation (SRT O)

"Sort Orientation" mode is substantially similar to "Stranger Orientation" mode, the primary difference being the configuration of the stack of notes prior to processing. In "Sort Orientation" mode, the stack of notes is pre-sorted into one or more groups of notes, each group being oriented in a different direction, but each note within a given group having the same denomination and being oriented the same as other notes in that group. The discriminator will process the stack and place notes having the target denomination and being oriented in a target direction into pocket 1. Upon encountering a target denomination but reverse-oriented note (i.e., a reverse-oriented condition), the machine will either present the flagged note into pocket 1 or off-sort the flagged note into pocket 2. When the reverse-oriented target note is off-sorted to pocket 2, the machine may either present this note into pocket 2 or continue processing notes. The system may permit the operator to select how these bills are to be handled via a set-up option (e.g., present into pocket 1, present into pocket 2, or off-sort into pocket 2 and continue).

Upon encountering other minor errors such as "no call", "suspect document", and "separate series", the machine will stop, presenting the flagged bills into one of the pockets. "Stacker full" or "strap limit" conditions may be handled by stopping and waiting for the operator to clear one or both pockets. The "strap limit" may be set up on a pocket by pocket basis or based on the combined contents of pockets 1 and 2. Major errors are handled as discussed above (see e.g., discussion of the stranger 2 mode).

7. Sort Series (SRT S)

In "Sort Series" mode, the discriminator will process a stack of notes and place notes of a target series or group of series into pocket 1. Upon the occurrence of the "separate series" condition (e.g., upon encountering a note not having the target series), the system will off-sort the flagged note into pocket 2. The system may be programmed to stop or not to stop after encountering non-target notes, i.e., "separate series" notes. Alternatively, upon the occurrence of the "separate series" condition, the system may "present" the flagged note into pocket 1 and stop to allow the operator to inspect the note.

a. Update Pocket 2 Target—Denomination and Series

For example, in an embodiment in which the discriminator automatically selects the target series and denomination, if the first note in the stack is a 1996-series $100 bill, the machine will designate 1996-series $100 bills as the target note and will deliver 1996-series $100 bills into pocket 1 until encountering the first non-1996-series $100 bill. The first non-1996-series $100 bill, which may, for example, be a 1995-series $5 bill, will then be off-sorted into pocket 2. According to one embodiment, the machine then continues to process notes, delivering 1996-series $100 bills into pocket 1 and 1995-series $5 bills into pocket 2, until encountering the next separate series condition (i.e., a bill other than a 1996-series $100 or a 1995-series $5). Thereafter, upon encountering the next separate series condition, such as a 1995-series $10 bill, the 1995-series $10 bills are designated as the new target 2 series and the system halts so that pocket 2 may be cleared. When the system resumes operation, the machine continues to process notes, delivering 1996-series $100 bills into pocket 1 and 1995-series $10 bills into pocket 2, until encountering the next separate series condition (i.e., a bill other than a 1996-series $100 or a 1995-series $10), and so on.

b. Update Target 1—Denomination and Series

According to another embodiment in which target notes are defined in terms of series and denomination and in which the discriminator automatically selects the target series and denomination, if the first note in the stack is a 1996-series $100 bill, the machine will designate 1996-series $100 as the target series and denomination and will deliver 1996-series $100 bills into pocket 1 until encountering the first non-1996-series $100 bill. The first non-1996-series $100 bill, which may for example be a 1995-series $5 bill, will then be "presented" into pocket 1. The operator may then remove all 1996-series $100 bills from pocket 1 and then select an appropriate continuation key. The machine will then designate 1995-series $5 as the new target note and will proceed to deliver 1995-series $5 bills into pocket 1 until encountering the first non-1995-series $5 bill, and so on until the entire stack has been processed. If a note in the remainder of the stack is not a 1995-series $5 bill, then a separate series error will occur and the machine will present the non-1995-series $5 bill into pocket 1, and so on. According to another embodiment, after a separate series note is presented into pocket 1, the machine restarts automatically when the operator removes all the bills from pocket 1. The operator may then separate the bills by denomination and series (e.g., place all 1996-series $100 bills into one stack and the last 1995-series $5 bill into its own stack). Minor errors such as "no calls" and "suspect documents" may be presented in pocket 2 or off-sorted into pocket 2 with the machine continuing to process bills.

c. Update Pocket 2 Target—Series

According to another embodiment, target notes are defined only by series or group of series regardless of denomination. According to one embodiment, notes having a target series (target 1) are delivered to pocket 1. Upon encountering a first separate series condition, the series of the first non-target 1 note is designated as a target 2 series (target 2). Target 2 notes are then off-sorted into pocket 2 without causing the machine to stop. The machine continues to process notes, delivering target 1 notes to pocket 1 and target 2 notes to pocket 2, until the first note having a series other than target 1 series or target 2 series is encountered. At this point this third series note is designated as the "new" target 2 series and is directed toward pocket 2. According to one embodiment this third series note is delivered to pocket 2 and the machine is stopped with the display indicating a series change in pocket 2. The operator can then take the appropriate action such as removing all notes in pocket 2 (e.g., in an automatic restart configured set up) or remove all bills other than the third series bill and press a continuation key. The machine will then continue processing notes, continuing to deliver original target 1 notes to pocket 1 and delivering "new" target 2 notes to pocket 2, until encountering a bill having a series other than target 1 or the current target 2. At this point, a separate series condition occurs as described above and a new target 2 series is designated.

According to another embodiment, when a new target 2 note is encountered, the transport mechanism stops before the new target 2 note is delivered into the second output receptacle and a series change in pocket 2 message is displayed. In this manner, when the machine stops, all the bills in pocket 2 have the same series. The operator may then remove all the bills in pocket 2 and set them aside. Depending on the set up, the machine may either resume operation automatically or resume upon the selection of a continuation key. When the machine resumes, the new target note 2 is delivered into the now empty pocket 2 and the machine continues processing bills until encountering a "new" target note 2 series.

Upon encountering other minor errors such as "no call" and "suspect document", the machine will stop, presenting the flagged bills into one of the pockets. "Stacker full" or "strap limit" conditions may be handled by stopping and waiting for the operator to clear one or both pockets. Major errors are handled as discussed above (see e.g., discussion of the stranger 2 mode).

For example, in an embodiment in which the discriminator automatically selects the target series, if the first note in the stack is a 1996-series $100 bill, the machine will designate 1996-series bills as the target series and will deliver all 1996-series bills into pocket 1 until encountering the first non-1996-series bill. The first non-1996-series bill, which may for example be a 1995-series $5 bill, will then be off-sorted into pocket 2. According to one embodiment, the machine then continues to process notes, delivering 1996-series bills into pocket 1 and 1995-series bills into pocket 2, until encountering the next separate series condition (i.e., a bill other than a 1996-series or a 1995-series note). Thereafter, upon encountering the next separate series condition, such as a 1993-series $20 bill, 1993-series bills are designated as the new target 2 series and the system halts so that pocket 2 may be cleared. The machine then continues to operate in a similar manner as described in the paragraph entitled "Update Pocket 2 Target—Denomination and Series."

d. Update Target 1—Series

According to another embodiment in which target notes are defined only by series or group of series regardless of denomination and in which the discriminator automatically selects the target series and denomination, if the first note in the stack is a 1996-series $100 bill, the machine will designate 1996-series as the target series and will deliver all 1996-series bills into pocket 1 until encountering the first non-1996-series bill. The first non-1996-series bill, which may for example be a 1995-series $5 bill, will then be "presented" into pocket 1. The machine then continues to operate in a similar manner as described in the above paragraph entitled "Update Target 1—Denomination and Series" designating 1995-series notes as the new target series. Minor errors such as "no calls" and "suspect documents" may be presented in pocket 2 or off-sorted into pocket 2 with the machine continuing to process bills.

According to another embodiment, target series are defined by series or group of series without regard to denomination. Moreover, factory default or user defined series categories may be defined. For example, a "new series" group may be defined to include all bills having a series of 1996 or later. This group may include for example, 1996-series $100s and 1997-series $50s and $20s). An "old-series" group may be defined as all other bills. Alternatively, a "series 1" group may be defined to include, for example, all 1996-series and later $100s, all 1997-series and later $50s and $20s, and all $1s, $2, $5, and $10 regardless of series). Likewise, an accompanying "series 2" group may be defined to include all pre-1996-series $100s and all pre-1997-series $50s and $20s. Using series 1 or series 2 in one of the above described series mode embodiments will permit the separation of all "old" series $100s, $50s, and $20s from all other bills. Such an embodiment facilitates in the culling of all bills that are to be removed from circulation. As additional "new" series bill enter circulation (e.g., a 1999-series $10 bill), the definitions of series 1 and series 2 may then be modified so that all bills that are to be removed from circulation may be easily culled from all other bills.

For example, a series group (Series A) may be defined as all bills having a series of 1995 or later. According to one embodiment, Series A is designated as the target series and all Series A notes are delivered to pocket 1 and all non-Series A bills are off-sorted to pocket 2. The machine may or may not be programmed to halt when a non-Series A note is encountered. Where the machine is not programmed to halt, a stack of bills may be quickly processed and separated into a group consisting of all 1995 and later series notes (pocket 1) and all pre-1995 series notes (pocket 2).

C. Mixed Modes

Generally speaking, mixed modes are designed to accommodate a stack of notes having a "mixed" configuration, e.g., including two or more denominations of notes in no particular order, where the operator desires to determine the number or aggregate value of notes of each respective denomination and/or the number or aggregate value of notes in the stack. Mixed modes "Mix 1", "Mix 2", "Mixed Facing" and "Mixed Orientation", each of which will be described below. As with stranger and sort modes, the discrimination system may include a display to indicate the number or aggregate value of notes of each respective denomination and/or the number or aggregate value of notes in the stack.

1. Mixed 1 (Mix 1)

In "Mix 1" mode, the discriminator will process the stack of mixed notes and will generally place the notes into pocket 1. However, upon the occurrence of the "no call" or "suspect document" condition, the discriminator will flag the note and either present the flagged note into pocket 1 or off-sort the flagged note into pocket 2. The system may permit the operator to select how these bills are to be handled via a set-up option (e.g., present into pocket 1, present into pocket 2, or off-sort into pocket 2 and continue).

A "Stacker full" condition may be handled by stopping and waiting for the operator to clear the full pocket. Major errors are handled as discussed above (see e.g., discussion of the stranger 2 mode).

2. Mixed 2 (Mix 2)

In "Mix 2" mode, as in "Mix 1" mode, the discriminator will process the stack and begin placing notes into pocket 1 until encountering a "no call" or "suspect document" condition, in which case the discriminator will flag the note and present the flagged note into either pocket 1 or pocket 2. The system may permit the operator to select how these bills are to be handled via a set-up option (e.g., present into pocket 1 or present into pocket 2).

Upon encountering the "stacker full" condition, however, the machine will not stop, as in "Mix 1" mode, but instead will automatically begin delivering the notes to pocket 2. Thereafter, upon encountering the "stacker full" condition in pocket 2, the machine will again switch pockets and begin delivering bills into pocket 1 if pocket 1 has been cleared by the operator. If pocket 1 has not been cleared and the "stacker full" condition thereby exists in both pockets 1 and 2, the machine will stop, requiring the operator to remove the bills from either pocket 1 or pocket 2 before continuing.

Major errors are handled as discussed above (see e.g., discussion of the stranger 2 mode).

3. Mixed Facing (Mix F)

In "Mixed Facing" mode, the discriminator will process a stack of mixed notes and place notes faced in a target direction into pocket 1. Upon encountering a reverse-faced note, the machine will either present the reversed-faced note into pocket 1 or off-sort the reverse-faced note into pocket 2. The system may permit the operator to select how these bills are to be handled via a set-up option (e.g., present into pocket 1, present into pocket 2, off-sort into pocket 2 and continue).

Upon encountering a "no call" or "suspect document" condition, the discriminator will flag the note and either present the flagged note into pocket 1 or off-sort the flagged note into pocket 2. The system may permit the operator to select how these bills are to be handled via a set-up option (e.g., present into pocket 1, present into pocket 2, off-sort into pocket 2 and continue). Where reverse-faced notes are being off-sorted into pocket 2 without causing the machine to halt, no calls and suspect documents should be presented into either pocket 1 or pocket 2.

The machine will stop, requiring the operator to remove the bills from the appropriate pocket before continuing, upon encountering a "stacker full" condition. Major errors are handled as discussed above (see, e.g., discussion of the stranger 2 mode).

4. Mixed Orientation (Mix O)

In "Mixed Orientation" mode, the discriminator will process a stack of mixed notes and place notes oriented in a target direction into pocket 1. Upon encountering a reverse-oriented note, the machine will either present the flagged note into pocket 1 or off-sort the flagged note into pocket 2. The system may permit the operator to select how these bills are to be handled via a set-up option (e.g., present into pocket 1, present into pocket 2, off-sort into pocket 2 and continue).

Upon encountering a "no call" or "suspect document" condition, the discriminator will flag the note and either present the flagged note into pocket 1 or off-sort the flagged note into pocket 2. The system may permit the operator to select how these bills are to be handled via a set-up option (e.g., present into pocket 1, present into pocket 2, off-sort into pocket 2 and continue). Where reverse-oriented notes are being off-sorted into pocket 2 without causing the machine to halt, no calls and suspect documents should be presented into either pocket 1 or pocket 2.

The machine will stop, requiring the operator to remove the bills from the appropriate pocket before continuing, upon encountering the "stacker full" condition. Major errors are handled as discussed above (see e.g., discussion of the stranger 2 mode).

D. Count Mode (CNT)

"Count Mode" is designed to accommodate a stack of notes in any configuration, where the operator desires to determine the number or total value of notes in a stack. The discriminator will process the stack, placing notes into pocket 1 until encountering a "stacker full" or "strap limit" condition, in which case the discriminator will automatically begin to place the notes into pocket 2. Thereafter, upon encountering the "stacker full" or "strap limit" condition in pocket 2, the machine will again switch pockets and begin delivering bills into pocket 1 if pocket 1 has been cleared by the operator. If pocket 1 has not been cleared and the "stacker full" or "strap limit" condition thereby exists in both pockets 1 and 2, the machine will stop, requiring the operator to remove the bills from either pocket 1 or pocket 2 before continuing. Count mode may operate in either a unit mode or a value mode. In the unit mode, notes are simply counted and the total number of notes is communicated. In the value mode, the values of notes are totaled and the total value is communicated. Likewise, strap limits may be defined in terms of a unit or piece count (e.g., 100 notes) or in terms of a total value (e.g., $200 notes in notes).

The machine will also stop, requiring the operator to remove the bills from the appropriate pocket, upon encountering a "suspect document" condition. Major errors are handled as discussed above (see, e.g., discussion of the stranger 2 mode).

FIGS. 41 and 42 summarize some embodiments of the above described modes. For example, in Stranger 1 mode (STR 1), bills having a target denomination are delivered into pocket 1. Chains (C), Jams (J), and Doubles (D) cause the machine to halt with chain, jammed, and doubled bills being directed to pocket 1. Also, strap limits (SL) and stacker full (SF) errors in pocket 1 cause the machine to halt. Strangers (S), No Calls (NC), Separate Series (SS), and Suspect (SD) bills may be optionally directed to either pocket 1 or pocket 2 depending on user selections.

Figure 19:
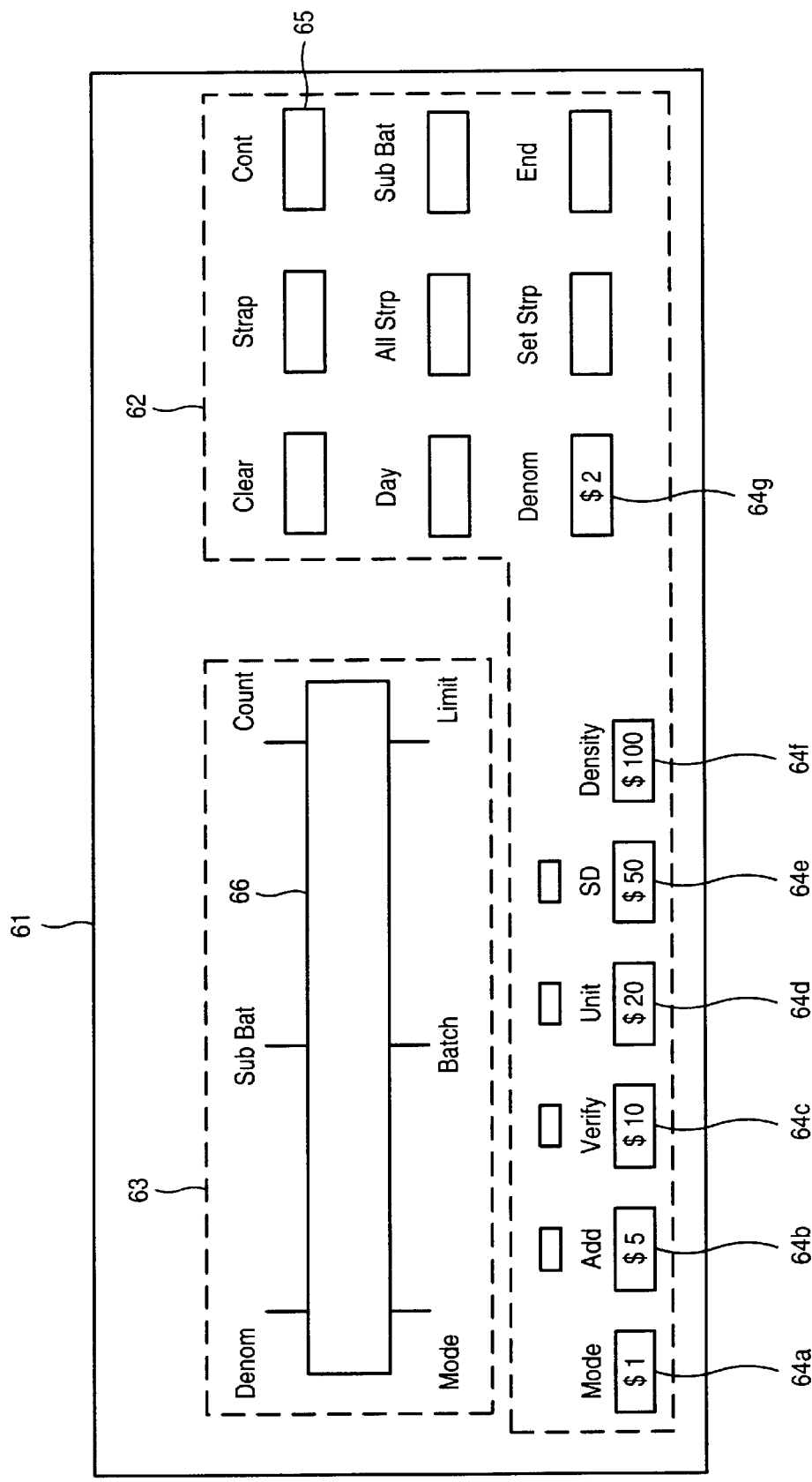
FIG. 19 is a front view of a control panel according to one embodiment of the present invention.

Each of the above operating modes is designed to be selectively activated, either individually or in combination, by an operator. In one embodiment of the present invention, the operating modes may be activated through a control panel. FIG. 19 is a front view of a control panel 61 according to one embodiment of the present invention. The control panel 61 comprises a keypad 62 and a display section 63. The keypad 62 comprises a plurality of keys including seven denomination selection elements 64a–64g, each associated with one of seven U.S. currency denominations, i.e., $1, $2, $5, $10, $20, $50, and $100. For foreign bill discriminators, the denomination selection elements may be labeled according to the currency system which a discriminator is designed to handle, and accordingly, there may be more or less than seven denomination selection elements. The $1 denomination selection key 64a also serves as a mode selection key. The keypad 62 also comprises a "Continuation" selection element 65. Various information such as instructions, mode selection information, authentication and discrimination information, individual denomination counter values, and total batch counter value are communicated to the operator via an LCD 66 in the display section 63.

Figure 20:
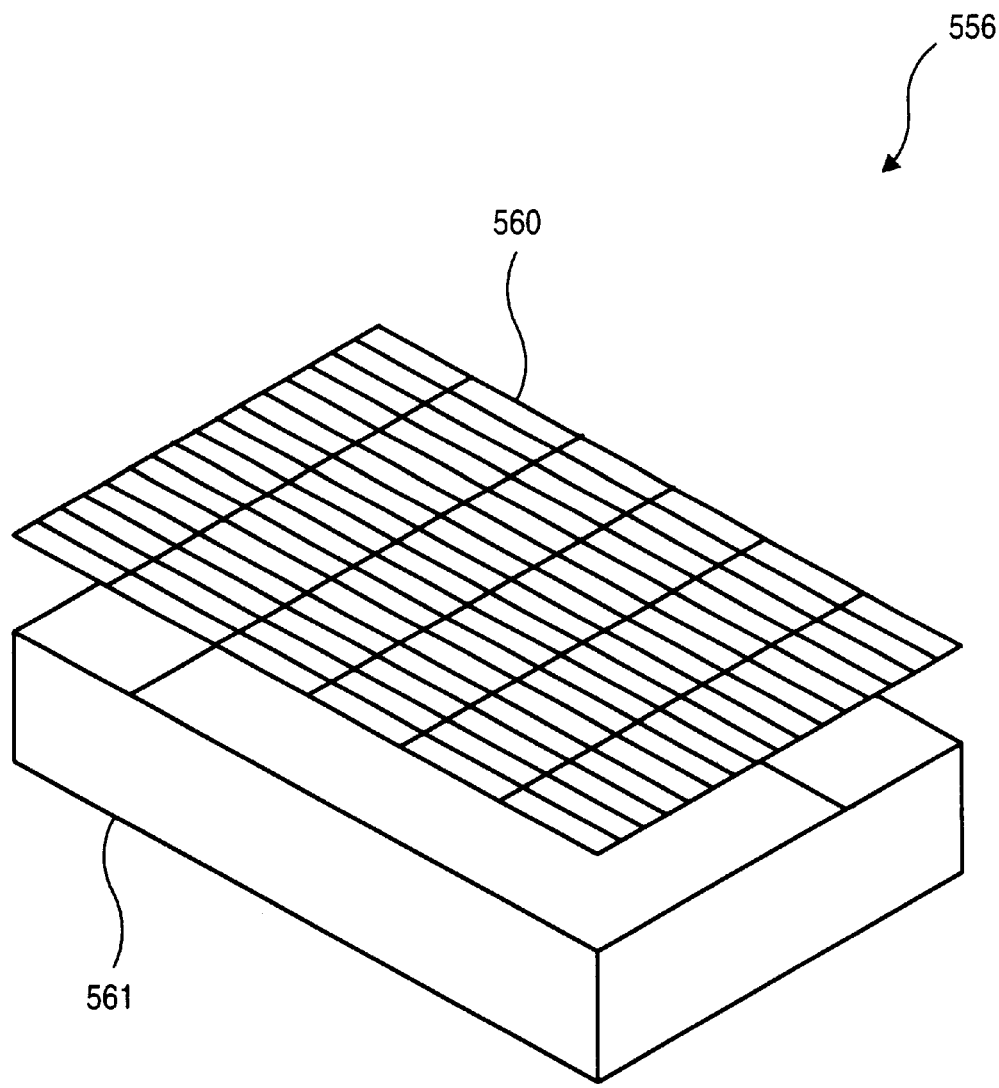
FIG. 20 is a touch screen according to one embodiment of the present invention.

According to another embodiment, a touch screen is employed to display selection elements for selection by the operator as well as to display various messages to the operator including status and error conditions. Additionally, the touch screen input/output device may be employed to provide on-line help information to the operator, for example, to explain an operation feature or how to handle a given error condition. An example of a touch screen is illustrated in FIG. 20. The touch screen I/O device 556 includes a touch screen 560 mounted over a graphics display 561. In one embodiment, the display 561 is a liquid crystal display (LCD) with backlighting. The display may have, for example, 128 vertical pixels and 256 horizontal pixels. The display 561 contains a built-in character generator which permits the display 561 to display text and numbers having font and size pre-defined by the manufacturer of the display. Moreover, a controller such as a CPU is programmed to permit the loading and display of custom fonts and shapes (e.g., key outlines) on the display 561. The display 561 is commercially available as Part No. GMF24012EBTW from Stanley Electric Company, Ltd., Equipment Export Section, of Tokyo, Japan.

The touch screen 560 may be an X-Y matrix touch screen forming a matrix of touch responsive points. The touch screen 560 includes two closely spaced but normally separated layers of optical grade polyester film each having a set of parallel transparent conductors. The sets of conductors in the two spaced polyester sheets are oriented at right angles to each other so when superimposed they form a grid. Along the outside edge of each polyester layer is a bus which interconnects the conductors supported on that layer. In this manner, electrical signals from the conductors are transmitted to the controller. When pressure from a finger or stylus is applied to the upper polyester layer, the set of conductors mounted to the upper layer is deflected downward into contact with the set of conductors mounted to the lower polyester layer. The contact between these sets of conductors acts as a mechanical closure of a switch element to complete an electrical circuit which is detected by the controller through the respective buses at the edges of the two polyester layers, thereby providing a means for detecting the X and Y coordinates of the switch closure. A matrix touch screen 560 of the above type is commercially available from Dynapro Thin Film Products, Inc. of Milwaukee, Wis.

As illustrated in FIG. 20, the touch screen 560 forms a matrix of ninety-six optically transparent switch elements having six columns and sixteen rows. The controller is programmed to divide the switch elements in each column into groups of three to form five switches in each column. Actuation of any one of the three switch elements forming a switch actuates the switch. The uppermost switch element in each column remains on its own and is unused.

Although the touch screen 560 uses an X-Y matrix of optically transparent switches to detect the location of a touch, alternative types of touch screens may be substituted for the touch screen 560. These alternative touch screens use such well-known techniques as crossed beams of infrared light, acoustic surface waves, capacitance sensing, and resistive membranes to detect the location of a touch. The structure and operation of the alternative touch screens are described and illustrated, for example, in U.S. Pat. Nos. 5,317,140, 5,297,030, 5,231,381, 5,198,976, 5,184,115, 5,105,186, 4,931,782, 4,928,094, 4,851,616, 4,811,004, 4,806,709, and 4,782,328, which are incorporated herein by reference in their entirety.

As described briefly above, one of the functions of the touch screen display is to display selection elements which may be selected by touching the portion of the screen associated with the selection element. The touch screen thereby serves in one respect as a "keyboard", wherein the selection elements displayed on the screen represent "keys" that are activated by touching the associated area of the screen. Alternatively, it will be appreciated that a conventional keyboard may be used instead of or in addition to the touch screen keyboard to facilitate selection of various selection elements. At any rate, in embodiments using a touch screen, the touch screen display may display not only selection elements or "keys", but also may display messages to the operator including status and error conditions of the discrimination system. Preferably, the configuration of the touch screen display is programmably changeable between several configurations, so that at any given time the touch screen will display only those "keys" or status and error conditions that are appropriate with respect to the present status of the discrimination system. For example, the touch screen may display a series of "menus" or "sub-menus", each menu being associated with a particular mode of operation or status of the discrimination system and thereby including only those keys or display conditions appropriate to the particular mode or status of the discrimination system. The menu-driven approach is designed to simplify the "keyboard" for operators and reduce training times accordingly. The touch screen display may be programmed via computer software including set-up software, operation software and diagnostic software.

Set-Up Information

The set-up software is designed to enable the operator to customize various operating parameters and engage or disengage various features of the discrimination system. The operating parameters may include, for example, default settings, stopping conditions, off-sort modes, pocket settings, denomination keys, stranger records or communications port settings. For example, a set-up mode may permit the user to identify which pocket is to receive no calls, suspect documents, mis-faced and mis-oriented documents, strangers, denomination changes, doubles, and chains or other bills or documents causing other types of minor or major errors. This information may be retrieved from the user via a routing interface having a data retrieval device such as a touch-screen. Alternatively, the data retrieval device may be some other kind of input or input/output device such as a keypad, buttons, or switches. Likewise, the set-up mode may permit the user to define which pockets are to receive which kinds of documents and whether the system should stop upon the occurrence of various events, e.g., various minor errors. Information concerning whether the system should stop upon the occurrence of one or more of the above conditions may be retrieved from the user via a flagging control interface having a flagging data retrieval device such as a touch-screen. Alternatively, the flagging data retrieval device may be some other kind of input or input/output device such as a keypad, buttons, or switches. The flagging control interface may be combined with the routing interface. Likewise the same touch-screen or input device may be used both to retrieve data concerning to which pockets various bills are to be directed as well as whether the system should stop upon the occurrence of one or more events such as the occurrence of one or more types of minor errors. The features of the discrimination system which may be engaged or disengaged in the set-up mode include operating modes, operating keys, sub-batching, suspect document authentication tests, stranger records, separate series discrimination, and/or audio alarms.

As described generally above, in a touch screen embodiment, the above-described operating features may be activated by touching selection elements or "keys" in respective "menus" associated with the operating features. Thus, in the set-up mode, the discrimination system may include the following:

(1) a key or keys which allows the customization of user-default settings or the selection of a factory default setting;

(2) a key which engages or disengages sub-batching;

(3) a key or keys which engage or disengage the operating modes, e.g., STR 1, STR 2, STR F, STR O, SRT 1, SRT 2, SRT 3, SRT F, SRT O, Mix 1, Mix 2, MIX F, MIX O and Count;

(4) a key or key which engages or disengages the operating keys "Verify" (permits the machine to process bills without affecting existing totals), "Unit" (toggles between unit and value modes), "SD", "Density", "Add" (toggles between maintaining running totals and clearing running totals when the input hopper and both output pockets are cleared) or "Mode";

(5) a key or keys which engages or disengages the audio alarms for the various error conditions, e.g., Jam (J), Doubles (D), Chain (C), Stranger (S), Denomination Change (DC), No Call (NC), Suspect Document (SD), Separate Series (SS), Strap Limit (SL), or Stacker Full (SF);

(6) a key or keys which sets the use of denomination keys for the minor errors of no call (NC) and suspect document (SD);

(7) a key or keys which sets a stranger record (i.e., sets whether the system should "record" or reflect in the appropriate counters the denomination/value of stranger notes);

(8) a key for enabling or disabling the SD minor error condition;

(9) a key for enabling or disabling the SS minor error condition;

(10) a key or keys for setting the configuration of communication ports;

(11) a key or keys for setting pockets for target notes, either manually or automatically;

(12) a key or keys for enabling or disabling the "off-sort" function or customizing stopping conditions related to the off-sort function (e.g., present into pocket 1, present into pocket 2, off-sort and continue); and

(13) a key or keys for engaging or disengaging the "Face" and "Right" keys (the "Right" key is a forward/reverse orientation key).

When engaged in the set-up mode, pressing the "Face" key gives the user the ability to quick-face a stack of bills. The machine will deliver face-up bills to pocket 1 and face-down bills to pocket 2. Similarly, pressing the "Right" key gives the user the ability to quick-right a stack of bills. The machine will deliver "readable" bills, e.g., wherein the words of the bill are right-side-up, to pocket 1 and non-readable bills, e.g., . wherein the words of the bill are upside-down, to pocket 2. Accordingly, the "Right" key causes bills having a forward orientation to be delivered to one pocket while causing bills having a reverse orientation to be delivered to the other pocket.

Operation Screens

Figure 21:
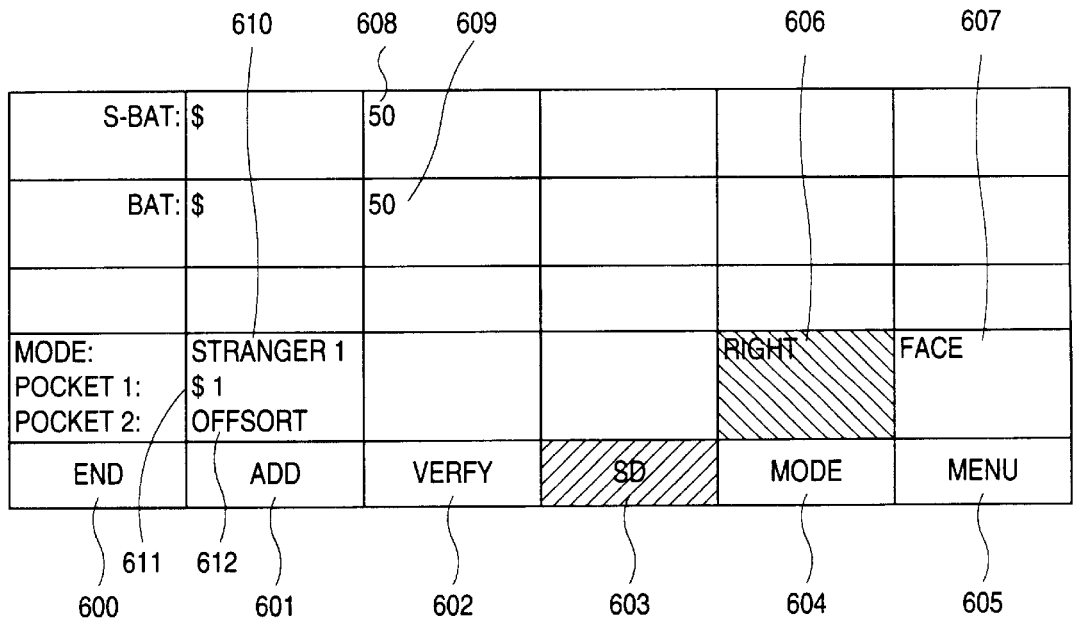

The operating software is designed to provide the operator with a series of menus or screens, each screen generally being associated with one or more modes of operation, e.g., STR 1, STR 2, etc. As described above, in a touch screen embodiment, each of the screens include selection elements or "keys" which the operator may touch to activate appropriate functions related to the operating mode or status of the discriminator. The screens are further designed to display messages to the operator related to the operating modes such as, for example, batch or sub-batch totals and status or error conditions. Preferably, the touch screen at any given time will display only those "keys" or status and error conditions that are associated with the present status of the discrimination machine. FIG. 21 represents a "crossroad" or "main" touch screen associated with the a machine operating in "Stranger 1" (STR 1) mode. The hatched keys represent functions that are engaged. The touch screen contains the following keys and displays:

END (600)

This key ends either a sub-batch (by pressing once) or a batch (by pressing twice).

ADD (601)
  This key engages or disengages the Add function.
VERFY (602)
  This key allows for Verify mode operation.
SD (603)
  This key engages or disengages the Suspect Document (SD) minor error condition.
MODE (604)
  This key engages the operating modes.
MENU (605)
  This key enables the operator to view totals, set strap limits, and SD and Density thresholds.
RIGHT (606)
  This key enables the operator to quick-right a stack of bills when this function is enabled in the set-up mode.
FACE (607)
  This key enables the operator to quick-face a stack of bills when in this function is enabled in the set-up mode.
S-BAT display (608)
  This displays aggregate totals associated with a sub-batch of currency bills.
BAT display (609)
  This displays aggregate totals associated with a batch of currency bills.
MODE display (610)
  This displays the selected mode of operation of the machine.
POCKET 1 display (611)
  This displays the target note associated with pocket 1.
POCKET 2 display (612)
  This displays the notes associated with pocket 2.

Figure 22:
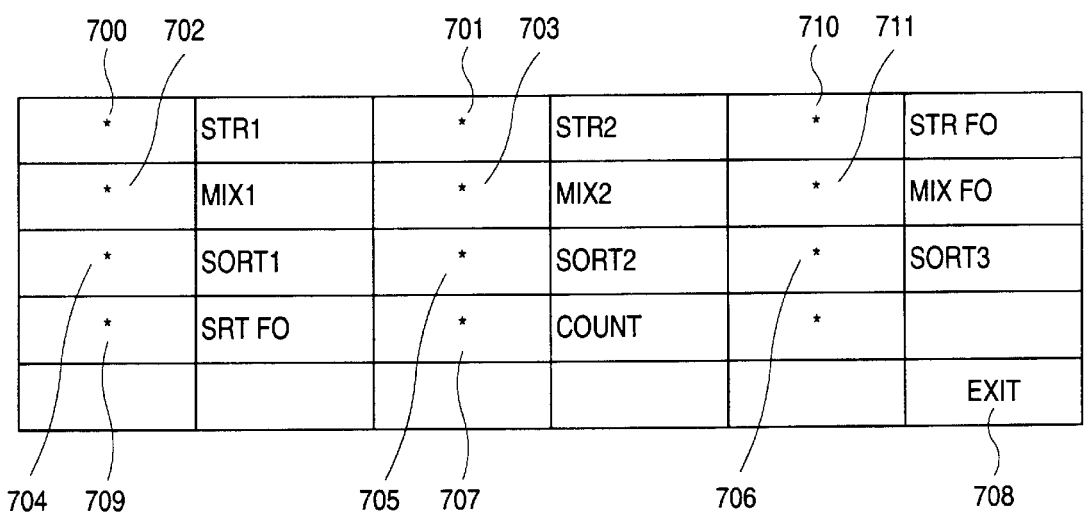
Figure 23:
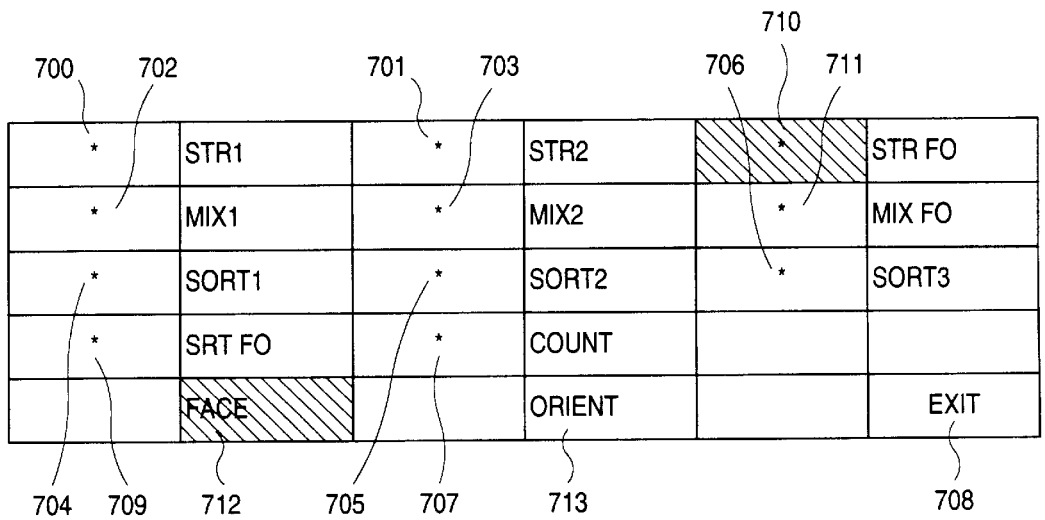

From the screen shown in FIG. 21, in STR 1 mode, pressing the MODE key will produce the screen shown in FIG. 22, comprising a series of keys associated with the operating modes. Upon touching one of keys STR 1 (700), STR 2 (701), MIX 1 (702), MIX 2 (703), SORT 1 (704), SORT 2 (705), SORT 3 (706) or COUNT (707), the machine will transition directly to a display associated with the appropriate operating mode. For example, if an operator wishes to return to the STR 1 menu shown in FIG. 21, he or she simply executes a single "key stroke", touching either the EXIT key (708) or the STR 1 key (700). However, if an operator wishes to select one of the facing or orientation modes, SRT F, SRT O, STR F, STR O, MIX F or MIX O, he or she must execute two "key strokes", the first of which is to select one of keys SRT OF (709), STR OF (710) or MIX OF (711). Upon selecting one of these keys, the display shown in FIG. 23 will appear, prompting the operator to choose FACE (712) or ORIENT (713) in the associated mode. For example, in the display of FIG. 23, the operator has selected STR F mode, first by touching the STR OF key (710), then by touching the FACE key (712).

Figure 24:
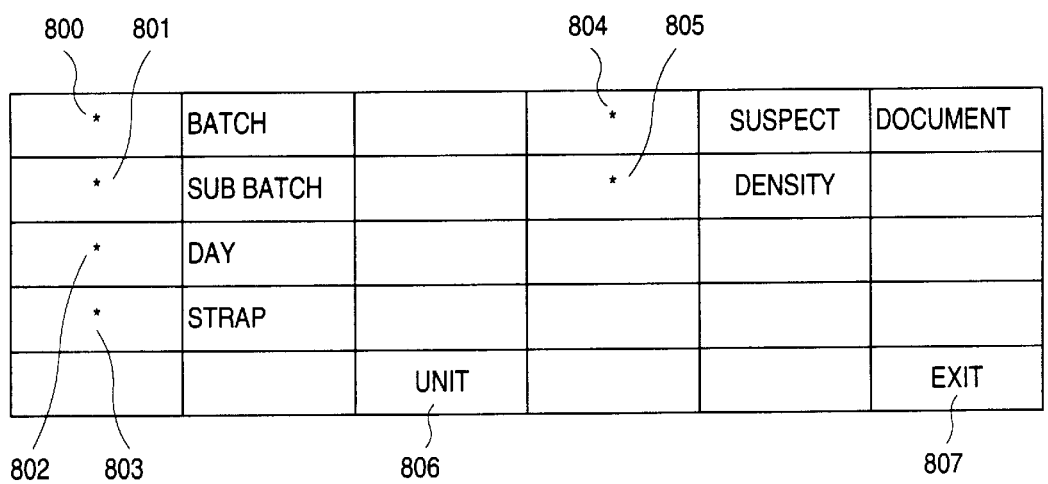

From the screen shown in FIG. 21, in STR 1 mode, pressing the MENU key (605) will produce the screen shown in FIG. 24, including BATCH (800), SUB BATCH (801), DAY (802), STRAP (803), SUSPECT DOCUMENT (804), DENSITY (805), UNIT (806) and EXIT (807) keys. Pressing the EXIT key (807) will bring the operator back to the main menu of FIG. 21. From this screen, pressing BATCH (800), SUB BATCH (801) or DAY (802) will produce a screen indicating totals for the appropriate key. For example, if an operator desires to obtain batch totals, he or she touches the BATCH key (800), which will produce the screen shown in FIG. 25. The screen shown in FIG. 25 indicates the number and aggregate value of each denomination of currency in the batch. Pressing the CLEAR key (810) in the screen of FIG. 25 will clear the appropriate totals and EXIT (811) will bring the operator back to the menu screen of FIG. 24.

From the menu screen (FIG. 24), pressing the STRAP key (803) will produce a screen (FIG. 26) within which strap limits may be set for various denominations of currency. Nine denominations can be accommodated for international markets. A highlighted cursor (900), indicated by hatching in FIG. 26, may be moved by the UP (901) and DOWN (902) keys at the right of the display to a particular denomination selected by the operator, e.g., $5 in the example shown. Thereafter, strap limits may be set by touching one or more of the direct access keys (903a–g) at the bottom of the screen. For example, a strap limit of 100 may be selected by touching the "100" key (903g). The "+" (904) and "–" (905) keys allow the operator to program the unit or limit at a custom amount, by incrementing or decrementing the displayed value. For example, the unit limit 38 may have been selected by first touching the "50" key (903e) and then touching the "–" key (905) twelve times. The CLEAR key (906) is designed to clear the limit and unit count associated with the highlighted line. Similarly, all the strap limits may be cleared by pressing ALL (907), then CLEAR (906). Pressing the UNIT key (909) toggles the display between presenting the information in unit form as shown in FIG. 26 and value form (e.g., dollars). For example, if the UNIT key (909) were pressed in FIG. 26, then the word "UNIT" between "DENOM" and "LIMIT" would change to "VALUE" and the "38" for the $5 line would change to "$190" and the "100" for the $5 line would change to "$500". EXIT (908) will bring the operator back to the menu screen of FIG. 24.

Figure 27:
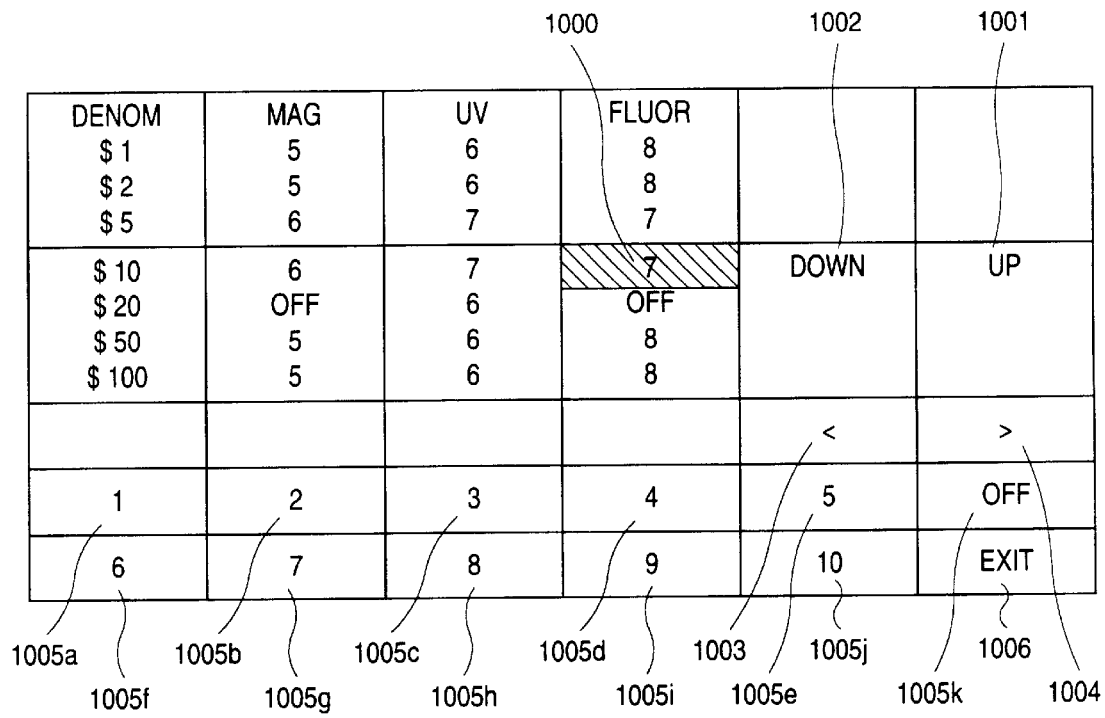

From the menu screen (FIG. 24), pressing the SUSPECT DOCUMENT key (804) will produce a screen (FIG. 27) within which an operator may select threshold levels for triggering the "suspect document" minor error condition. Nine denominations can be accommodated for international markets. In the embodiment of FIG. 27, the system permits adjustment of three types of authentication tests, namely, a magnetic test, an ultraviolet (UV) test, and a fluorescence test. The magnetic test measures the total magnetic content of a document along a scan line. The ultraviolet test measures the amount of ultraviolet light that is reflected off a document when it is illuminated by an ultraviolet light source. The fluorescence test measures the amount of fluorescent light that is emitted from a document when it is illuminated by an ultraviolet light source. These tests and sensitivity adjustments are described in more detail in co-pending U.S. patent application Ser. No. 08/494,091 filed on Jun. 23, 1995 entitled "Currency Discriminator and Authenticator" and Ser. No. 08/317,349 filed on Oct. 4, 1994 entitled "Method and Apparatus for Authenticating Documents Including Currency" which are incorporated herein by reference in their entirety. Likewise, the system may additionally include other authentication tests such as thread detection, enhanced magnetics tests including those employing a single and multiple magnetic heads, infrared detection, and color authentication tests including those described in co-pending U.S. patent application Ser. No. 08/800,053, filed on Feb. 14, 1997 entitled "Method and Apparatus for Document Identification and Authentication". These authentication tests may also employ multiple sensitivity setting by denomination and/or series.

A highlighted cursor (1000), indicated by hatching in FIG. 27, may be moved by the UP (1001) and DOWN (1002) keys and/or left and right arrow keys "<" (1003), ">" (1004)

at the right of the display to a particular selected threshold. Thereafter, thresholds may be set by touching one or more of the direct access keys (1005*a–k*) at the bottom of the screen. The OFF key (1005*k*) disables an authentication test. EXIT (1006) will bring the operator back to the menu screen of FIG. 24.

Figure 28:
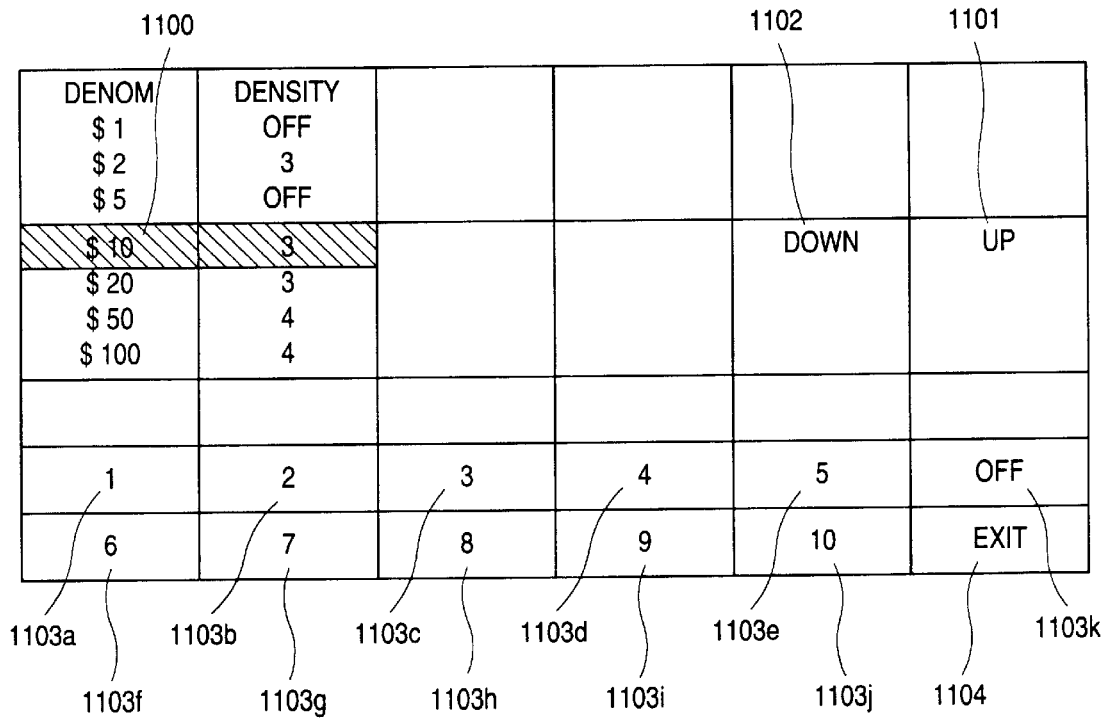

From the menu screen (FIG. 24), pressing the DENSITY key (805) will produce the screen shown in FIG. 28 within which an operator may select density levels associated with the various currency denominations. The density levels affects such functions as the detection of two or more bills fed in a stacked manner (Doubles major error). Nine denominations can be acconmmodated for international markets. A highlighted cursor (1100), indicated by hatching in FIG. 28, may be moved by the UP (1101) and DOWN (1102) keys at the right of the display to a particular selected denomination. Thereafter, density levels may be set by touching one or more of the direct access keys (1103*a–j*) at the bottom of the screen. The OFF key (1103*k*) disables density checking for the corresponding denomination. EXIT (1104) will bring the operator back to the menu screen of FIG. 24.

In one embodiment of the present invention, the display may be used to indicate recovery procedures upon the occurrence of an error condition that has stopped the machine. Error conditions can include for example, jam, double, chain, stacker fill, strap limit, denomination change, and stranger. Preferably, the recovery procedures are displayed in the form of text indicating both the error condition that has occurred and detailed instructions for the operator to follow to recover from the error condition and resume operation of the machine. For example, a jam can be identified by its location in the machine such as in pocket 1, pocket 2, infeed area, etc. Likewise, a display associated with a "strap limit" error condition is shown in FIG. 29. The display "STRAP LIMIT POCKET 1" identifies that the machine has stopped due to a "strap limit" error condition in pocket 1. The display "REMOVE NOTES AND PRESS CONT." indicates to the operator that he or she must first remove the notes in pocket 1, then press the "CONT" key (1200) to resume operation of the machine.

A further example of a recovery screen is shown in FIG. 30, illustrating a display associated with a "no call" error condition. A screen substantially similar to FIG. 30 may also be used upon the occurrence of a "suspect document" condition. The display "NO CALL PRESS KEY:" indicates to the operator that the machine has stopped due to a "no call" condition and that the operator may press one of the keys (1300*a–g*) in the display, e.g., "$1", "$2", "$5", "$10", $20", "$50" or "$100", to resume operation of the machine. The operator may thereafter observe the denomination of the "no call" document and press the appropriate key (1300*a–g*) if the operator finds the bills to be acceptable, causing the machine to add the appropriate value to the count total and resume processing the remaining notes in the stack. If the operator finds the bill unacceptable (e.g., suspect, a bill from a different country), the operator may press a CONT. key (1301) (Continue key). Generally, the operator will first remove the unacceptable bill from the output pocket first and then press the CONT. key (1301). The machine will then resume processing the remaining notes in the stack without improperly disrupting any running totals or counters.

In another embodiment of the present invention, the display may be used to enable the operator to enter data such as, for example, user identification, date, customized labels, check amounts, coin amounts, or manual bill counts. In a touch screen environment, this may be accomplished through data entry software providing a series of menus or screens, each including selection elements or "keys" which the operator may touch to activate appropriate functions related to one or more data entry modes. These features may be engaged in the setup program described above, or they may be requested on demand. If used on demand, the "keys" should be displayed upon the beginning of processing a batch of notes. FIG. 31 represents a touch screen associated with the a machine in data entry mode. The hatched keys represent functions that are engaged. The touch screen contains the following keys and displays:

LABEL (1401)
This key enables the operator to customize labels A,B, C,D through the touch panel keyboard.

ID (1402)
This key prompts the operator to enter a user identification code.

MEDIA (1403)
This key prompts the operator to enter the media type associated with the data entry, e.g., coin, check or misc.

DATE (1404)
This key prompts the operator to enter the date.

DBAL (1405)
This key prompts the operator to enter a declared balance (Batch and Sub-batch).

EXIT (1406)
This key returns the operator to the previous menu.

MODE display (1407)
This displays the selected mode of operation of the machine.

STRAP LIMIT display (1408)
This displays the strap limit associated with the mode of operation.

STRAP COUNT display (1409)
This displays the current number of a select document-type counted DENOM display (1410)
This displays the selected document-type SUB-BATCH display (1411)
This displays aggregate totals associated with a sub-batch of currency bills.

BATCH display (1412)
This displays aggregate totals associated with a batch of currency bills.

Figure 33:
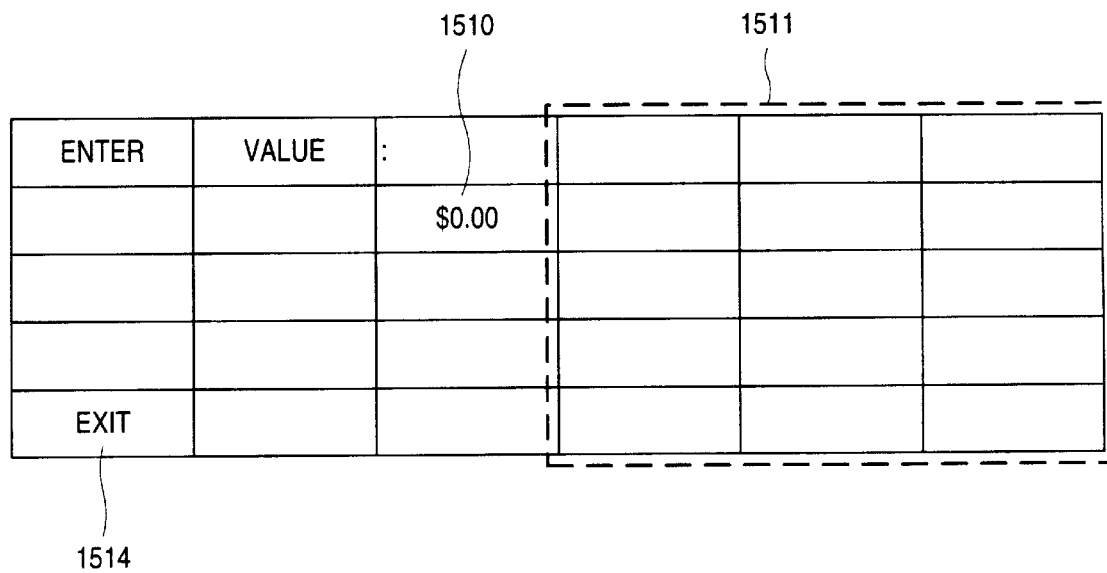
Figure 34:
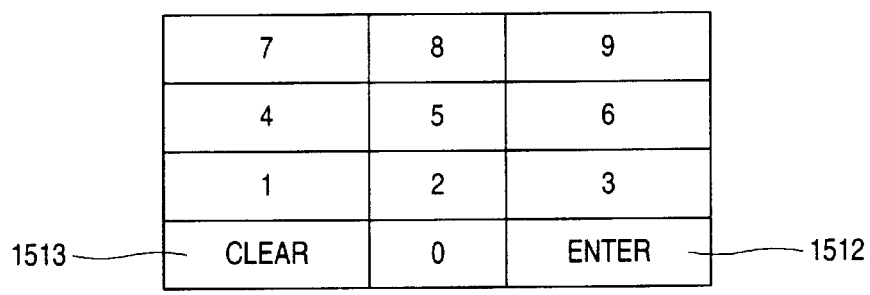
FIG. 34 is a numerical keypad according to one embodiment of the present invention.

Pressing the MEDIA key (1403) will result in the screen shown in FIG. 32 being displayed. At this screen, the operator selects what type of media is to be recorded into the systems memory by selecting either a COIN key (1501), a CHECK key (1502), or a NISC key (1503). To return to the screen of FIG. 31, the operator would select the EXIT key (1504). In the example shown in FIG. 32 the operator has indicated that the amount of a check is to be entered into the systems memory by selecting the CHECK key (1502). At this point, the screen shown in FIG. 33 appears and prompts the operator to enter the value of the check by displaying the message: "ENTER VALUE". The amount that operator the enters is displayed on the screen (1510). The operator may enter the amount by using a keyboard connected to or integrated into the machine such as that shown in FIG. 34. Alternatively, the keyboard of FIG. 34 may be displayed on the touch screen such as at area 1511 of FIG. 33. Once the operator has typed in the correct amount, it is entered into the memory of the system by selection of the ENTER key (1512). Data entry mistakes may be corrected by pressing the CLEAR key (1513). If the operator wishes to return to the previous screen (FIG. 32) without entering any amount, the EXIT key (1514) is selected. According to one embodiment, data entry as described above may be performed even while the system is processing a stack of notes. However, upon the occurrence of an error that requires presentation of other keys or functions to recover, data entry will be suspended until the machine resumes operation.

In one embodiment of the present invention, the discrimination machine is equipped with a series of communications ports to provide one-way or two-way communications link (s) between the discrimination machine and remote operators and/or other machines. This communications link may be established, for example, between another currency discrimination machine, a coin sorting machine, a cash settlement system, currency dispensers, or a remote "host" device, such as a computer, for issuing control commands and/or receiving information from the discrimination machine.

In embodiments using a "host" device, the following commands may be issued from the host, to which the discrimination machine will respond operationally:

(1) a "START" command for starting operation of the machine;
(2) a "REQUEST INFORMATION" command wherein the host may request information from the machine, such as sub-batch, batch, or day totals,
(3) a "MODE SELECTION" command wherein the host may remotely select the mode of operation for the machine,
(4) an "ADD SELECTION" command;
(5) an "SD" selection command wherein the host may remotely set sensitivity thresholds for the machine,
(6) a "STRAP SETTINGS" command;
(7) a "CLEARING" command;
(8) a "DENSITY SETTING" command;
(9) a "POCKET SELECTION" command; and
(10) an "ENDING BATCH" command.

In return, in embodiments using a "host" device, it is contemplated that the discrimination machine may send the following information to the host:

(1) a message or messages indicating the occurrence of minor error condition(s) "NO CALL", "SUSPECT DOCUMENT", "DENOMINATION CHANGE", "STRAP LIMIT", "STRANGER", "STACKER FULL" or "SEPARATE SERIES";
(2) a message or messages indicating the occurrence of major error conditions "JAM', "DOUBLE" or "CHAIN"; and
(3) maintenance messages indicating maintenance requirements or status of the machine, such as whether the machine requires cleaning or adjustment.

Many types of financial transaction features may be incorporated into the above described machines so that they can act as a cash settlement machine. The details of such cash settlement systems are described in more detail in co-pending U.S. patent application Ser. No. 08/467,585, filed on Jun. 6, 1995 for a "Cash Settlement Machine" incorporated herein by reference in its entirety.

While many of the above embodiments have been described in conjunction with U.S. currency, systems according to the present invention may alternatively or additionally process currency of other countries such as the United Kingdom, France, Germany, Japan, Spain, Canada, Italy, Brazil, Mexico, Taiwan, and Saudi Arabia. Likewise, the above systems may support the processing of multiple types of documents including, for example, checks, deposit slips, header documents, etc.

Additionally, the systems described above may contain fitness sensors such as density sensors, reflectance sensors, magnetic sensors, correlation, UV and soil sensors, tear detectors, etc. Also the systems may utilize flash memory as mentioned above and $E^2$ proms for reliable storage of data and set ups.

Additionally, the systems described above may contain unique customization features such as user-defined keys, user-defined print outs, user-defined modes of operation, user-defined document distribution parameters, user-defined set-ups. The customization features may be controlled or changed through simple input though an interface device such as a keyboard or touch screen.

User Customization

As described above and as to be further described below, according to embodiments of the present invention, the system permits the user or operator to customize the operation of the machine in a number of ways. For example, in the above described modes of operation, the user may be permitted to designate into which pocket certain bills are delivered and whether the machine should stop, e.g., deliver any no calls into pocket 2 and stop the machine after each no call is delivered to pocket 2. Additional examples of how the user may customize a system according to the present invention are described in connection with FIGS. 35–40. FIGS. 35–40 illustrate examples of displays designed to aid the operator in tailoring the operation of the machine according to the operator's preferences. These figures illustrate displays that may be used to aid in retrieval of routing and flagging information from a user such as via a routing interface having a data retrieval device such as a touch-screen. Alternatively, the data retrieval device may be some other kind of input or input/output device such as a keypad. Additionally or alternatively, information concerning whether the system should stop upon the occurrence of one or more conditions may be retrieved from the user via a flagging control interface having a flagging data retrieval device such as a touch-screen. Alternatively, the flagging data retrieval device may be some other kind of input or input/output device such as a keypad. The flagging control interface may be combined with the routing interface into a single interface system.

FIG. 35 illustrates an example of an operating parameters selection screen in which no selections have been made. The left-hand column (C1) lists various features and conditions for which the operator may make selections. The right-hand column (C3) lists the available selection choices or options associated with each feature or condition and the middle column (C2) displays the selected option for each feature or condition (in FIG. 35 no selections have been made).

Turning to FIG. 36, an example of the operating parameters selection screen for a Stranger Facing mode is illustrated. In general, options which are not available are displayed in a non-highlighted or dim manner, illustrated in FIG. 36 via striking through unavailable options, e.g., the "OFF" and "ALL" selection choices for the Target 1 denomination. Based on the selections displayed in FIG. 36, the system will deliver to pocket 1 bills having the same denomination and face orientation as the first bill in a stack. This is evident with reference to box C2,R1 which designates the target denomination as that of the "1st BILL". Additionally, box C2,R2 designates a target face orientation as the face orientation of the "1st BILL". Neither forward/reverse orientation ("orientation") nor "series" has been activated so bills are not distinguished on those bases. With respect to the designation of the Target 1 denomination, the operator may change the selection from "1st BILL" to a specific denomination, $1–$100 or to User Select (US). If User Select is chosen, at the time the mode is invoked, the operator will be prompted as to the desired selection. In the case of selecting a denomination, any available option may be chosen such as "1st BILL" or a specific denomination. This may be accomplished, for example, by pressing the screen in box C2,R1 in a touch screen environment which will cause the displayed selection to scroll through the available options. Likewise, with respect to the designation of the target face orientation, the operator may scroll through the options of "1st BILL", "FACE UP", "FACE DOWN", and "US". In boxes C3, R1 and C3,R2 the option "OFF" is not available in a Stranger Facing mode.

With respect to forward/reverse orientation, the operator may choose either "OFF", "1st BILL", FORWARD", "REVERSE", or "US". With respect to series selection, the operator may choose either "OFF", "1st BILL", "US", or scroll through any defined series groups such as those described above, e.g., in connection with the Sort Series modes. These series groups may include factory-defined series groups and user-defined groups. Additionally, the operator may be given the option to simply designate a given series or range of series, e.g., "1996+" for all bills of a 1996 or later series or "1990–1996" for all bills having a series from 1990 to 1996.

In box C2,R5, the operator may designate whether the parameters defining Target 1 should be updated upon the occurrence of a relevant condition such as a denomination change, stranger, or separate series condition. The updating may be permitted, for example, for all activated parameters defining a target denomination (e.g., denomination and face orientation in the example of FIG. 36) or alternatively, the user may elect to update only certain ones of the activated parameters (e.g., update upon a stranger condition (new denomination) but not on a reverse face condition). As displayed in FIG. 36, the Target 1 parameters are not updated during the processing of a stack of bills.

In the Stranger Facing modes, the operator is not permitted to designate a second set of target parameters and accordingly this section (C2,R6–C3,R10) of the display is dimmed.

Boxes C2,R11–C2,R19 permit the operator to designate how certain minor error conditions are to be handled, i.e., by presenting the flagged bill in pocket 1 (P1), presenting the flagged bill in pocket 2 (P2), or delivering the flagged bill to pocket 2 and continuing to process any remaining bills (CONT-2).

Additionally, for strangers, denomination changes, and separate series, the operator is also given the option of having the transport mechanism stopped with the flagged bill being maintained within the transport mechanism (ST), i.e., before the flagged bill is delivered into a pocket. Positional information obtained from an encoder may be employed to stop a bill in a controlled manner and so that the bill is stopped in a predetermined position or identifiable location. For example, the transport mechanism may be stopped such that a flagged minor error bill is located after a diverter and before a next diverter or output receptacle such as between diverter 260 and output receptacle 217b such as being adjacent to plate 278 of FIG. 2. Alternatively, using the embodiment of FIG. 2 as an example, a flagged minor error bill may be stopped before reaching diverter 260 such as being adjacent to plate 262. One embodiment of a stopping mechanism employing an interconnected CPU, optical encoder, transport mechanism, and drive motor is described in U.S. Pat. No. 5,295,196 incorporated herein in its entirety. Likewise on a currency evaluation device having only a single output receptacle such as that describe in U.S. Pat. No. 5,295,196, a flagged minor error bill such as a stranger, denomination change, or separate series bill may be stopped so that it is located at a predetermined or identifiable position within the transport mechanism (i.e., before being transport to the output receptacle).

As illustrated in FIG. 36, stranger bills, no calls, suspect documents, documents having an improper size, and unfit documents are all presented into pocket 2. Additionally, reverse faced notes are delivered to pocket 2 but do not cause the machine to halt operation. Accordingly, bills having the target denomination and target face orientation are delivered into pocket 1 while bills having the target denomination but not the target face orientation are delivered to pocket 2. The error conditions of denomination change, reverse forward-reverse orientation, and separate series have been disabled by the choices selected above, i.e., a denomination change error can not occur in a stranger mode, and by turning off orientation and series selections in boxes C2,R3–C2,R4 orientation and series error conditions will not occur.

Boxes C2,R20–C2,R23 permit the operator to set how stacker full, strap limit, chain, and double error conditions are handled. As illustrated in FIG. 36, the machine will stop upon the occurrence of a stacker full condition. Another option includes switching delivery of target notes to the non-current pocket when the current pocket becomes full provided there are no bills in the non-current pocket. Otherwise the machine will halt until one of the pockets is cleared. Box C2,R21 indicates that strap limits will be counted using the contents of both output pockets, i.e., a strap limit will occur when the combined number of target denomination bills delivered to pocket 1 (having the target face orientation) and target denomination bills delivered to pocket 2 (having a reverse face orientation) reaches the limit associated with the target denomination. When either a chain or a double error condition occurs, the machine stops with any chain or double bills being delivered into pocket 2.

Turning to FIG. 37, an example of the operating parameters selection screen for a Sort 3 mode is illustrated. Here $5 bills (having any face orientation, any forward/reverse orientation, or any series) are delivered to pocket 1 while the first non-$5 bill becomes the second target denomination and is off-sorted into pocket 2. Thereafter $5 bills are delivered to pocket 1 and target 2 denominated bills are delivered to pocket 2. Upon the occurrence of a denomination change, the denomination change bill will be presented into pocket 2 (C2,R12) and the denomination of the flagged bill will become the new target 2 denomination (C2,R10). The target 1 denomination will remain $5 as box C2,R5 indicates that this denomination should not be updated.

Turning to FIG. 38, an example of the operating parameters selection screen for a first user defined mode is illustrated. The system may permit the operator to set a number of personalized operating modes (e.g., user-defined 1, user-defined 2, etc.) Likewise the system may permit user to define the name of the modes, e.g., "Acme Bank Closing Mode", "Acme Bank Commercial Mode"). According to the selections made in FIG. 38, all face up $100 bills having a series of 1996 or later are delivered into pocket 1 while all face down $100 bills having a series of 1995 or earlier are delivered to pocket 2. When any possible minor error listed in rows R11–R19 occurs, the flagged bill is presented in pocket 2.

Information concerning user-defined modes is stored in a memory such as an $E^2$ PROM so that it can be recalled in the future such as on days subsequent to the day that it is original defined. This information is stored in such a manner that it is not lost after the power switch of the currency discriminator is turned off as in a nonvolatile memory. The definition of particular user-defined mode will remain unchanged until it is re-defined by a user of the currency discriminator. In this manner a user may define a mode of operation that is particularly adapted to the needs of the user and repeatedly recall that mode of operation whenever the user desires to operate the machine in that mode. For example, the operate could desire to process a stack of currency bills using one of the factory default modes such as the Mixed 1 mode of operation and then process of second stack of bills using an user-defined mode. In such a case, the operator would first select the factory mode desired such as Mixed 1, process the first stack of bills, then select the desired user-defined mode, and process the second stack of bills. The definitions of the factory-defined or default modes may also be stored in an $E^2$ PROM.

Turning to FIG. 39, an example of the operating parameters selection screen for a second user defined mode is illustrated. According to the selections made in FIG. 39, bills of all denominations (as in a mixed mode), are delivered into pocket 1. This is indicated by the selection of "ALL" in box C2,R1. No calls are presented in pocket 1 while suspects, improperly size bills and unfit document are presented in pocket 2. Chains and doubles are directed to pocket 1 and the machine stops.

Turning to FIG. 40, an example of the operating parameters selection screen for a third user defined mode is illustrated. According to the selections made in FIG. 40, bills of all denominations (as in a mixed mode) are delivered into pocket 2. No calls are presented in pocket 2 while suspects, improperly size bills and unfit document are presented in pocket 1. Chains and doubles are directed to pocket 1 and the machine stops.

While the invention is susceptible to various modifications and alternative forms, specific embodiments thereof have been shown by way of example in the drawings and herein described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

What is claimed is:

1. A currency evaluation device for receiving a stack of currency bills and rapidly evaluating all the bills in the stack, the device comprising:

an input receptacle adapted to receive a stack of bills to be evaluated;

exactly two output receptacles adapted to receive the bills after the bills have been evaluated;

a transport mechanism adapted to transport the bills, one at a time, from the input receptacle to the output receptacles along a transport path;

a discriminating unit adapted to count and denominate the bills, the discriminating unit including a detector positioned along the transport path between the input receptacle and the output receptacles;

a processor programmed to determine whether the bills meet or fail to meet a non-piece count related criterion, the processor being programmed to cause the transport mechanism to halt in response to a determination that a bill meets or fails to meet the criterion, a bill meeting or failing to meet the criterion being termed a flagged bill, the processor being adapted to cause the transport mechanism to halt with a flagged bill being positioned as the last bill in one of the output receptacles; and wherein bills whose denomination are determined by the discriminating unit are delivered to a first output receptacle and wherein bills whose denominations are not determined by the discriminating unit are directed to the other output receptacle, bills whose denomination are not determined by the discriminating unit being termed no call bills.

2. The currency evaluation device of claim 1 wherein the processor is adapted to cause the transport mechanism to halt after a no call bill has been delivered to the second output receptacle.

3. The currency evaluation device of claim 2 wherein the processor is adapted to cause the transport mechanism to halt with the no call bill being positioned at an identifiable location in the second output receptacle.

4. The currency evaluation device of claim 3 wherein the processor is adapted to cause the transport mechanism to halt with the no call bill being the last bill transported to the second output receptacle, wherein the criterion is the discriminating unit determining the denomination of a bill and wherein a bill failing to meet the criterion of having its denomination determined by the discriminating unit is a flagged bill.

5. The currency evaluation device of claim 1 wherein the processor is adapted to cause the transport mechanism to halt before a no call bill has been delivered to the second output receptacle.

6. The currency evaluation device of claim 5 wherein the processor is adapted to cause the transport mechanism to halt with the no call bill being located at an identifiable location within the transport mechanism.

7. A currency evaluation device for receiving a stack of currency bills and rapidly evaluating all the bills in the stack, the device comprising:

an input receptacle adapted to receive a stack of bills to be evaluated;

exactly two output receptacles adapted to receive the bills after the bills have been evaluated;

a transport mechanism adapted to transport the bills, one at a time, from the input receptacle to the output receptacles along a transport path;

a discriminating unit adapted to count and denominate the bills, the discriminating unit including a detector positioned along the transport path between the input receptacle and the output receptacles;

a processor programmed to determine whether the bills meet or fail to meet a non-piece count related criterion, the processor being programmed to cause the transport mechanism to halt in response to a determination that a bill meets or fails to meet the criterion, a bill meeting or failing to meet the criterion being termed a flagged bill, the processor being adapted to cause the transport mechanism to halt with a flagged bill being positioned as the last bill in one of the output receptacles; and wherein a bill failing to have its denomination determined by the discriminating unit is termed a no call bill, wherein the discriminating unit is further adapted to determine whether a bill has a denomination other than the target denomination being termed a stranger bill, and wherein the device is adapted to deliver stranger bills to a first output receptacle and deliver no call bills to the other output receptacle.

8. A currency evaluation device for receiving a stack of currency bills and rapidly evaluating all the bills in the stack, the device comprising:

an input receptacle adapted to receive a stack of bills to be evaluated;

exactly two output receptacles adapted to receive the bills after the bills have been evaluated;

a transport mechanism adapted to transport the bills, one at a time, from the input receptacle to the output receptacles along a transport path;

a discriminating unit adapted to count and denominate the bills, the discriminating unit including a detector positioned along the transport path between the input receptacle and the output receptacles;

a processor programmed to determine whether the bills meet or fail to meet a non-piece count related criterion, the processor being programmed to cause the transport mechanism to halt in response to a determination that a bill meets or fails to meet the criterion, a bill meeting or failing to meet the criterion being termed a flag bill, the processor being adapted to cause the transport mechanism to halt with a flagged bill being positioned as the last bill in one of the output receptacles; and wherein the discrimination unit is further adapted to determine whether a bill has a denomination other than a target denomination, a bill having a denomination other than the target denomination being termed a stranger bill and wherein the non-piece count related criterion is the discriminating unit determining that a bill is a stranger bill.

9. A currency evaluation device for receiving a stack of currency bills and rapidly evaluating all the bills in the stack, the device comprising:

an input receptacle adapted to receive a stack of bills to be evaluated;

exactly two output receptacles adapted to receive the bills after the bills have been evaluated;

a transport mechanism adapted to transport the bills, one at a time, from the input receptacle to the output receptacles along a transport path;

a discriminating unit adapted to count and denominate the bills, the discriminating unit including a detector positioned along the transport path between the input receptacle and the output receptacles;

a processor programmed to determine whether the bills meet or fail to meet a non-piece count related criterion, the processor being programmed to cause the transport mechanism to halt in response to a determination that a bill meets or fails to meet the criterion, a bill meeting or failing to meet the criterion being termed a flag bill, the processor being adapted to cause the transport mechanism to halt with a flagged bill being positioned as the last bill in one of the output receptacles; and wherein the discrimination unit is further adapted to determine whether a bill is suspect, a bill determined to be suspect being termed a suspect bill.

10. The currency evaluation device of claim 9 wherein bills whose denomination have been determined by the discriminating unit are delivered to a first output receptacle and wherein suspect bills are directed to the other output receptacle.

11. The currency evaluation device of claim 10 wherein the processor is adapted to cause the transport mechanism to halt after a suspect bill has been delivered to the second output receptacle.

12. The currency evaluation device of claim 11 wherein the processor is adapted to cause the transport mechanism to halt with the suspect bill being located at an identifiable location within the transport mechanism.

13. The currency evaluation device of claim 10 wherein the processor is adapted to cause the transport mechanism to halt after a suspect bill has been delivered to the other output receptacle.

14. The currency evaluation device of claim 13 wherein the processor is adapted to cause the transport mechanism to halt with the suspect bill being positioned at an identifiable location in the second output receptacle.

15. The currency evaluation device of claim 14 wherein the processor is adapted to cause the transport mechanism to halt with the suspect bill being the last bill transported to the second output receptacle, wherein the non-piece count criterion is a bill being suspect.

16. A currency evaluation device for receiving a stack of currency bills and rapidly evaluating all the bills in the stack, the device comprising:

an input receptacle adapted to receive a stack of bills to be evaluated;

exactly two output receptacles adapted to receive the bills after the bills have been evaluated;

a transport mechanism adapted to transport the bills, one at a time, from the input receptacle to the output receptacles along a transport path;

a discriminating unit adapted to count and denominate the bills, the discriminating unit including a detector positioned along the transport path between the input receptacle and the output receptacles;

a processor programmed to determine whether the bills meet or fail to meet a non-piece count related criterion, the processor being programmed to cause the transport mechanism to halt in response to a determination that a bill meets or fails to meet the criterion, a bill meeting or failing to meet the criterion being termed a flag bill, the processor being adapted to cause the transport mechanism to halt with a flagged bill being positioned as the last bill in one of the output receptacles; and wherein the discrimination unit is further adapted to determine whether a bill has a denomination other than a target denomination, a bill having a denomination other than the target denomination being termed a stranger bill and wherein the criterion is a bill being a stranger bill, and wherein the processor is adapted to cause the transport mechanism to halt with a stranger bill as the last bill in one of the output receptacles.

17. A currency evaluation device for receiving a stack of currency bills and rapidly evaluating all the bills in the stack, the device comprising:

an input receptacle adapted to receive a stack of bills to be evaluated;

exactly two output receptacles adapted to receive the bills after the bills have been evaluated;

a transport mechanism adapted to transport the bills, one at a time, from the input receptacle to the output receptacles along a transport path;

a discriminating unit adapted to count and denominate the bills, the discriminating unit including a detector positioned along the transport path between the input receptacle and the output receptacles;

a processor programmed to determine whether the bills meet or fail to meet a non-piece count related criterion, the processor being programmed to cause the transport mechanism to halt in response to a determination that a bill meets or fails to meet the criterion, a bill meeting or failing to meet the criterion being termed a flag bill, the processor being adapted to cause the transport mechanism to halt with a flagged bill being positioned as the last bill in one of the output receptacles; and wherein the criterion is a bill being suspect, and wherein the processor is adapted to cause the transport mechanism to halt with a suspect bill as the last bill in one of the output receptacles.

18. A currency evaluation device for receiving a stack of currency bills and rapidly evaluating all the bills in the stack, the device comprising:
an input receptacle adapted to receive a stack of bills to be evaluated;
exactly two output receptacles adapted to receive the bills after the bills have been evaluated;
a transport mechanism adapted to transport the bills, one at a time, from the input receptacle to the output receptacles along a transport path;
a discriminating unit adapted to count and denominate the bills, the discriminating unit including a detector positioned along the transport path between the input receptacle and the output receptacles;
a processor programmed to determine whether the bills meet or fail to meet a non-piece count related criterion, the processor being programmed to cause the transport mechanism to halt in response to a determination that a bill meets or fails to meet the criterion, a bill meeting or failing to meet the criterion being termed a flag bill, the processor being adapted to cause the transport mechanism to halt with a flagged bill being positioned as the last bill in one of the output receptacles; and
wherein a bill failing to have its denomination determined by the discriminating unit being termed a no call bill, and wherein the discriminating unit is further adpated to determine whether a bill is suspect.

19. The currency evaluation device of claim 18 wherein the processor is adapted to cause the transport mechanism to halt when a bill is determined to be suspect by the discriminating unit, a bill determined to be suspect by the discriminating unit being termed a suspect bill.

20. The currency evaluation device of claim 19 wherein bills whose denomination have been determined by the discriminating unit and suspect bills are delivered to a first output receptacle and wherein no call bills are delivered to the second output receptacle.

21. The currency evaluation device of claim 29 wherein the discrimination unit is further adapted to determine whether a bill has a denomination other than a target denomination, a bill having a denomination other than the target denomination being termed a stranger bill and wherein the discriminating unit further is adapted to determine whether bills are stranger bills, and wherein stranger bills are delivered to the second output receptacle.

22. The currency evaluation device of claim 21 wherein the processor is adapted to cause the transport mechanism to halt after a no call bill or a stranger bill has been delivered to the second output receptacle.

23. The currency evaluation device of claim 22 wherein the processor is adapted to cause the transport mechanism to halt with the no call bill or the stranger bill being the last bill transported to the second output receptacle.

24. The currency evaluation device of claim 21 wherein the processor is adapted to cause the transport mechanism not to halt after a no call bill or a stranger bill has been delivered to the second output receptacle.

25. The currency evaluation device of claim 24 wherein the processor is adapted to cause the transport mechanism to halt after a suspect bill has been delivered to an output receptacle.

26. The currency evaluation device of claim 18 wherein bills whose denomination have been determined by the discriminating unit are delivered to a first output receptacle and wherein no call bills are delivered to a second output receptacle.

27. The currency evaluation device of claim 26 wherein the processor is adapted to cause the transport mechanism to halt after a no call bill has been delivered to the second output receptacle.

28. A compact, high-speed United States currency evaluation device for receiving a stack of currency bills and rapidly evaluating all the bills in the stack, the device comprising:
an input receptacle adapted to receive a stack of United States currency bills of a plurality of denominations to be evaluated;
exactly two output receptacles adapted to receive the bills after the bills have been evaluated;
a transport mechanism adapted to transport the bills, one at a time, along a transport path from the input receptacle to the output receptacles at a rate of at least 800 bills per minute;
a discriminating unit adapted to count and denominate the bills including United States bills of a plurality of denominations at a rate of at least 800 bills per minute, the discriminating unit including a detector positioned along the transport path between the input receptacle and the output receptacles;
a processor programmed to flag bills meeting or failing to meet any of certain non-piece count related criteria, a bill meeting or failing to meet any of the criteria being termed a flagged bill, the processor being adapted to cause the transport mechanism to halt in response to a determination that a bill meets or fails to meet at least one of the criteria;
wherein the certain criteria include a criterion of the discriminating unit determining the denomination of a bill, a bill failing to meet the criterion of having its denomination determined by the discriminating unit being termed a no call bill, the processor being programmed to flag no call bills;
wherein the discriminating unit is further adapted to determine whether a bill has a denomination other than a target denomination, a bill having a denomination other than the target denomination being termed a stranger bill and wherein the certain criteria include the discriminating unit determining a bill is a stranger bill and wherein the processor is programmed to flag stranger bills; and
wherein the discriminating unit is further adapted to determine whether a bill is a suspect bill and wherein the certain criteria include the discriminating unit determining a bill is a suspect bill and wherein the processor is programmed to flag suspect bills.

29. The currency evaluation device of claim 28 wherein the two output receptacles consist of a first output receptacle and a second output receptacle, and wherein stranger bills and no call bills are directed to the first output receptacle and suspect bills are directed to the second output receptacle.

30. The currency evaluation device of claim 29 wherein the processor is adapted to cause the transport mechanism to halt when a no call bill or a stranger bill is delivered to the first output receptacle.

31. The currency evaluation device of claim 29 wherein the processor is adapted to cause the transport mechanism not to halt when a no call bill or a stranger bill is delivered to the first output receptacle.

32. A compact, high-speed United States currency evaluation device for receiving a stack of currency bills and rapidly evaluating all the bills in the stack, the device comprising:
an input receptacle adapted to receive a stack of United States currency bills of a plurality of denominations to be evaluated;

exactly two output receptacles adapted to receive the bills after the bills have been evaluated;

a transport mechanism adapted to transport the bills, one at a time, along a transport path from the input receptacle to the output receptacles at a rate of at least 800 bills per minute;

a discriminating unit adapted to count and denominate the bills including United States bills of a plurality of denominations at a rate of at least 800 bills per minute, the discriminating unit including a detector positioned along the transport path between the input receptacle and the output receptacles;

a processor programmed to flag bills meeting or failing to meet any of certain non-piece count related criteria, a bill meeting or failing to meet any of the criteria being termed a flagged bill, the processor being adapted to cause the transport mechanism to halt in response to a determination that a bill meets or fails to meet at least one of the criteria;

wherein the certain criteria include the discriminating unit determining the denomination of a bill and wherein the processor is adapted to cause the transport mechanism to halt when a bill fails to meet a criterion of having its denomination determined by the discriminating unit, a bill failing to meet the criterion of having its denomination determined by the discriminating unit being termed a no call bill; and wherein bills meeting the certain criteria of having their denomination determined by the discriminating unit are delivered to a first output receptacle and wherein no call bills are directed to the other output receptacle.

33. The currency evaluation device of claim 32 wherein the processor is adapted to cause the transport mechanism to halt before a no call bill has been delivered to the other output receptacle.

34. The currency evaluation device of claim 32 wherein the processor is adapted to cause the transport mechanism to halt after a no call bill has been delivered to the other output receptacle.

35. The currency evaluation device of claim 34 wherein the processor is adapted to cause the transport mechanism to halt with a no call bill being positioned at an identifiable location in the other output receptacle.

36. The currency evaluation device of claim 35 wherein the processor is adapted to cause the transport mechanism to halt with a no call bill being the last bill transported to the other output receptacle.

37. A compact, high-speed United States currency evaluation device for receiving a stack of currency bills and rapidly evaluating all the bills in the stack, the device comprising:

an input receptacle adapted to receive a stack of United States currency bills of a plurality of denominations to be evaluated;

exactly two output receptacles adapted to receive the bills after the bills have been evaluated;

a transport mechanism adapted to transport the bills, one at a time, along a transport path from the input receptacle to the output receptacles at a rate of at least 800 bills per minute;

a discriminating unit adapted to count and denominate the bills including United States bills of a plurality of denominations at a rate of at least 800 bills per minute, the discriminating unit including a detector positioned along the transport path between the input receptacle and the output receptacles;

a processor programmed to flag bills meeting or failing to meet any of certain non-piece count related criteria, a bill meeting or failing to meet any of the criteria being termed a flagged bill, the processor being adapted to cause the transport mechanism to halt in response to a determination that a bill meets or fails to meet at least one of the criteria; and wherein the discriminating unit is further adapted to determine whether bills are suspect and wherein the certain criteria include the discriminating unit determining a bill is suspect and wherein the processor is adapted to cause the transport mechanism to halt when a bill meets a criterion of being determined to be suspect by the discriminating unit, a bill being determined to be suspect being termed a suspect bill.

38. The currency evaluation device of claim 37 wherein bills whose denomination have been determined by the discriminating unit are delivered to a first output receptacle and wherein suspect bills are directed to the other output receptacle.

39. The currency evaluation device of claim 38 wherein the processor is adapted to cause the transport mechanism to halt after a suspect bill has been delivered to the other output receptacle.

40. The currency evaluation device of claim 39 wherein the processor is adapted to cause the transport mechanism to halt with the suspect bill being positioned at an identifiable location in the other output receptacle.

41. The currency evaluation device of claim 40 wherein the processor is adapted to cause the transport mechanism to halt with the suspect bill being the last bill transported to the other output receptacle.

42. The currency evaluation device of claim 38 wherein bills whose denomination have not been determined by the discriminating unit are also delivered to the other output receptacle.

43. The currency evaluation device of claim 42 wherein the processor is adapted not to halt the transport mechanism in response to the denomination of a bill not being determined.

44. The currency evaluation device of claim 38 wherein bills whose denomination have not been determined by the discriminating unit are directed to the first output receptacle.

45. A compact, high-speed United States currency evaluation device for receiving a stack of currency bills and rapidly evaluating all the bills in the stack, the device comprising:

an input receptacle adapted to receive a stack of United States currency bills of a plurality of denominations to be evaluated;

exactly two output receptacles adapted to receive the bills after the bills have been evaluated;

a transport mechanism adapted to transport the bills, one at a time, along a transport path from the input receptacle to the output receptacles at a rate of at least 800 bills per minute;

a discriminating unit adapted to count and denominate the bills including United States bills of a plurality of denominations at a rate of at least 800 bills per minute, the discriminating unit including a detector positioned along the transport path between the input receptacle and the output receptacles;

a processor programmed to flag bills meeting or failing to meet any of certain non-piece count related criteria, a bill meeting or failing to meet any of the criteria being termed a flagged bill, the processor being adapted to cause the transport mechanism to halt in response to a determination that a bill meets or fails to meet at least one of the criteria;

wherein the certain criteria include the discriminating unit determining the denomination of a bill and wherein the processor is adapted to cause the transport mechanism to halt when a bill fails to meet a criterion of having its denomination determined by the discriminating unit, a bill failing to meet a criterion of having its denomination determined by the discriminating unit being termed a no call bill, and wherein the discriminating unit further determines whether bills are suspect; and wherein the processor is also adapted to cause the transport mechanism to halt when a bill meets a second criterion of being determined to be suspect by the discriminating unit.

46. The currency evaluation device of claim 45 wherein bills whose denomination have been determined by the discriminating unit are delivered to a first output receptacle and wherein bills determined by the discriminating unit to be suspect and bills whose denomination have not been determined by the discriminating unit are directed to the other output receptacle.

47. The currency evaluation device of claim 46 wherein the processor is adapted to cause the transport mechanism to halt after a no call bill or a suspect bill has been delivered to the other output receptacle.

48. The currency evaluation device of claim 47 wherein the processor is adapted to cause the transport mechanism to halt with the no call bill or the suspect bill being the last bill transported to the other output receptacle.

49. The currency evaluation device of claim 45 wherein bills whose denomination have been determined by the discriminating unit are delivered to a first output receptacle and wherein bills whose denomination have not been determined by the discriminating unit are directed to the other output receptacle.

50. The currency evaluation device of claim 49 wherein bills determined by the discriminating unit to be suspect are delivered to the first output receptacle.

51. A currency evaluation device for receiving a stack of currency bills and rapidly evaluating all the bills in the stack, the device comprising:

an input receptacle adapted to receive a stack of bills to be evaluated;

exactly two output receptacles adapted to receive the bills after the bills have been evaluated;

a transport mechanism adapted to transport the bills, one at a time, along a transport path from the input receptacle to the output receptacles;

a discriminating unit adapted to count and denominate the bills including bills of a plurality of denominations, the discriminating unit including at least one detector positioned along the transport path between the input receptacle and the output receptacles;

means for flagging a bill when the denomination of the bill is not determined by the discriminating unit, wherein the means for flagging is adapted to cause the transport mechanism to halt when a bill whose denomination has not been determined is encountered;

wherein the device is adapted to transport bills which have been denominated including bills of a plurality of denominations to a first output receptacle; and wherein the device is adapted to transport bills which have not been denominated to a second output receptacle, the second output receptacle being different than the first output receptacle receiving bills which have been denominated.

52. The currency evaluation device of claim 51 wherein the first and second output receptacles have a stacking mechanism associated therewith and adapted to re-stack denominated bills in the first output receptacle and re-stack bills which have not been denominated in the second output receptacle.

53. A currency evaluation device for receiving a stack of currency bills and rapidly evaluating all the bills in the stack, the device comprising:

an input receptacle adapted to receive a stack of bills to be evaluated;

exactly two output receptacles adapted to receive the bills after the bills have been evaluated;

a transport mechanism adapted to transport the bills, one at a time, along a transport path from the input receptacle to the output receptacles;

a discriminating unit including at least one detector positioned along the transport path between the input receptacle and output receptacle, the discriminating unit being adapted to count and determine the denomination of the bills and determine whether the bills are suspect; and means for flagging a bill when the bill is determined to be suspect by the discriminating unit; wherein the means for flagging is adapted to cause the transport mechanism to halt when the discriminating unit determines that a bill is suspect.

54. The currency evaluation device of claim 53 wherein the currency bills comprise United States currency and the discriminating unit is adapted to denominate United States currency bills of a plurality of denominations.

55. The currency evaluation device of claim 53 wherein the discriminating unit is adapted to denominate the bills independent of the size of the bills.

56. The currency evaluation device of claim 53 wherein the means for flagging is adapted to cause the transport mechanism to halt when the discriminating unit determines that a bill is suspect with the bill which is determined to be suspect being the last bill transported to one of the output receptacles.

57. The currency evaluation device of claim 53 wherein the detector of the discriminating unit includes a stationary optical scanning head adapted to scan at least a preselected segment of each bill transported between the input and output receptacles by the transport mechanism and produce an output signal representing the scanned image, and wherein the discriminating unit includes a processor adapted to receive the output signal and determine the denomination of each scanned bill.

58. A high-speed, United States currency evaluation device for receiving a stack of currency bills and rapidly evaluating all the bills in the stack, the device comprising:

an input receptacle adapted to receive a stack of bills to be evaluated;

exactly two output receptacles adapted to receive the bills after the bills have been evaluated, at least one of the output receptacles being adapted to receive more than one denomination of bills;

a transport mechanism adapted to transport the bills, one at a time, along a transport path from the input receptacle to the output receptacles at a rate in excess of 800 bills per minute;

a discriminating unit adapted to count and denominate the bills including United States currency bills of a plurality of denominations at a rate in excess of 800 bills per minute, the discriminating unit including a detector positioned along the transport path between the input receptacle and the output receptacles;

a processor programmed to flag bills meeting or failing to meet any of certain non-piece count criteria, a bill meeting or failing to meet any of the criteria being termed a flagged bill; wherein the processor is adapted to cause the transport mechanism to halt in response to a determination that a bill meets or fails to meet a given one or ones of the criteria;

wherein the processor is adapted to cause the transport mechanism to halt with a flagged bill meeting or failing to meet at least a given set of the criteria being positioned in one of the output receptacles;

wherein the certain criteria include the discriminating unit determining the denomination of a bill, a bill failing to meet a criterion of having its denomination determined by the discriminating unit being termed a no call bill; and wherein the discriminating unit is further adapted to determine whether a bill has a denomination other than a target denomination, a bill having a denomination other than the target denomination being termed a stranger bill and wherein the certain criteria include the discriminating unit determining a bill is a stranger bill.

59. The currency evaluation device of claim 58 wherein no call bills are delivered to a first output receptacle, and wherein stranger bills are delivered to a second output receptacle.

60. The currency evaluation device of claim 58 wherein the discriminating unit is further adapted to determine whether a bill is suspect and wherein the certain criteria include the discriminating unit determining a bill is suspect, a bill determined to be suspect being termed a suspect bill.

61. The currency evaluation device of claim 60 wherein the output receptacles include a reject receptacle, wherein no call bills and stranger bills are directed to the reject receptacle, and suspect bills are directed to the other one of the output receptacles.

62. The currency evaluation device of claim 61 wherein the processor is adapted to cause the transport mechanism to halt when a bill is directed to the reject receptacle.

63. The currency evaluation device of claim 61 wherein the processor is adapted to cause the transport mechanism not to halt when a bill is directed to the reject receptacle.

64. A high-speed, United States currency evaluation device for receiving a stack of currency bills and rapidly evaluating all the bills in the stack, the device comprising:

an input receptacle adapted to receive a stack of bills to be evaluated;

exactly two output receptacles adapted to receive the bills after the bills have been evaluated, at least one of the output receptacles being adapted to receive more than one denomination of bills;

a transport mechanism adapted to transport the bills, one at a time, along a transport path from the input receptacle to the output receptacles at a rate in excess of 800 bills per minute;

a discriminating unit adapted to count and denominate the bills including United States currency bills of a plurality of denominations at a rate in excess of 800 bills per minute, the discriminating unit including a detector positioned along the transport path between the input receptacle and the output receptacles;

a processor programmed to flag bills meeting or failing to meet any of certain non-piece count criteria, a bill meeting or failing to meet any of the criteria being termed a flagged bill; wherein the processor is adapted to cause the transport mechanism to halt in response to a determination that a bill meets or fails to meet a given one or ones of the criteria;

wherein the processor is adapted to cause the transport mechanism to halt with a flagged bill meeting or failing to meet at least a given set of the criteria being positioned in one of the output receptacles; and wherein the output receptacles include a reject receptacle, and wherein the processor is adapted to cause the transport mechanism to deliver flagged bills to the reject receptacle.

65. A high-speed, United States currency evaluation device for receiving a stack of currency bills and rapidly evaluating all the bills in the stack, the device comprising:

an input receptacle adapted to receive a stack of bills to be evaluated;

exactly two output receptacles adapted to receive the bills after the bills have been evaluated, at least one of the output receptacles being adapted to receive more than one denomination of bills;

a transport mechanism adapted to transport the bills, one at a time, along a transport path from the input receptacle to the output receptacles at a rate in excess of 800 bills per minute;

a discriminating unit adapted to count and denominate the bills including United States currency bills of a plurality of denominations at a rate in excess of 800 bills per minute, the discriminating unit including a detector positioned along the transport path between the input receptacle and the output receptacles;

a processor programmed to flag bills meeting or failing to meet any of certain non-piece count criteria, a bill meeting or failing to meet any of the criteria being termed a flagged bill; wherein the processor is adapted to cause the transport mechanism to halt in response to a determination that a bill meets or fails to meet a given one or ones of the criteria;

wherein the processor is adapted to cause the transport mechanism to halt with a flagged bill meeting or failing to meet at least a given set of the criteria being positioned in one of the output receptacles; and wherein the discriminating unit is further adapted to determine whether a bill has a denomination other than a target denomination, a bill having a denomination other than the target denomination being termed a stranger bill and wherein the certain criteria include the discriminating unit determining a bill is a stranger bill.

66. A high-speed, United States currency evaluation device for receiving a stack of currency bills and rapidly evaluating all the bills in the stack, the device comprising:

an input receptacle adapted to receive a stack of bills to be evaluated;

exactly two output receptacles adapted to receive the bills after the bills have been evaluated, at least one of the output receptacles being adapted to receive more than one denomination of bills;

a transport mechanism adapted to transport the bills, one at a time, along a transport path from the input receptacle to the output receptacles at a rate in excess of 800 bills per minute;

a discriminating unit adapted to count and denominate the bills including United States currency bills of a plurality of denominations at a rate in excess of 800 bills per minute, the discriminating unit including a detector positioned along the transport path between the input receptacle and the output receptacles;

a processor programmed to flag bills meeting or failing to meet any of certain non-piece count criteria, a bill meeting or failing to meet any of the criteria being termed a flagged bill; wherein the processor is adapted to cause the transport mechanism to halt in response to a determination that a bill meets or fails to meet a given one or ones of the criteria;

wherein the processor is adapted to cause the transport mechanism to halt with a flagged bill meeting or failing to meet at least a given set of the criteria being positioned in one of the output receptacles; and wherein the discriminating unit is further adapted to determine whether a bill is suspect and wherein the certain criteria include the discriminating unit determining a bill is suspect, a bill determined to be suspect being termed a suspect bill.

67. A currency evaluation device for receiving a stack of currency bills and rapidly evaluating all the bills in the stack, the device comprising:

an input receptacle positioned to receive a stack of bills to be evaluated;

exactly two output receptacles positioned to receive the bills after the bills have been evaluated;

a transport mechanism comprising a transport drive motor and transport rollers, the transport mechanism located between the input receptacle and the output receptacles to transport the bills, one at a time, from the input receptacle to the output receptacles along a transport path;

a discriminating unit comprising a processor and at least one detector positioned along the transport path between the input receptacle and the output receptacles, the detector being adapted to generate a characteristic information output signal in response to detected characteristic information, the characteristic information output signal being electrically coupled to the processor, the processor being adapted to receive the characteristic information output signal and generate a denomination signal in response thereto;

a flagging device comprising a processor and an encoder linked to the transport mechanism, the encoder being adapted to produce tracking signals in response to the physical movement of the bills, the processor being adapted to generate a no call signal when the denomination of a bill is not determined by the processor; wherein the flagging device is adapted to generate a stopping signal in response to the no call signal and wherein the transport drive motor is adapted to stop in response to the stopping signal;

wherein the device is adapted to transport bills which have been denominated to a first output receptacle; and wherein the device is adapted to transport bills which have not been denominated to the other output receptacle.

68. The currency evaluation device of claim 67 wherein the first and second output receptacles have a stacking mechanism associated therewith and which is adapted to re-stack denominated bills in the first output receptacle and re-stack bills which have not been denominated in the second output receptacle.

69. A currency evaluation device for receiving a stack of currency bills and rapidly evaluating all the bills in the stack, the device comprising:

an input receptacle positioned to receive a stack of bills to be evaluated;

exactly two output receptacles positioned to receive the bills after the bills have been evaluated;

a transport mechanism comprising a transport drive motor and transport rollers, the transport mechanism located between the input receptacle and the output receptacle to transport the bills, one at a time, from the input receptacle to the output receptacles along a transport path;

a discriminating unit comprising a detector positioned along the transport path between the input receptacle and the output receptacle and comprising a processor, the detector generating a characteristic information output signal in response to detected characteristic information, the characteristic information output signal being electrically coupled to the processor, the processor being adapted to receive the characteristic information output signal and generate a denomination signal in response thereto; the processor also being adapted to generate a suspect signal when a bill is determined to be suspect by the processor, and a flagging device comprising a processor and an encoder linked to the transport mechanism, the encoder producing tracking signals in response to the physical movement of the bills; wherein the flagging device is adapted to generate a stopping signal in response to the suspect signal and wherein the transport drive motor is adapted to stop in response to the stopping signal.

70. The currency evaluation device of claim 69 wherein the input receptacle is adapted to receive and the processor is adapted to denominate bills of a plurality of United States denominations.

71. The currency evaluation device of claim 69 wherein the processor is adapted to denominate currency bills independently of the size of the bills.

72. The currency evaluation device of claim 69 wherein the processor is adapted to denominate currency bills of a plurality of denominations, bills of at least two of the denominations having the same dimensions.

73. The currency evaluation device of claim 69 wherein the processor is adapted to denominate currency bills of a plurality of denominations, genuine bills of the plurality of denominations having a plurality of images associated therewith, the plurality of images defining the plurality of denominations and wherein the processor is adapted to distinguish among the plurality of denominations by scanning the image associated with each of the bills.

74. A currency evaluation device for receiving a stack of currency bills and rapidly evaluating all the bills in the stack, the device comprising:

an input receptacle adapted to receive a stack of bills to be evaluated;

exactly two output receptacles adapted to receive the bills after the bills have been evaluated;

a transport mechanism adapted to transport the bills, one at a time, along a transport path from the input receptacle to the output receptacles;

a discriminating unit adapted to count and denominate the bills, the discriminating unit including a detector positioned along the transport path between the input receptacle and the output receptacles;

a processor programmed to cause the transport mechanism to halt in a predetermined manner in response to a determination that a bill meets a stranger bill criterion and in response to a determination that a bill meets a no call bill criterion, and wherein a bill which meets the stranger bill criterion is termed a stranger bill, and wherein a bill which meets the no call bill criterion is termed a no call bill; and wherein the processor is adapted to cause the transport mechanism to halt with a bill meeting a no call bill criterion or a stranger bill criterion being positioned in one of the output receptacles.

75. A currency evaluation device for receiving a stack of currency bills and rapidly evaluating all the bills in the stack, the device comprising:

an input receptacle adapted to receive a stack of bills to be evaluated;

exactly two output receptacles adapted to receive the bills after the bills have been evaluated;

a transport mechanism adapted to transport the bills, one at a time, along a transport path from the input receptacle to the output receptacles;

a discriminating unit adapted to count and denominate the bills, the discriminating unit including a detector positioned along the transport path between the input receptacle and the output receptacles;

a processor programmed to cause the transport mechanism to halt in a predetermined manner in response to a determination that a bill meets a stranger bill criterion and in response to a determination that a bill meets a no call bill criterion, and wherein a bill which meets the stranger bill criterion is termed a stranger bill, and wherein a bill which meets the no call bill criterion is termed a no call bill; and wherein the processor is adapted to cause the transport mechanism to halt with a bill meeting a no call bill criterion or a stranger bill criterion being located at a predetermined position.

76. A currency evaluation device for receiving a stack of currency bills and rapidly evaluating all the bills in the stack, the device comprising:

an input receptacle adapted to receive a stack of bills to be evaluated;

exactly two output receptacles adapted to receive the bills after the bills have been evaluated;

a transport mechanism adapted to transport the bills, one at a time, along a transport path from the input receptacle to the output receptacles;

a discriminating unit adapted to count and denominate the bills, the discriminating unit including a detector positioned along the transport path between the input receptacle and the output receptacles;

a processor programmed to cause the transport mechanism to halt in a predetermined manner in response to a determination that a bill meets a stranger bill criterion and in response to a determination that a bill meets a no call bill criterion, and wherein a bill which meets the stranger bill criterion is termed a stranger bill, and wherein a bill which meets the no call bill criterion is termed a no call bill; and wherein the discriminating unit is further adapted to determine whether bills are suspect and wherein one of a criterion is the discriminating unit determining a bill is suspect, a bill determined to be suspect being termed a suspect bill.

77. The currency evaluation device of claim 76 wherein the output receptacles include a reject receptacle, and wherein stranger and no call bills are delivered to the reject receptacle and wherein suspect bills are delivered to the other one of the output receptacles.

78. The currency evaluation device of claim 77 wherein the processor is adapted to cause the transport mechanism to halt when a bill meeting the no call criterion or the stranger criterion is delivered to the reject receptacle.

* * * * *